US011833034B2

(12) United States Patent
Argento et al.

(10) Patent No.: US 11,833,034 B2
(45) Date of Patent: Dec. 5, 2023

(54) PROSTHETIC CARDIAC VALVE DEVICES, SYSTEMS, AND METHODS

(71) Applicant: Shifamed Holdings, LLC, Campbell, CA (US)

(72) Inventors: Claudio Argento, Felton, CA (US); Andrew Backus, Santa Cruz, CA (US); Alice Yang, Campbell, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 0 days.

(21) Appl. No.: 16/723,537

(22) Filed: Dec. 20, 2019

(65) Prior Publication Data
US 2020/0261220 A1    Aug. 20, 2020

Related U.S. Application Data

(60) Provisional application No. 62/784,280, filed on Dec. 21, 2018, provisional application No. 62/815,791, filed on Jan. 13, 2016, provisional application No. 62/851,245, filed on Jan. 25, 2016.

(51) Int. Cl.
*A61F 2/24* (2006.01)

(52) U.S. Cl.
CPC .......... *A61F 2/2409* (2013.01); *A61F 2/2418* (2013.01); *A61F 2/2469* (2013.01); *A61F 2210/0014* (2013.01)

(58) Field of Classification Search
CPC ........ A61F 2/2409; A61F 2/2418; A61F 2/24; A61F 2/2469; A61F 2/2457; A61B 2017/0649
See application file for complete search history.

(56) References Cited

U.S. PATENT DOCUMENTS

| 5,002,563 | A | 3/1991 | Pyka et al. |
| 5,327,905 | A | 7/1994 | Avitall |
| 5,356,424 | A | 10/1994 | Buzerak et al. |
| 5,370,685 | A | 12/1994 | Stevens |
| 5,582,616 | A | 12/1996 | Bolduc et al. |
| 5,755,601 | A | 5/1998 | Jones |

(Continued)

FOREIGN PATENT DOCUMENTS

| AU | 2012261727 B2 | 10/2015 |
| AU | 2019246822 B2 | 8/2020 |

(Continued)

OTHER PUBLICATIONS

Westaby et al.; Adult human valve dimensions and their surgical significance; The American Journal of Cardiology; 53(4); pp. 552-556; Feb. 1984.

(Continued)

*Primary Examiner* — Jason-Dennis N Stewart
(74) *Attorney, Agent, or Firm* — Shay Glenn LLP

(57) ABSTRACT

A heart valve prosthesis for replacing a diseased native valve in a patient, the valve includes a compressible and expandable frame structure and an anchor connected to an outer periphery of the frame structure. The anchor comprises a free end and has a flat spiral shape. The valve may further include a valve segment mounted within the frame structure and expanded with the frame structure. The frame structure may be configured for receiving a valve segment.

32 Claims, 54 Drawing Sheets

(56) References Cited

U.S. PATENT DOCUMENTS

| | | |
|---|---|---|
| 5,779,669 A | 7/1998 | Haissaguerre et al. |
| 5,873,835 A | 2/1999 | Hastings et al. |
| 5,944,690 A | 8/1999 | Falwell et al. |
| 5,997,526 A | 12/1999 | Giba et al. |
| 6,048,339 A | 4/2000 | Zirps et al. |
| 6,053,873 A | 4/2000 | Govari et al. |
| 6,254,550 B1 | 7/2001 | McNamara et al. |
| 6,419,695 B1 | 7/2002 | Gabbay |
| 6,419,696 B1 | 7/2002 | Ortiz et al. |
| 6,530,952 B2 | 3/2003 | Vesely |
| 6,533,783 B1 | 3/2003 | Töllner |
| 6,641,553 B1 | 11/2003 | Chee et al. |
| 6,752,813 B2 | 6/2004 | Goldfarb et al. |
| 6,908,478 B2 | 6/2005 | Alferness et al. |
| 6,964,684 B2 | 11/2005 | Ortiz et al. |
| 6,974,476 B2 | 12/2005 | McGuckin, Jr. et al. |
| 7,077,861 B2 | 7/2006 | Spence |
| 7,101,395 B2 | 9/2006 | Tremulis et al. |
| 7,125,421 B2 | 10/2006 | Tremulis et al. |
| 7,160,322 B2 | 1/2007 | Gabbay |
| 7,175,656 B2 | 2/2007 | Khairkhahan |
| 7,201,771 B2 | 4/2007 | Lane |
| 7,226,467 B2 | 6/2007 | Lucatero et al. |
| 7,381,219 B2 | 1/2008 | Salahieh et al. |
| 7,329,279 B2 | 2/2008 | Haug et al. |
| 7,445,631 B2 | 11/2008 | Salahieh et al. |
| 7,470,285 B2 | 12/2008 | Nugent et al. |
| 7,527,647 B2 | 5/2009 | Spence |
| 7,563,267 B2 | 7/2009 | Goldfarb et al. |
| 7,594,903 B2 | 9/2009 | Webler et al. |
| 7,604,646 B2 | 10/2009 | Goldfarb et al. |
| 7,608,091 B2 | 10/2009 | Goldfarb et al. |
| 7,618,449 B2 | 11/2009 | Tremulis et al. |
| 7,621,948 B2 | 11/2009 | Herrmann et al. |
| 7,666,204 B2 | 2/2010 | Thornton et al. |
| 7,704,269 B2 | 4/2010 | St. Goar et al. |
| 7,731,705 B2 | 6/2010 | Wardle |
| 7,748,389 B2 | 7/2010 | Salahieh et al. |
| 7,749,266 B2 | 7/2010 | Forster et al. |
| 7,780,725 B2 | 8/2010 | Haug et al. |
| 7,799,069 B2 | 9/2010 | Bailey et al. |
| 7,811,296 B2 | 10/2010 | Goldfarb et al. |
| 7,824,442 B2 | 11/2010 | Salahieh et al. |
| 7,824,443 B2 | 11/2010 | Salahieh et al. |
| 7,846,203 B2 | 12/2010 | Cribier |
| 7,947,075 B2 | 5/2011 | Goetz et al. |
| 7,951,195 B2 | 5/2011 | Antonsson et al. |
| 7,959,666 B2 | 6/2011 | Salahieh et al. |
| 7,988,724 B2 | 8/2011 | Salahieh et al. |
| 8,021,421 B2 | 9/2011 | Fogarty et al. |
| 8,052,749 B2 | 11/2011 | Salahieh et al. |
| 8,052,750 B2 | 11/2011 | Tuval et al. |
| 8,062,355 B2 | 11/2011 | Figulla et al. |
| 8,070,800 B2 | 12/2011 | Lock et al. |
| 8,075,615 B2 | 12/2011 | Eberhardt et al. |
| 8,096,985 B2 | 1/2012 | Legaspi et al. |
| 8,147,541 B2 | 4/2012 | Forster et al. |
| 8,147,542 B2 | 4/2012 | Maisano et al. |
| 8,182,528 B2 | 5/2012 | Salahieh et al. |
| 8,216,256 B2 | 7/2012 | Raschdorf et al. |
| 8,236,049 B2 | 8/2012 | Rowe et al. |
| 8,241,351 B2 | 8/2012 | Cabiri |
| 8,251,977 B2 | 8/2012 | Partlett |
| 8,252,050 B2 | 8/2012 | Maisano et al. |
| 8,287,584 B2 | 10/2012 | Salahieh et al. |
| 8,313,526 B2 | 11/2012 | Hoffman et al. |
| 8,323,241 B2 | 12/2012 | Salahieh et al. |
| 8,323,336 B2 | 12/2012 | Hill et al. |
| 8,328,868 B2 | 12/2012 | Paul et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,366,767 B2 | 2/2013 | Zhang |
| 8,403,981 B2 | 3/2013 | Forster et al. |
| 8,403,983 B2 | 3/2013 | Quadri et al. |
| 8,414,643 B2 | 4/2013 | Tuval et al. |
| 8,414,644 B2 | 4/2013 | Quadri et al. |
| 8,414,645 B2 | 4/2013 | Dwork et al. |
| 8,425,593 B2 | 4/2013 | Braido et al. |
| 8,449,599 B2 | 5/2013 | Chau et al. |
| 8,454,686 B2 | 6/2013 | Alkhatib |
| 8,465,541 B2 | 6/2013 | Dwork |
| 8,500,800 B2 | 8/2013 | Maisano et al. |
| 8,512,401 B2 | 8/2013 | Murray et al. |
| 8,523,881 B2 | 9/2013 | Cabiri et al. |
| 8,545,553 B2 | 10/2013 | Zipory et al. |
| 8,556,963 B2 | 10/2013 | Tremulis et al. |
| 8,562,645 B2 | 10/2013 | Stone et al. |
| 8,562,673 B2 | 10/2013 | Yeung et al. |
| 8,579,962 B2 | 11/2013 | Salahieh et al. |
| 8,603,157 B2 | 12/2013 | Seguin et al. |
| 8,603,160 B2 | 12/2013 | Salahieh et al. |
| 8,623,075 B2 | 1/2014 | Murray et al. |
| 8,628,570 B2 | 1/2014 | Seguin |
| 8,641,727 B2 | 2/2014 | Starksen et al. |
| 8,652,202 B2 | 2/2014 | Alon et al. |
| 8,652,203 B2 | 2/2014 | Quadri et al. |
| 8,657,872 B2 | 2/2014 | Seguin |
| 8,685,086 B2 | 4/2014 | Navia et al. |
| 8,696,693 B2 | 4/2014 | Najafi et al. |
| 8,715,300 B2 | 5/2014 | Najafi et al. |
| 8,715,342 B2 | 5/2014 | Zipory et al. |
| 8,740,976 B2 | 6/2014 | Tran et al. |
| 8,784,479 B2 | 7/2014 | Antonsson et al. |
| 8,790,367 B2 | 7/2014 | Nguyen et al. |
| 8,808,368 B2 | 8/2014 | Maisano et al. |
| 8,828,078 B2 | 9/2014 | Salahieh et al. |
| 8,834,564 B2 | 9/2014 | Tuval et al. |
| 8,840,663 B2 | 9/2014 | Salahieh et al. |
| 8,840,664 B2 | 9/2014 | Karapetian et al. |
| 8,845,588 B2 | 9/2014 | Bruszewski |
| 8,852,271 B2 | 10/2014 | Murray et al. |
| 8,876,893 B2 | 11/2014 | Dwork et al. |
| 8,876,894 B2 | 11/2014 | Tuval et al. |
| 8,876,895 B2 | 11/2014 | Tuval et al. |
| 8,900,294 B2 | 12/2014 | Paniagua et al. |
| 8,911,494 B2 | 12/2014 | Hammer et al. |
| 8,920,369 B2 | 12/2014 | Salahieh et al. |
| 8,926,690 B2 | 1/2015 | Kovalsky |
| 8,926,696 B2 | 1/2015 | Cabiri et al. |
| 8,926,697 B2 | 1/2015 | Gross et al. |
| 8,940,002 B2 | 1/2015 | Goertzen |
| 8,940,044 B2 | 1/2015 | Hammer et al. |
| 8,951,299 B2 | 2/2015 | Paul et al. |
| 8,986,371 B2 * | 3/2015 | Quill ............... A61B 17/1285 623/2.11 |
| 8,998,980 B2 | 4/2015 | Shipley et al. |
| 9,005,273 B2 | 4/2015 | Salahieh et al. |
| 9,011,515 B2 | 4/2015 | Schweich et al. |
| 9,011,523 B2 | 4/2015 | Seguin |
| 9,011,530 B2 | 4/2015 | Reich et al. |
| 9,017,408 B2 | 4/2015 | Siegal et al. |
| 9,023,100 B2 | 5/2015 | Quadri et al. |
| 9,034,032 B2 | 5/2015 | McLean et al. |
| 9,039,757 B2 | 5/2015 | McLean et al. |
| 9,056,009 B2 | 6/2015 | Keränen |
| 9,061,120 B2 | 6/2015 | Osypka et al. |
| 9,095,431 B2 | 8/2015 | Yu et al. |
| 9,119,719 B2 | 9/2015 | Zipory et al. |
| 9,125,739 B2 | 9/2015 | Paniagua et al. |
| 9,125,740 B2 | 9/2015 | Morriss et al. |
| 9,155,619 B2 | 10/2015 | Liu et al. |
| 9,168,129 B2 | 10/2015 | Valdez et al. |
| 9,168,131 B2 | 10/2015 | Yohanan et al. |
| 9,173,713 B2 | 11/2015 | Hart et al. |
| 9,173,737 B2 | 11/2015 | Hill et al. |
| 9,180,006 B2 | 11/2015 | Keränen |
| 9,226,823 B2 | 1/2016 | Dwork |
| 9,232,995 B2 | 1/2016 | Kovalsky et al. |
| 9,277,994 B2 | 3/2016 | Miller et al. |
| 9,289,297 B2 | 3/2016 | Wilson et al. |
| 9,295,547 B2 | 3/2016 | Costello et al. |
| 9,301,756 B2 | 4/2016 | Wardle |
| 9,301,836 B2 | 4/2016 | Buchbinder et al. |

(56) References Cited

U.S. PATENT DOCUMENTS

| | | |
|---|---|---|
| 9,320,597 B2 | 4/2016 | Savage et al. |
| 9,343,224 B2 | 5/2016 | Zilbershlag |
| 9,358,110 B2 | 6/2016 | Paul et al. |
| 9,414,915 B2 | 8/2016 | Lombardi et al. |
| 9,427,315 B2 | 8/2016 | Schweich et al. |
| 9,439,757 B2 | 9/2016 | Wallace et al. |
| 9,468,525 B2 | 10/2016 | Kovalsky |
| 9,474,606 B2 | 10/2016 | Zipory et al. |
| 9,474,840 B2 | 10/2016 | Siess |
| 9,480,559 B2 | 11/2016 | Vidlund et al. |
| 9,492,273 B2 | 11/2016 | Wallace et al. |
| 9,526,487 B2 | 12/2016 | Rahmani |
| 9,526,609 B2 | 12/2016 | Salahieh et al. |
| 9,532,868 B2 | 1/2017 | Braido |
| 9,532,870 B2 | 1/2017 | Cooper et al. |
| 9,561,102 B2 | 2/2017 | Rust et al. |
| 9,579,198 B2 | 2/2017 | Deem et al. |
| 9,636,224 B2 | 5/2017 | Zipory et al. |
| 9,636,481 B2 | 5/2017 | Campbell et al. |
| 9,662,202 B2 | 5/2017 | Quill et al. |
| 9,662,206 B2 | 5/2017 | Börtlein et al. |
| 9,662,209 B2 | 5/2017 | Gross et al. |
| 9,675,454 B2 | 6/2017 | Vidlund et al. |
| 9,681,952 B2 | 6/2017 | Hacohen et al. |
| 9,687,343 B2 | 6/2017 | Börtlein et al. |
| 9,724,192 B2 | 8/2017 | Sheps et al. |
| 9,730,790 B2 | 8/2017 | Quadri et al. |
| 9,730,793 B2 | 8/2017 | Reich et al. |
| 9,744,031 B2 | 8/2017 | Girard et al. |
| 9,744,038 B2 | 8/2017 | Dahlgren et al. |
| 9,750,605 B2 | 9/2017 | Ganesan et al. |
| 9,763,779 B2 | 9/2017 | Börtlein et al. |
| 9,763,780 B2 | 9/2017 | Morriss et al. |
| 9,814,611 B2 | 11/2017 | Cartledge et al. |
| 9,827,090 B2 | 11/2017 | Hill et al. |
| 9,861,480 B2 | 1/2018 | Zakai et al. |
| 9,867,700 B2 | 1/2018 | Bakis et al. |
| 9,867,702 B2 | 1/2018 | Keränen et al. |
| 9,877,833 B1 | 1/2018 | Bishop et al. |
| 9,883,941 B2 | 2/2018 | Hastings et al. |
| 9,889,003 B2 | 2/2018 | Börtlein et al. |
| 9,895,221 B2 | 2/2018 | Vidlund |
| 9,895,222 B2 | 2/2018 | Zeng et al. |
| 9,901,444 B2 | 2/2018 | Valdez et al. |
| 9,918,840 B2 | 3/2018 | Reich et al. |
| D815,744 S | 4/2018 | Ratz et al. |
| 9,949,825 B2 | 4/2018 | Braido et al. |
| 9,949,828 B2 | 4/2018 | Sheps et al. |
| 9,950,142 B2 | 4/2018 | Eversull et al. |
| 9,968,452 B2 | 5/2018 | Sheps et al. |
| 9,974,647 B2 | 5/2018 | Ganesan et al. |
| 9,974,650 B2 | 5/2018 | Nguyen-Thien-Nhon et al. |
| 9,999,504 B2 | 6/2018 | Czyscon et al. |
| 10,004,599 B2 | 6/2018 | Rabito et al. |
| 10,016,271 B2 | 7/2018 | Morriss et al. |
| 10,016,272 B2 | 7/2018 | Spence et al. |
| 10,028,832 B2 | 7/2018 | Quill et al. |
| 10,029,037 B2 | 7/2018 | Muller et al. |
| 10,034,747 B2 | 7/2018 | Harewood |
| 10,034,749 B2 | 7/2018 | Spence et al. |
| 10,039,637 B2 | 8/2018 | Maimon et al. |
| 10,045,846 B2 | 8/2018 | Bonyuet et al. |
| 10,052,198 B2 | 8/2018 | Chau et al. |
| 10,052,199 B2 | 8/2018 | Spence et al. |
| 10,058,318 B2 | 8/2018 | Tegzes |
| 10,058,321 B2 | 8/2018 | Sampson et al. |
| 10,064,719 B2 | 9/2018 | Börtlein et al. |
| 10,070,954 B2 | 9/2018 | Braido et al. |
| 10,092,400 B2 | 10/2018 | Jimenez et al. |
| 10,098,734 B2 | 10/2018 | Hoang |
| 10,105,217 B2 | 10/2018 | Keränen |
| 10,105,224 B2 | 10/2018 | Buchbinder et al. |
| 10,130,464 B2 | 11/2018 | Meiri et al. |
| 10,130,471 B2 | 11/2018 | Keränen et al. |
| 10,143,552 B2 | 12/2018 | Wallace et al. |
| 10,149,759 B2 | 12/2018 | Naor |
| 10,172,708 B2 | 1/2019 | Anderson |
| 10,172,711 B2 | 1/2019 | Keränen |
| 10,179,042 B2 | 1/2019 | Braido et al. |
| 10,195,021 B2 | 2/2019 | Keränen et al. |
| 10,195,025 B2 | 2/2019 | Levi et al. |
| 10,195,027 B2 | 2/2019 | Nasr |
| 10,195,028 B2 | 2/2019 | Hosmer et al. |
| 10,195,029 B2 | 2/2019 | Keränen |
| 10,201,418 B2 | 2/2019 | Biadillah et al. |
| 10,206,775 B2 | 2/2019 | Kovalsky et al. |
| 10,213,307 B2 | 2/2019 | Dwork et al. |
| 10,226,330 B2 | 3/2019 | Spence et al. |
| 10,226,334 B2 | 3/2019 | Rowe et al. |
| 10,226,339 B2 | 3/2019 | Spence et al. |
| 10,238,489 B2 | 3/2019 | Conklin |
| 10,251,749 B2 | 4/2019 | Zerkowski et al. |
| 10,258,464 B2 | 4/2019 | Delaloye et al. |
| 10,258,468 B2 | 4/2019 | Deem et al. |
| 10,265,169 B2 | 4/2019 | Desrosiers et al. |
| 10,271,950 B2 | 4/2019 | Neustadter |
| 10,299,917 B2 | 5/2019 | Morriss et al. |
| 10,299,921 B2 | 5/2019 | Dale et al. |
| 10,321,988 B2 | 6/2019 | Gorman et al. |
| 10,321,989 B2 | 6/2019 | Keränen |
| 10,327,743 B2 | 6/2019 | St. Goar et al. |
| 10,327,766 B2 | 6/2019 | Zerkowski et al. |
| 10,335,277 B2 | 7/2019 | Crisostomo et al. |
| 10,338,724 B2 | 7/2019 | Zhao |
| 10,350,066 B2 | 7/2019 | Cooper et al. |
| 10,357,351 B2 | 7/2019 | Cooper et al. |
| 10,357,634 B2 | 7/2019 | Simmons et al. |
| 10,363,130 B2 | 7/2019 | Armer et al. |
| 10,363,131 B2 | 7/2019 | Eidenschink et al. |
| 10,368,986 B2 | 8/2019 | Gosal et al. |
| 10,368,990 B2 | 8/2019 | Noe et al. |
| 10,376,266 B2 | 8/2019 | Herman et al. |
| 10,376,360 B2 | 8/2019 | Bruchman et al. |
| 10,376,363 B2 | 8/2019 | Quadri et al. |
| 10,398,547 B2 | 9/2019 | Li et al. |
| 10,426,608 B2 | 10/2019 | Salahieh et al. |
| 10,433,961 B2 | 10/2019 | McLean |
| 10,470,881 B2 | 11/2019 | Noe et al. |
| 10,478,291 B2 | 11/2019 | Nguyen et al. |
| 10,500,048 B2 | 12/2019 | Khairkhahan et al. |
| 10,507,104 B2 | 12/2019 | Zhang et al. |
| 10,512,541 B2 | 12/2019 | Zerkowski et al. |
| 10,524,901 B2 | 1/2020 | Quadri et al. |
| 10,548,729 B2 | 2/2020 | Zipory et al. |
| 10,568,737 B2 | 2/2020 | Noe et al. |
| 10,575,951 B2 | 3/2020 | Johnson et al. |
| 10,603,165 B2 | 3/2020 | Maimon et al. |
| 10,639,154 B2 | 5/2020 | Seguin |
| 10,653,524 B2 | 5/2020 | Khairkhahan et al. |
| 10,660,753 B2 | 5/2020 | Pham et al. |
| 10,687,938 B2 | 6/2020 | Patel et al. |
| 10,695,160 B2 | 6/2020 | Lashinski et al. |
| 10,702,386 B2 | 7/2020 | Khairkhahan et al. |
| 10,709,552 B2 | 7/2020 | Backus et al. |
| 10,716,662 B2 | 7/2020 | Delaloye et al. |
| 10,722,352 B2 | 7/2020 | Spence |
| 10,722,353 B2 | 7/2020 | Levi |
| 10,722,359 B2 * | 7/2020 | Patel .................... A61F 2/2412 |
| 10,729,542 B2 | 8/2020 | Howard et al. |
| 10,743,991 B2 | 8/2020 | Brown |
| 10,751,180 B2 | 8/2020 | Schewel |
| 10,751,184 B2 | 8/2020 | Reich et al. |
| 10,765,514 B2 | 9/2020 | Iflah et al. |
| 10,813,749 B2 | 10/2020 | Nguyen et al. |
| 10,828,153 B2 | 11/2020 | Noe et al. |
| 10,856,970 B2 | 12/2020 | Tuval et al. |
| 10,869,755 B2 | 12/2020 | Granada et al. |
| 10,888,420 B2 | 1/2021 | Bateman et al. |
| 10,973,629 B2 | 4/2021 | Levi et al. |
| 10,973,630 B2 | 4/2021 | Torrianni et al. |
| 11,007,057 B2 | 5/2021 | Pham et al. |
| 11,020,221 B2 | 6/2021 | Arcaro et al. |
| 11,039,922 B2 | 6/2021 | Konno |
| 11,103,345 B2 | 8/2021 | Levi et al. |

(56) References Cited

U.S. PATENT DOCUMENTS

| | | |
|---|---|---|
| 2002/0173841 A1 | 11/2002 | Ortiz et al. |
| 2003/0114913 A1 | 6/2003 | Spenser et al. |
| 2003/0233142 A1 | 12/2003 | Morales et al. |
| 2004/0039442 A1 | 2/2004 | St. Goar et al. |
| 2004/0044350 A1 | 3/2004 | Martin et al. |
| 2005/0137686 A1 | 6/2005 | Salahieh et al. |
| 2005/0137687 A1 | 6/2005 | Salahieh et al. |
| 2005/0137691 A1 | 6/2005 | Salahieh et al. |
| 2005/0137694 A1 | 6/2005 | Haug et al. |
| 2005/0137696 A1 | 6/2005 | Salahich et al. |
| 2005/0165344 A1 | 7/2005 | Dobak, III |
| 2005/0277839 A1 | 12/2005 | Alderman et al. |
| 2006/0009841 A1 | 1/2006 | McGuckin, Jr. et al. |
| 2006/0052821 A1 | 3/2006 | Abbot et al. |
| 2006/0074484 A1 | 4/2006 | Huber |
| 2006/0178700 A1 | 8/2006 | Quinn |
| 2006/0217762 A1 | 9/2006 | Maahs et al. |
| 2006/0259136 A1 | 11/2006 | Nguyen et al. |
| 2006/0293698 A1 | 12/2006 | Douk |
| 2007/0055206 A1 | 3/2007 | To et al. |
| 2007/0118151 A1 | 5/2007 | Davidson |
| 2007/0142907 A1 | 6/2007 | Moaddeb et al. |
| 2007/0185572 A1 | 8/2007 | Solem et al. |
| 2007/0255396 A1 | 11/2007 | Douk et al. |
| 2007/0293724 A1 | 12/2007 | Saadat et al. |
| 2007/0293943 A1 | 12/2007 | Quinn |
| 2008/0004696 A1 | 1/2008 | Vesely |
| 2008/0004697 A1 | 1/2008 | Lichtenstein et al. |
| 2008/0200980 A1 | 8/2008 | Robin et al. |
| 2008/0208327 A1 | 8/2008 | Rowe |
| 2008/0275503 A1 | 11/2008 | Spence et al. |
| 2008/0275540 A1 | 11/2008 | Wen |
| 2009/0093826 A1 | 4/2009 | Warder-Gabaldon |
| 2009/0138079 A1 | 5/2009 | Tuval et al. |
| 2009/0209950 A1 | 8/2009 | Starksen |
| 2009/0222026 A1* | 9/2009 | Rothstein ........... A61B 17/0057 606/151 |
| 2009/0276040 A1 | 11/2009 | Rowe et al. |
| 2010/0010520 A1 | 1/2010 | Takahashi et al. |
| 2010/0049239 A1 | 2/2010 | McGuckin, Jr. et al. |
| 2010/0076497 A1 | 3/2010 | Zwirkoski |
| 2010/0094406 A1 | 4/2010 | Leprince et al. |
| 2010/0185172 A1 | 7/2010 | Fabro |
| 2010/0198056 A1 | 8/2010 | Fabro et al. |
| 2010/0198192 A1 | 8/2010 | Serina et al. |
| 2010/0198208 A1 | 8/2010 | Napp et al. |
| 2010/0217385 A1 | 8/2010 | Thompson et al. |
| 2010/0312333 A1* | 12/2010 | Navia ................... A61F 2/2418 623/2.36 |
| 2011/0022164 A1 | 1/2011 | Quinn et al. |
| 2011/0046600 A1 | 2/2011 | Crank |
| 2011/0224785 A1 | 9/2011 | Hacohen |
| 2011/0288637 A1 | 11/2011 | De Marchena |
| 2011/0313515 A1 | 12/2011 | Quadri et al. |
| 2011/0319989 A1 | 12/2011 | Lane et al. |
| 2012/0022633 A1 | 1/2012 | Olson et al. |
| 2012/0053680 A1 | 3/2012 | Bolling et al. |
| 2012/0143316 A1 | 6/2012 | Seguin et al. |
| 2012/0197388 A1 | 8/2012 | Khairkhahan et al. |
| 2012/0203333 A1 | 8/2012 | McGuckin, Jr. et al. |
| 2012/0221101 A1 | 8/2012 | Moaddeb et al. |
| 2012/0277853 A1 | 11/2012 | Rothstein |
| 2013/0006352 A1 | 1/2013 | Yaron |
| 2013/0023985 A1 | 1/2013 | Khairkhahan et al. |
| 2013/0035758 A1 | 2/2013 | Seguin et al. |
| 2013/0079873 A1 | 3/2013 | Migliazza et al. |
| 2013/0123912 A1 | 5/2013 | Tung et al. |
| 2013/0172992 A1 | 7/2013 | Gross et al. |
| 2013/0253643 A1 | 9/2013 | Rolando et al. |
| 2013/0274873 A1 | 10/2013 | Delaloye et al. |
| 2013/0325110 A1 | 12/2013 | Khalil et al. |
| 2014/0005768 A1 | 1/2014 | Thomas et al. |
| 2014/0031928 A1 | 1/2014 | Murphy et al. |
| 2014/0081154 A1 | 5/2014 | Toth |
| 2014/0200649 A1 | 7/2014 | Essinger et al. |
| 2014/0228943 A1 | 8/2014 | Stigall et al. |
| 2014/0249621 A1 | 9/2014 | Eidenschink |
| 2014/0257467 A1 | 9/2014 | Lane et al. |
| 2014/0324163 A1 | 10/2014 | Keränen et al. |
| 2015/0005764 A1 | 1/2015 | Hanson et al. |
| 2015/0018876 A1 | 1/2015 | Ewers et al. |
| 2015/0051709 A1 | 2/2015 | Vasquez et al. |
| 2015/0134055 A1 | 5/2015 | Spence et al. |
| 2015/0173897 A1 | 6/2015 | Raanani et al. |
| 2015/0250480 A1 | 9/2015 | Featherstone |
| 2015/0265403 A1 | 9/2015 | Keränen |
| 2015/0272737 A1 | 10/2015 | Dale et al. |
| 2015/0297346 A1 | 10/2015 | Duffy et al. |
| 2015/0305863 A1 | 10/2015 | Gray et al. |
| 2015/0328000 A1 | 11/2015 | Ratz et al. |
| 2015/0335290 A1 | 11/2015 | Hunter |
| 2015/0351735 A1 | 12/2015 | Keränen et al. |
| 2015/0351908 A1 | 12/2015 | Keränen et al. |
| 2015/0351911 A1 | 12/2015 | Keränen et al. |
| 2016/0089126 A1 | 3/2016 | Guo |
| 2016/0095705 A1 | 4/2016 | Keränen et al. |
| 2016/0113764 A1 | 4/2016 | Sheahan et al. |
| 2016/0143689 A1 | 5/2016 | Ditter |
| 2016/0143731 A1 | 5/2016 | Backus et al. |
| 2016/0166380 A1 | 6/2016 | Seguin et al. |
| 2016/0228247 A1 | 8/2016 | Maimon et al. |
| 2016/0235526 A1 | 8/2016 | Lashinski et al. |
| 2016/0235529 A1 | 8/2016 | Ma et al. |
| 2016/0324637 A1 | 11/2016 | Hlavka et al. |
| 2016/0324639 A1 | 11/2016 | Nguyen et al. |
| 2016/0331523 A1 | 11/2016 | Chau et al. |
| 2016/0346080 A1 | 12/2016 | Righini et al. |
| 2017/0056163 A1 | 3/2017 | Tayeb et al. |
| 2017/0079790 A1 | 3/2017 | Vidlund et al. |
| 2017/0112624 A1 | 4/2017 | Patel |
| 2017/0119524 A1 | 5/2017 | Salahieh et al. |
| 2017/0128203 A1 | 5/2017 | Zhang et al. |
| 2017/0156723 A1 | 6/2017 | Keating et al. |
| 2017/0165057 A9 | 6/2017 | Morriss et al. |
| 2017/0189177 A1 | 7/2017 | Schweich et al. |
| 2017/0216025 A1 | 8/2017 | Nitzan et al. |
| 2017/0245850 A1 | 8/2017 | Call et al. |
| 2017/0258585 A1 | 9/2017 | Marquez et al. |
| 2017/0273788 A1 | 9/2017 | O'Carroll et al. |
| 2017/0273789 A1 | 9/2017 | Yaron et al. |
| 2017/0281341 A1 | 10/2017 | Lim et al. |
| 2017/0311937 A1 | 11/2017 | Bambury et al. |
| 2017/0348099 A1 | 12/2017 | Mendelson et al. |
| 2018/0049873 A1 | 2/2018 | Manash et al. |
| 2018/0055628 A1 | 3/2018 | Patel et al. |
| 2018/0092763 A1 | 4/2018 | Dagan et al. |
| 2018/0110622 A1 | 4/2018 | Gregg et al. |
| 2018/0116790 A1 | 5/2018 | Ratz et al. |
| 2018/0133003 A1 | 5/2018 | Levi |
| 2018/0177592 A1 | 6/2018 | Benichou et al. |
| 2018/0177594 A1 | 6/2018 | Patel et al. |
| 2018/0206982 A1 | 7/2018 | Haivatov et al. |
| 2018/0206986 A1 | 7/2018 | Noe et al. |
| 2018/0206992 A1 | 7/2018 | Brown |
| 2018/0207395 A1 | 7/2018 | Bulman et al. |
| 2018/0214267 A1 | 8/2018 | Lally et al. |
| 2018/0214270 A1 | 8/2018 | Subramanian et al. |
| 2018/0221014 A1 | 8/2018 | Darabian |
| 2018/0228608 A1 | 8/2018 | Sheps et al. |
| 2018/0228610 A1 | 8/2018 | Lashinski et al. |
| 2018/0235443 A1 | 8/2018 | Smith et al. |
| 2018/0250126 A1 | 9/2018 | O'Connor et al. |
| 2018/0250132 A1 | 9/2018 | Ketai et al. |
| 2018/0263764 A1 | 9/2018 | Manash et al. |
| 2018/0289473 A1 | 10/2018 | Rajagopal et al. |
| 2018/0289474 A1 | 10/2018 | Rajagopal et al. |
| 2018/0289478 A1 | 10/2018 | Quill |
| 2018/0289480 A1 | 10/2018 | D'Ambra et al. |
| 2018/0289485 A1 | 10/2018 | Rajagopal et al. |
| 2018/0296335 A1 | 10/2018 | Miyashiro |
| 2018/0296338 A1 | 10/2018 | Rabito et al. |
| 2018/0318079 A1 | 11/2018 | Patel et al. |
| 2018/0333259 A1 | 11/2018 | Dibie |
| 2018/0344303 A1 | 12/2018 | Bambury et al. |

(56) References Cited

U.S. PATENT DOCUMENTS

| | | |
|---|---|---|
| 2018/0344454 A1 | 12/2018 | Mauch et al. |
| 2018/0344459 A1 | 12/2018 | Spence et al. |
| 2018/0360600 A1 | 12/2018 | Zhuang et al. |
| 2018/0368830 A1 | 12/2018 | O'Carroll et al. |
| 2019/0000625 A1 | 1/2019 | O'Carroll et al. |
| 2019/0008635 A1 | 1/2019 | Francis et al. |
| 2019/0008639 A1 | 1/2019 | Landon et al. |
| 2019/0008640 A1 | 1/2019 | Cooper et al. |
| 2019/0015205 A1 | 1/2019 | Rajagopal et al. |
| 2019/0021859 A1 | 1/2019 | O'Carrol et al. |
| 2019/0046315 A1 | 2/2019 | Gao et al. |
| 2019/0053894 A1 | 2/2019 | Levi et al. |
| 2019/0053895 A1 | 2/2019 | Levi |
| 2019/0053898 A1 | 2/2019 | Maimon et al. |
| 2019/0053899 A1 | 2/2019 | Levi |
| 2019/0053903 A1 | 2/2019 | Rohl et al. |
| 2019/0060068 A1 | 2/2019 | Cope et al. |
| 2019/0060069 A1 | 2/2019 | Maimon et al. |
| 2019/0060071 A1 | 2/2019 | Lane et al. |
| 2019/0076244 A1 | 3/2019 | Yohanan et al. |
| 2019/0076664 A1 | 3/2019 | Ollivier |
| 2019/0117392 A1 | 4/2019 | Quadri et al. |
| 2019/0133756 A1 | 5/2019 | Zhang et al. |
| 2019/0133757 A1 | 5/2019 | Zhang et al. |
| 2019/0142589 A1 | 5/2019 | Basude |
| 2019/0159770 A1 | 5/2019 | Rohl et al. |
| 2019/0160292 A1 | 5/2019 | Peichel et al. |
| 2019/0167425 A1 | 6/2019 | Reich et al. |
| 2019/0183649 A1 | 6/2019 | Allen et al. |
| 2019/0192296 A1 | 6/2019 | Schwartz et al. |
| 2019/0201191 A1 | 7/2019 | McLean et al. |
| 2019/0209311 A1 | 7/2019 | Zhang et al. |
| 2019/0209312 A1 | 7/2019 | Zhang et al. |
| 2019/0209313 A1 | 7/2019 | Zhang et al. |
| 2019/0209314 A1 | 7/2019 | Zhang et al. |
| 2019/0209315 A1 | 7/2019 | Zhang et al. |
| 2019/0209316 A1 | 7/2019 | Zhang et al. |
| 2019/0209317 A1 | 7/2019 | Zhang et al. |
| 2019/0209318 A1 | 7/2019 | Zhang et al. |
| 2019/0209320 A1 | 7/2019 | Drasler et al. |
| 2019/0231520 A1 | 8/2019 | Desrosiers et al. |
| 2019/0240023 A1 | 8/2019 | Spence et al. |
| 2019/0246916 A1 | 8/2019 | Kuraguntla et al. |
| 2019/0254816 A1 | 8/2019 | Anderson et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0262129 A1 | 8/2019 | Cooper et al. |
| 2019/0282237 A1 | 9/2019 | Goldfarb et al. |
| 2019/0328518 A1 | 10/2019 | Neumann |
| 2019/0336282 A1 | 11/2019 | Christianson et al. |
| 2019/0343625 A1 | 11/2019 | Gharib et al. |
| 2019/0365530 A1 | 12/2019 | Hoang et al. |
| 2019/0374337 A1 | 12/2019 | Zamani et al. |
| 2019/0374342 A1 | 12/2019 | Gregg et al. |
| 2020/0000579 A1 | 1/2020 | Manash et al. |
| 2020/0000586 A1 | 1/2020 | Tian et al. |
| 2020/0008936 A1 | 1/2020 | Cheema et al. |
| 2020/0022811 A1 | 1/2020 | Griswold et al. |
| 2020/0054453 A1 | 2/2020 | Zerkowski et al. |
| 2020/0060813 A1 | 2/2020 | Nguyen et al. |
| 2020/0060820 A1 | 2/2020 | Ben-Zvi et al. |
| 2020/0060852 A1 | 2/2020 | Argento et al. |
| 2020/0078000 A1 | 3/2020 | Rajagopal et al. |
| 2020/0093601 A1 | 3/2020 | Neustadter |
| 2020/0107932 A1 | 4/2020 | Rabito et al. |
| 2020/0107933 A1 | 4/2020 | Oba |
| 2020/0113586 A1 | 4/2020 | Karasic et al. |
| 2020/0113685 A1 | 4/2020 | Miller et al. |
| 2020/0113696 A1 | 4/2020 | Ekvall et al. |
| 2020/0138575 A1 | 5/2020 | Tuval |
| 2020/0178977 A1 | 6/2020 | Coleman et al. |
| 2020/0188107 A1 | 6/2020 | Gloss et al. |
| 2020/0205800 A1 | 7/2020 | Gilmore et al. |
| 2020/0205969 A1 | 7/2020 | Hacohen |
| 2020/0205974 A1 | 7/2020 | Zerkowski et al. |
| 2020/0205975 A1 | 7/2020 | Khairkhahan |
| 2020/0205979 A1 | 7/2020 | O'Carroll et al. |
| 2020/0214708 A1 | 7/2020 | Sharma |
| 2020/0229806 A1 | 7/2020 | Goldfarb et al. |
| 2020/0229918 A1 | 7/2020 | Pham et al. |
| 2020/0275921 A1 | 9/2020 | Gilmore et al. |
| 2020/0276017 A1 | 9/2020 | Subramanian et al. |
| 2020/0297489 A1 | 9/2020 | Bishop et al. |
| 2020/0352705 A1 | 11/2020 | Heneghan et al. |
| 2020/0352706 A1 | 11/2020 | Campbell |
| 2020/0360139 A1 | 11/2020 | Hammer et al. |
| 2021/0022854 A1 | 1/2021 | Zhao et al. |
| 2021/0022860 A1 | 1/2021 | Lally et al. |
| 2021/0030536 A1 | 2/2021 | Kaleta |
| 2021/0121289 A1 | 4/2021 | Bruchman et al. |
| 2021/0128297 A1 | 5/2021 | Braido et al. |
| 2021/0145573 A1 | 5/2021 | Dasi et al. |
| 2021/0154009 A1 | 5/2021 | Argento et al. |
| 2021/0161688 A1 | 6/2021 | Shahriar |
| 2021/0177583 A1 | 6/2021 | Colavito et al. |
| 2021/0177584 A1 | 6/2021 | Levi et al. |
| 2021/0177587 A1 | 6/2021 | Braido |
| 2021/0186689 A1 | 6/2021 | Eidenschink et al. |
| 2021/0228343 A1 | 7/2021 | Scheinblum et al. |
| 2022/0054261 A1 | 2/2022 | Argento et al. |

FOREIGN PATENT DOCUMENTS

| | | |
|---|---|---|
| AU | 2020227034 A1 | 9/2020 |
| BR | PI0820603 B1 | 6/2020 |
| CA | 2979817 A1 | 9/2020 |
| CA | 2954826 C | 10/2019 |
| CN | 103764216 A | 4/2014 |
| CN | 103974670 A | 8/2014 |
| CN | 105358098 A | 2/2016 |
| CN | 111110401 A | 5/2020 |
| CN | 108601655 B | 6/2020 |
| CN | 111265335 A | 6/2020 |
| CN | 111278389 A | 6/2020 |
| CN | 111329541 A | 6/2020 |
| DE | 19857887 B4 | 5/2005 |
| EP | 1432369 B1 | 2/2008 |
| EP | 2374415 A1 | 10/2011 |
| EP | 2907479 A1 | 8/2015 |
| EP | 3037064 A1 | 6/2016 |
| EP | 3342355 A1 | 7/2018 |
| EP | 3395296 A1 | 10/2018 |
| EP | 3406225 A1 | 11/2018 |
| EP | 3417831 A1 | 12/2018 |
| EP | 3476366 A1 | 5/2019 |
| EP | 3482718 A1 | 5/2019 |
| EP | 2637607 B1 | 10/2019 |
| EP | 3554424 A1 | 10/2019 |
| EP | 3244809 B1 | 2/2020 |
| EP | 3639792 A1 | 4/2020 |
| EP | 3417831 B1 | 5/2020 |
| EP | 3649963 A2 | 5/2020 |
| EP | 2072027 B1 | 6/2020 |
| EP | 3441045 B1 | 7/2020 |
| EP | 3672528 A1 | 7/2020 |
| EP | 3554423 B1 | 8/2020 |
| EP | 3107498 B1 | 9/2020 |
| EP | 3570782 B1 | 9/2020 |
| EP | 3700467 A1 | 9/2020 |
| EP | 3705090 A1 | 9/2020 |
| EP | 3782585 A1 | 2/2021 |
| JP | H08131551 A | 5/1996 |
| JP | 2004154177 A | 6/2004 |
| JP | 2008018139 A | 1/2008 |
| JP | 2012531270 A | 12/2012 |
| JP | 2020515375 A | 5/2020 |
| JP | 2020517379 A | 6/2020 |
| JP | 2020520729 A | 7/2020 |
| JP | 6735294 B2 | 8/2020 |
| KR | 2020032237 A | 3/2020 |
| KR | 2020033349 A | 3/2020 |
| KR | 2020033350 A | 3/2020 |
| TW | 202027694 A | 8/2020 |

(56) References Cited

FOREIGN PATENT DOCUMENTS

| | | |
|---|---|---|
| WO | WO2007/007873 A1 | 1/2007 |
| WO | WO2007/081820 A1 | 7/2007 |
| WO | WO2010/141847 A1 | 12/2010 |
| WO | WO2011/025945 A1 | 3/2011 |
| WO | WO2012/145545 A1 | 10/2012 |
| WO | WO2013/190910 A1 | 12/2013 |
| WO | WO2015/127264 A1 | 8/2015 |
| WO | WO2015/195823 A1 | 12/2015 |
| WO | WO2016/052145 A1 | 4/2016 |
| WO | WO2016/117169 A1 | 7/2016 |
| WO | WO2016/183485 A1 | 11/2016 |
| WO | WO2017/121193 A1 | 7/2017 |
| WO | WO2017/151566 A1 | 9/2017 |
| WO | WO2017/214098 A1 | 12/2017 |
| WO | WO2018/039561 A1 | 3/2018 |
| WO | WO2018/039589 A1 | 3/2018 |
| WO | WO2018/112429 A1 | 6/2018 |
| WO | WO2018/119304 A1 | 6/2018 |
| WO | WO2018/178966 A1 | 10/2018 |
| WO | WO2018/178967 A1 | 10/2018 |
| WO | WO2018/187390 A1 | 10/2018 |
| WO | WO2018/192197 A1 | 10/2018 |
| WO | WO2019/010370 A1 | 1/2019 |
| WO | WO2019/036592 A1 | 2/2019 |
| WO | WO2019/062366 A1 | 4/2019 |
| WO | WO2019/081777 A1 | 5/2019 |
| WO | WO2019/086958 A1 | 5/2019 |
| WO | WO2019/102484 A1 | 5/2019 |
| WO | WO2019/116369 A1 | 6/2019 |
| WO | WO2019/118371 A1 | 6/2019 |
| WO | WO2019/135011 A1 | 7/2019 |
| WO | WO2019/135028 A1 | 7/2019 |
| WO | WO2019/144036 A1 | 7/2019 |
| WO | WO2019/147504 A1 | 8/2019 |
| WO | WO2019/147846 A2 | 8/2019 |
| WO | WO2019/154124 A1 | 8/2019 |
| WO | WO2019/164516 A1 | 8/2019 |
| WO | WO2019/195860 A2 | 10/2019 |
| WO | WO2019/209927 A1 | 10/2019 |
| WO | WO2019/222694 A1 | 11/2019 |
| WO | WO2019/241777 A1 | 12/2019 |
| WO | WO2020/051147 A1 | 3/2020 |
| WO | WO2020/051591 A1 | 3/2020 |
| WO | WO2020/072199 A1 | 4/2020 |
| WO | WO2020/072201 A1 | 4/2020 |
| WO | WO2020/073050 A1 | 4/2020 |
| WO | WO2020/082039 A1 | 4/2020 |
| WO | WO2020/123719 A1 | 6/2020 |
| WO | WO2020/157018 A1 | 8/2020 |
| WO | WO2020/163112 A1 | 8/2020 |
| WO | WO2020/210685 A8 | 10/2020 |
| WO | WO2020/236830 A1 | 11/2020 |
| WO | WO2020/247907 A1 | 12/2020 |
| WO | WO2021/021482 A1 | 2/2021 |
| WO | WO2021/028867 A1 | 2/2021 |
| WO | WO2021/034497 A1 | 2/2021 |
| WO | WO2021/086850 A1 | 5/2021 |
| WO | WO2021/087400 A1 | 5/2021 |
| WO | WO2021/091754 A1 | 5/2021 |
| WO | WO2021/113143 A1 | 6/2021 |
| WO | WO2022/174160 A1 | 8/2022 |

OTHER PUBLICATIONS

Argento et al.; U.S. Appl. No. 16/594,946 entitled "Prosthetic cardiac valve devices, systems, and methods," filed Oct. 7, 2019.

Argento et al.; U.S. Appl. No. 16/824,576 entitled "Prosthetic cardiac valve devices, systems, and methods," filed Mar. 19, 2020.

Argento et al.; U.S. Appl. No. 17/286,724 entitled "Adjustable medical device," filed Apr. 19, 2021.

Salahieh et al.; U.S. Appl. No. 17/543,555 entitled "Flared prosthetic cardiac valve delivery devices and systems," filed Dec. 6, 2021.

Yang et al.; U.S. Appl. No. 17/651,040 entitled "Anchor for prosthetic cardiac valve delivery devices and systems".

Salahieh.; U.S. Appl. No. 17/655,978 entitled "Anchor position verification for prosthetic cardiac valve devices," filed Mar. 22, 2022.

Saul; U.S. Appl. No. 17/773,193 entitled "Prosthetic cardiac valve delivery devices, systems, and methods," filed Apr. 29, 2022.

* cited by examiner anterior (aortic) leaflet
anterolateral commissure
posteromedial commissure
posterior (mural) leaflet

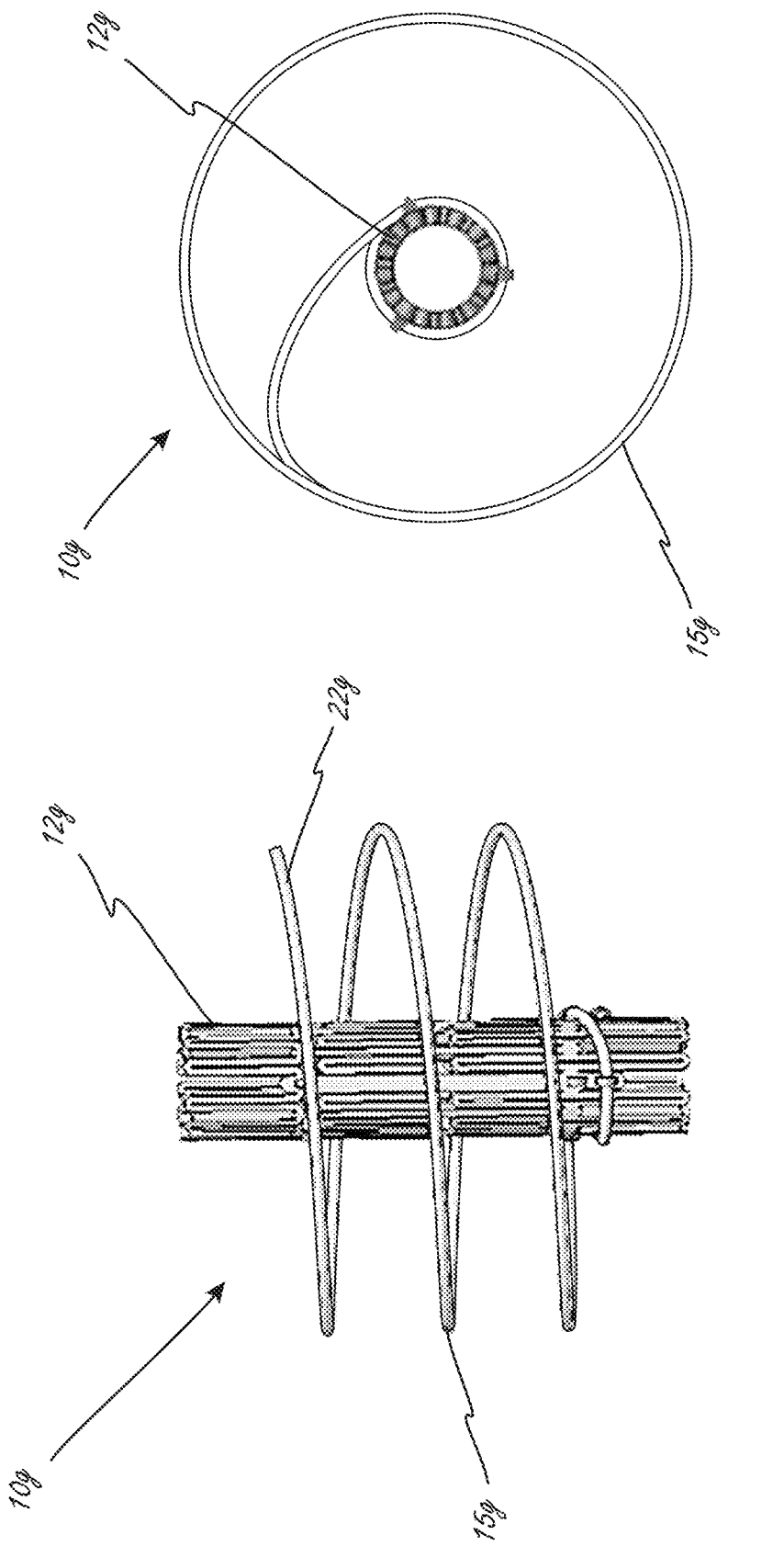

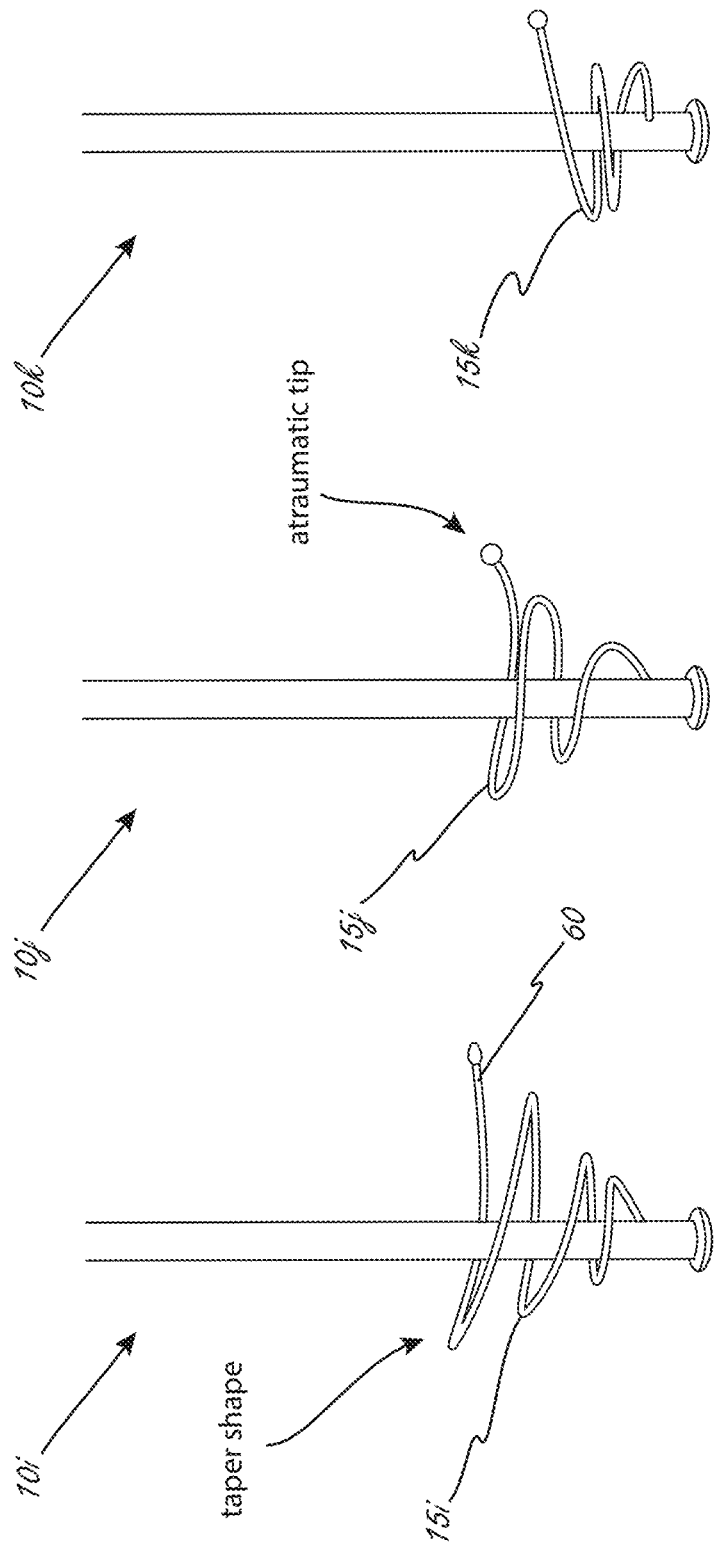

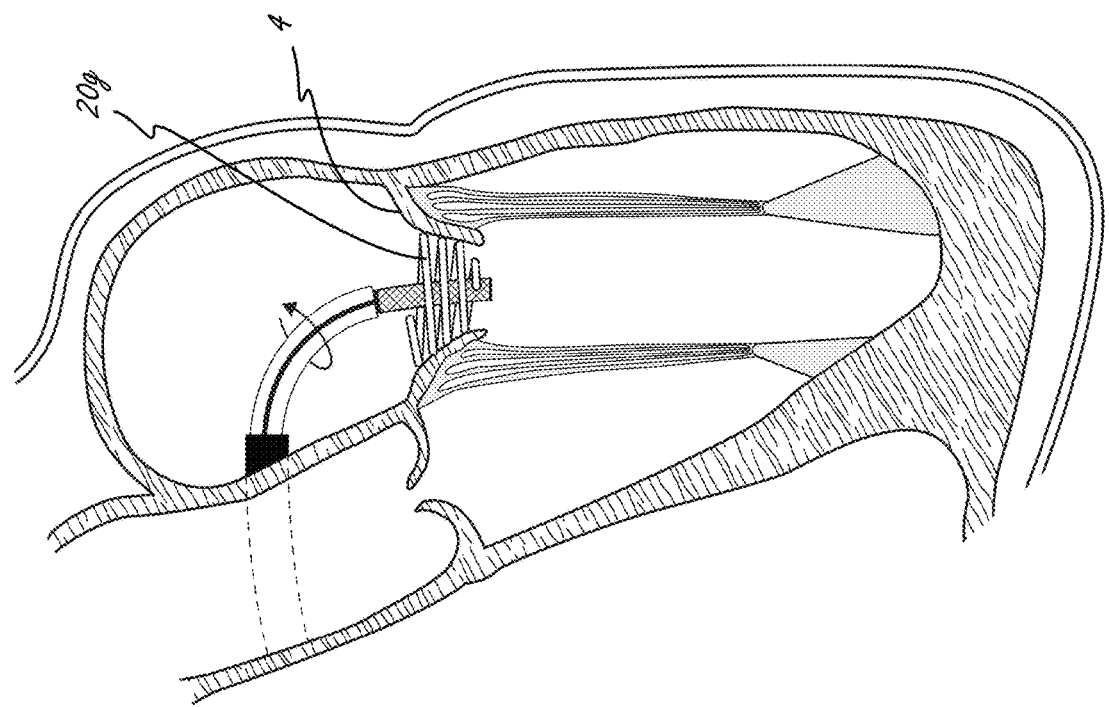
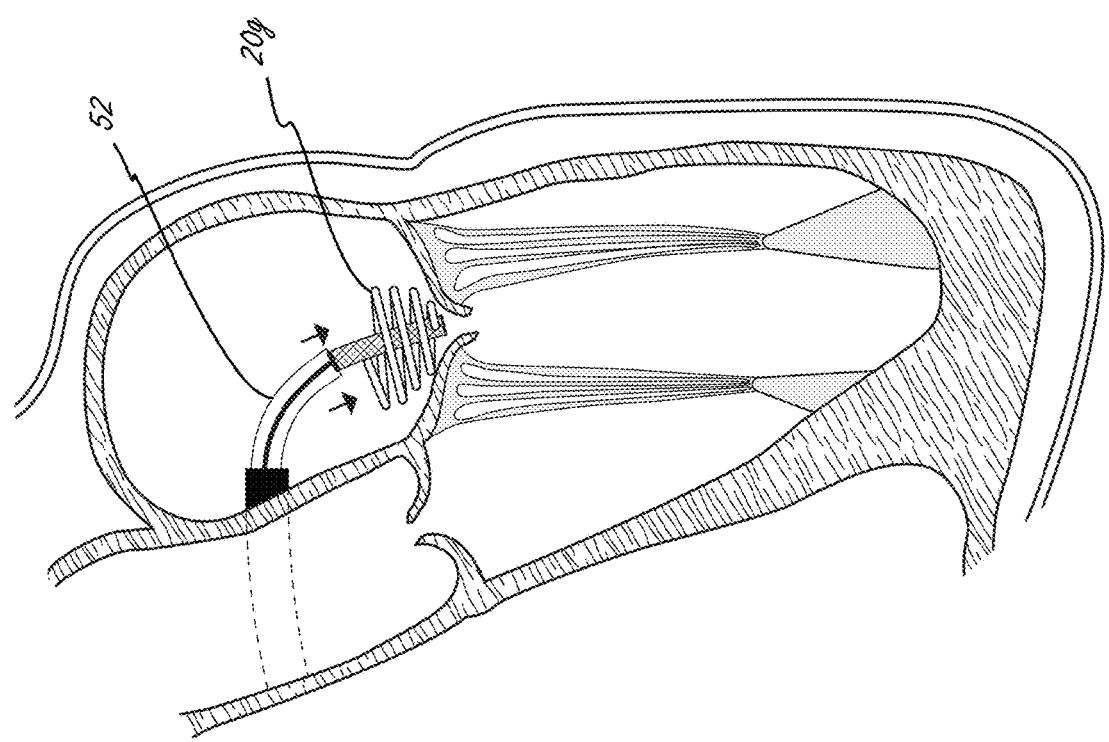

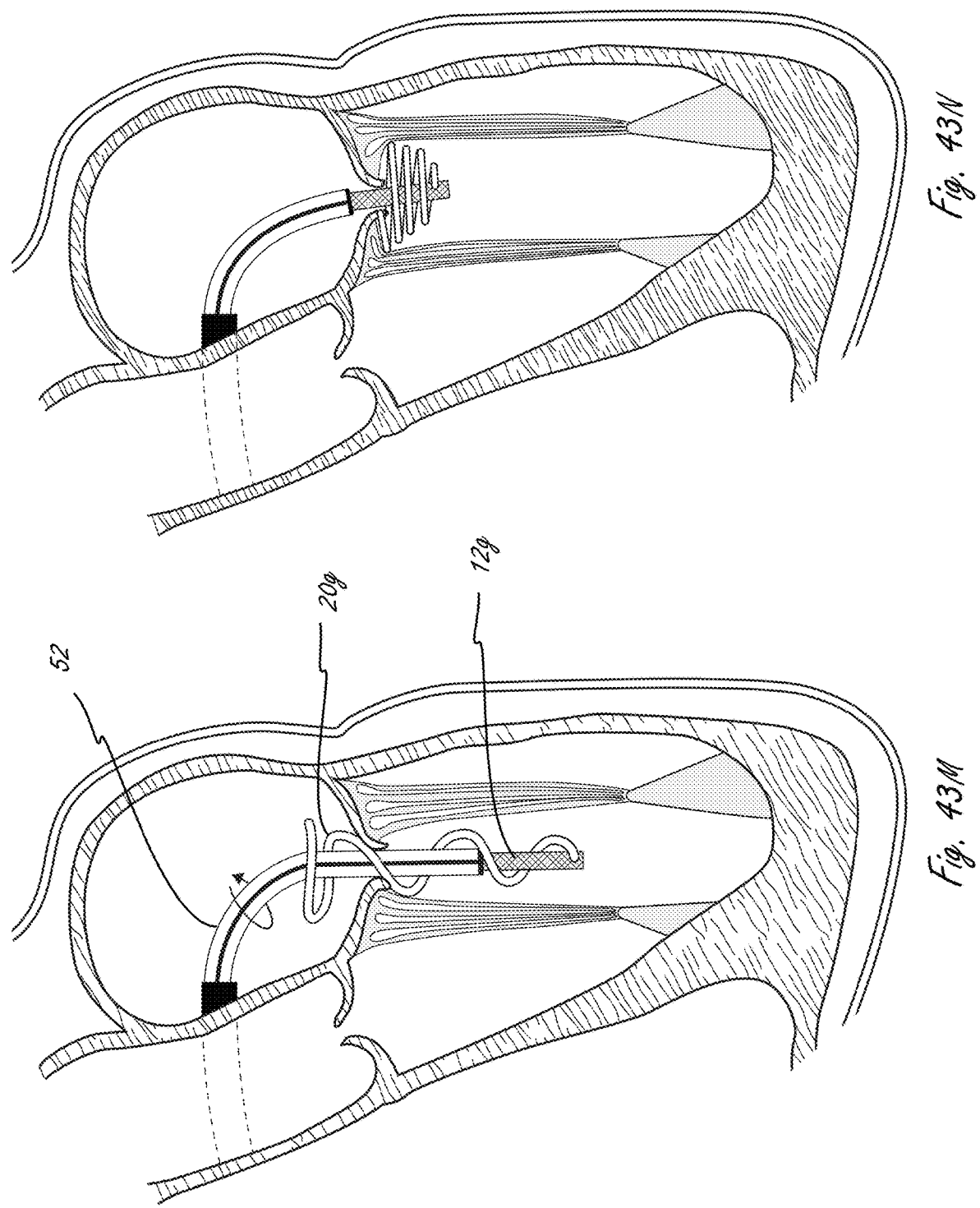

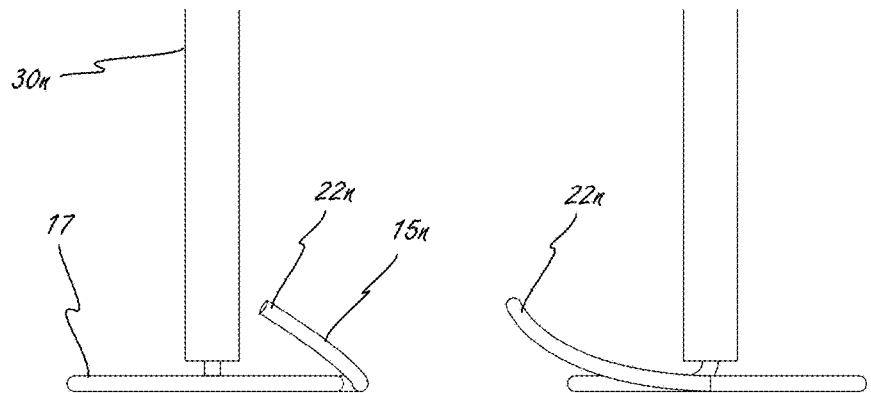
Fig. 63
Fig. 64
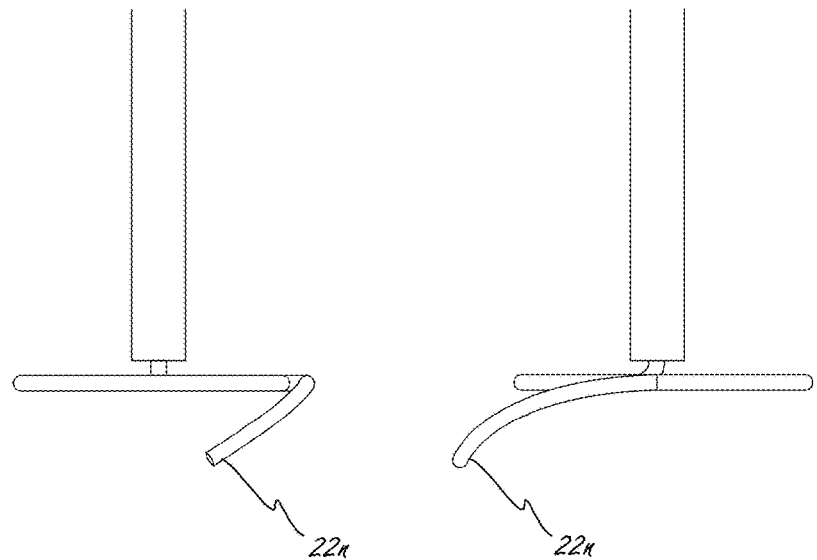
Fig. 65
Fig. 66

PROSTHETIC CARDIAC VALVE DEVICES, SYSTEMS, AND METHODS

CROSS-REFERENCE

This application claims the benefit of U.S. Provisional Application No. 62/784,280, filed Dec. 21, 2018, entitled "Prosthetic Cardiac Valve Devices, Systems, and Methods"; U.S. Provisional Application No. 62/815,791, filed Mar. 8, 2019, entitled "Prosthetic Cardiac Valve Devices, Systems, and Methods"; and U.S. Provisional Application No. 62/851,245, filed May 22, 2019, entitled "Prosthetic Cardiac Valve Devices, Systems, and Methods"; which are incorporated herein by reference for all purposes in their entireties.

BACKGROUND

Blood flow between and out of heart chambers is regulated by native valves—the mitral valve, the aortic valve, the pulmonary valve, and the tricuspid valve. Each of these valves are passive one-way valves which open and close in response to differential pressures. Patients with valvular disease have abnormal anatomy and/or function of at least one valve. For example, a valve may suffer from insufficiency, also referred to as regurgitation, when the valve does not fully close and allows blood to flow retrograde. Valve stenosis can cause a valve to fail to open properly. Other diseases may also lead to dysfunction of the valves. While medications may be used to treat the disease, in many cases the defective valve may need to be repaired or replaced at some point during the patient's lifetime. Existing valves and surgical repair and/or replacement procedures may have increased risks, limited lifespans, and/or are highly invasive. Some less-invasive transcatheter options are available, however these generally are limited to aortic valve procedures, are limited in their patient-to-patient flexibility, and often take longer than desired to implant.

Referring to FIGS. 1 and 2, the heart 2 includes four chambers connected by four valves. The upper part of the heart 2 includes the left atrium 25 and right atrium 5. The lower part includes the left ventricle 26 and right ventricle 6. The heart 2 and cardiovascular system operates like a closed circuit. The right side of the heart 2 receives de-oxygenated blood from the body and delivers the blood through the pulmonary artery 7 to the lungs where it becomes re-oxygenated. The oxygenated blood is returned to the left side of the heart 2, referred to as the systemic side, which delivers the oxygenated blood throughout the body.

Blood flow between the heart chambers is regulated by the valves. On the left side of the heart, the mitral valve 4 is located between the left atrium 25 and the left ventricle 26 and the aortic valve 9 is located between the left ventricle 26 and the aorta 1. On the right side of the heart 2, the pulmonary valve 3 is located between the right ventricle 6 and the pulmonary artery 7 and the tricuspid valve 8 is located between the right ventricle 6 and the right atrium 5.

All four of heart valves are passive one-way valves with "leaflets" which open and close in response to differential pressures. For example, in a healthy heart during systole the left ventricle 26 contracts and pushes blood out the aortic valve 9. In turn, the pressure in the left ventricle 26 causes the mitral valve 4 to close thereby preventing blood from going back into the left atrium 25 during systole.

A significant population will acquire valve disease in their lifetime. Congenital heart disease is also a significant problem. Patients with valvular disease have abnormal anatomy and/or function of at least one valve. Congenital valve abnormalities may be tolerated and/or treated palliatively for some years before developing into a life-threatening problem in later years. However, congenital heart disease may present life-threatening risk without notice. Patients may acquire valvular disease from rheumatic fever, heart failure, degenerative leaflet tissue, bacterial infection, and more.

Valvular disease may be caused by several factors as shown in FIGS. 3 to 5. FIG. 3 shows a healthy mitral valve 4. Referring to FIGS. 4 to 5 show a diseased mitral valve 4. The valve 4 in FIG. 4 suffers from insufficiency, also referred to as regurgitation. Such a valve 4 does not fully close and allows blood to flow retrograde. In this case, blood will flow back into the left atrium 25 during systole. FIG. 5 shows a mitral valve 4 with stenosis. Such a valve 4 does not open properly. Some valves 4 can have concomitant insufficiency and stenosis. Other diseases may also be present, such as Barlow's disease, which prevent the valve 4 from functioning properly. These diseases reduce cardiac output and force the heart 2 to work harder, thus increasing the risk of heart failure and chordae failures.

While medications may be used to treat the disease, in many cases the defective valve may need to be repaired or replaced at some point during the patient's lifetime. The native valve can be replaced with a mechanical valve or tissue valve. Mechanical valves have a disc or other member which opens and closes. Although mechanical valves are formed of biocompatible materials, they carry an increased risk of clotting. Thus, patients usually need to take anticoagulants for the remainder of their lives, which presents additional complications. Tissue valves can be formed of human or animal tissue, as well as polymeric materials. Tissue valves, unlike mechanical valves, do not typically require long-term use of anti-coagulants, but because they are formed of a living tissue they are not as widely available nor do they last as long as mechanical valves. Common tissue valves include porcine aortic valves mounted within a stent-like structure.

More recently there has been increased interest in less invasive procedures for implantation of prosthetic valves. One type of percutaneous procedure involves using a catheter to place a prosthetic valve inside of a diseased or injured heart valve.

Existing percutaneous procedures for valve repair still face many challenges. These challenges have limited the adoption of transcatheter procedures to certain patient populations and anatomies. Thus far, transcatheter devices are largely focused on aortic valve procedures and the sickest patient populations who may not be able to tolerate surgery. There is a continuing need for improved transcatheter devices which meet or exceed the performance and safety of surgical valves. Percutaneous valve replacement has also been limited to aortic valve procedures. While a large segment of the population suffers from tricuspid and mitral valve disease, the anatomy and function of these valves present challenges to transcatheter replacement. The aortic valve can be accessed via the femoral artery whereas the mitral valve, for example, typically requires a transseptal approach. The mitral valve anatomy presents more complexities to transcatheter procedures than the aortic valve. For example, as shown in FIG. 4, the mitral valve 4 includes two asymmetrical leaflets 4a, 4b and an irregularly-shaped annulus 4c. The mitral valve 4 also varies far more considerably patient-to-patient than the aortic valve. For these and other reasons, surgical replacement and percutaneous repair thus far are the only widely-available commercial treatments for mitral valve disease.

There is a continuing need to provide improved less invasive procedures for repair and replacement of heart valves. There is a continuing need to provide less invasive procedures for replacement of diseased valves, including the mitral valve.

There is a continuing need to be able to be able to provide a variety of different valve assemblies to accommodate the requirements of different patients, such as by providing prosthetic valves that can accommodate a variety of individual patients.

Furthermore, existing valve repair/replacement procedures are often complicated and time-consuming. Currently available procedures often require the placement of more than one component—for example, a prosthetic valve and a mechanism to anchor it to the native anatomy. Such procedures generally utilize multiple delivery catheters to carry the various components and delivery of each component separately to the valve, which can be time-consuming (particularly if components are delivered sequential), complicated, and/or dangerous. For example, some devices provide rotational anchoring elements to capture the native anatomy such as the chordae tendineae in order to reduce delivery time. However, such anchoring elements, often by design, capture and pull the chordae along during their rotation, which can torque or otherwise stress and damage the chordae during deployment of the anchor elements, resulting in the need for additional medical interventions for the patient. It would therefore be desirable to provide quicker, less-complicated, and less dangerous valve assemblies and procedures for valvular replacement and repair.

SUMMARY

It would therefore be desirable to provide a less invasive procedure for repair and replacement of heart valves, including the mitral valve, quicker surgical methods, and/or prosthetic valves that can accommodate a variety of individual patients. Not necessarily all such aspects or advantages are achieved by any particular embodiment. Thus, various embodiments may be carried out in a manner that achieves or optimizes one advantage or group of advantages taught herein without necessarily achieving other aspects or advantages as may also be taught or suggested herein.

The present disclosure generally relates to treating a diseased native valve in a patient and more particularly relates to prosthetic heart valves.

The present disclosure relates to prosthetic cardiac devices, and in some embodiments, prosthetic heart valves such as catheter-based mitral valves.

An aspect of the present disclosure provides a system for treating a diseased native valve in a patient. The system comprises a frame structure having an unexpanded configuration and an expanded configuration and an anchor comprising a free end and having a flat spiral shape. The frame structure is configured to be actuated from the unexpanded configuration to the expanded configuration adjacent a native valve in a patient. The anchor is configured to anchor the frame structure to the native valve when the frame structure is in the expanded configuration adjacent the native valve.

In some embodiments, the anchor may be configured to be fully advanced from an atrial side of the native valve into a ventricle of the heart. In some embodiments, at least a portion of the anchor may be configured to reside in a subvalvular plane of the heart when it anchors the frame structure to the native valve. In some embodiments, the anchor may be configured to reside entirely within the subvalvular plane of the heart when it anchors the frame structure to the native valve.

In some embodiments, the anchor may comprise a delivery configuration and a deployed configuration. The anchor may comprise the flat spiral shape in the deployed configuration. Alternatively, or in combination, the anchor may comprise an elongated shape in the delivery configuration. The anchor may be configured to be actuated from the delivery configuration to the deployed configuration adjacent a native valve in a patient. In some embodiments, the anchor may comprise one or more locking mechanisms configured to maintain the anchor in the deployed configuration. The one or more locking mechanisms may comprise a frictional band, a polymer coating, or one or more key and one or more key hole features. In some embodiments, the anchor may comprise a first loop, a second loop, and the one or more locking mechanisms may be configured to couple the first loop to the second loop when the anchor is in the deployed configuration. In some embodiments, the one or more locking mechanisms may comprise a first feature disposed on a first loop of the anchor and a correspondingly-shaped second feature disposed on a second loop of the anchor. The first and second features may be configured to nest with one another when the anchor is in the deployed configuration.

Alternatively, or in combination, the deployed configuration may comprise an intermediate deployed configuration and a fully deployed configuration. The anchor may be configured to be actuated from the intermediate deployed configuration to the fully deployed configuration adjacent a native valve in a patient. In some embodiments, an outer perimeter of the flat spiral shape may be the same in the intermediate deployed configuration and the fully deployed configuration. In some embodiments, the anchor may comprise a first loop, a second loop, and one or more locking mechanisms. The one or more locking mechanisms may be configured to couple the first loop to the second loop when the anchor is in the fully deployed configuration.

In some embodiments, the system may further comprise a delivery device. The delivery device may comprise an outer sheath. The anchor may be disposed in a lumen of the outer sheath and maintained in the delivery configuration by radial constriction from the outer sheath. Advancement of the anchor out of the lumen of the outer sheath may actuate the anchor into the deployed configuration. The delivery device may further comprise an inner shaft. The inner shaft may be disposed within the lumen of the outer sheath. In some embodiments, a proximal portion of the frame structure may be coupled to a distal portion of the inner shaft. In some embodiments, a proximal end of the anchor may be coupled to a distal portion of the inner shaft. In some embodiments, advancement of the inner shaft towards an opening of the lumen of the outer sheath may advance the anchor out of the lumen of the outer shaft and actuate the anchor into the deployed configuration. Alternatively, or in combination, the frame structure may be maintained in the unexpanded configuration by radial constriction from the outer sheath and advancement of the inner shaft out of the lumen of the outer sheath may actuate the frame structure into the expanded configuration. In some embodiments, the delivery device may further comprise guidewire disposed within a lumen of the inner shaft. In some embodiments, the outer sheath may be steerable. In some embodiments, the anchor may be configured to wrap at least partially around the inner shaft in the deployed configuration. In some embodiments, a central point of the flat spiral shape may be co-axial with a longitudinal axis of the inner shaft when the anchor is in the deployed configuration. In some embodiments, the frame structure may be detachably coupled to the delivery device in the unexpanded configuration during delivery to the native valve. In some embodiments, expansion of the frame structure to the expanded configuration may detach the frame structure from the delivery device.

In some embodiments, a proximal end of the anchor may be coupled to a distal end of the frame structure.

In some embodiments, the flat spiral shape may comprise a one or more loops. The one or more loops may comprise at least 360 degrees of rotation. For example, the one or more loops may comprise about 540 degrees of rotation.

In some embodiments, the flat spiral shape may comprise a plurality of loops. The anchor may comprise one or more spaces between the plurality of loops. Alternatively, or in combination, the plurality of loops may spiral radially outward from a central point.

In some embodiments, the anchor may comprise a super-elastic material. For example, the anchor may comprise nitinol.

In some embodiments, the frame structure may comprise an expandable stent.

In some embodiments, the expanded configuration may be a generally tubular expanded shape.

In some embodiments, the frame structure may comprise an expanded outer periphery in the expanded configuration and a compressed outer periphery when subject to an external radial force in the unexpanded configuration. The compressed outer periphery may be smaller in diameter than the expanded outer periphery.

In some embodiments, the frame structure may be balloon-expandable.

In some embodiments, the frame structure may be self-expanding.

In some embodiments, the free end may comprise an atraumatic tip. For example, the free end may comprise a ball tip.

In some embodiments, the free end may be configured for piercing tissue.

In some embodiments, the free end may be bent distally.

In some embodiments, the free end may be bent proximally.

In some embodiments, the anchor may comprise a spiral wire. The anchor may comprise a plurality of spiral wires.

In some embodiments, the anchor may comprise a planar spiral band.

In some embodiments, the anchor may comprise at least one channel or lumen disposed therein. For example, the spiral band may comprise a hollow spiral band. In some embodiments, the at least one channel or lumen may comprise a stiffening member disposed therein.

In some embodiments, the anchor may have a circular, tubular, hollow, square, elongated, or triangular cross-section.

In some embodiments, the anchor may comprise a tapered spiral band. The tapered spiral band may be configured to taper in height axially. Alternatively, or in combination, the tapered spiral band may be configured to taper from a first end of the tapered spiral band to the free end. The first end may be a proximal end and the free end may be a distal end. In some embodiments, subsequent turns of at least a portion of the tapered spiral band may nest into each other to reduce a radial footprint of the tapered spiral band. Alternatively, or in combination, the tapered spiral band may comprise a support structure and a semi-permeable material or impermeable material disposed therein. The semi-permeable material or impermeable material may comprise a webbing material, a fabric, a polymeric material, or an elastomeric material. In some embodiments, the free end may be disposed radially outwards from the support structure. In some embodiments, the tapered spiral band further may comprise a lumen and a wire disposed within the lumen.

In some embodiments, the frame structure may be configured for expanding within the native valve of the patient.

In some embodiments, the unexpanded configuration may be sized and dimensioned for percutaneous insertion and the expanded configuration may be sized and dimensioned for implantation in the native valve of the patient.

In some embodiments, the frame structure may comprise a first and second opposite ends. The first end may extend above a native valve and the second end may extend below the native valve when the frame structure is anchored to the native valve.

In some embodiments, the frame structure may sit below the native valve when the frame structure is anchored to the native valve.

In some embodiments, the system may further comprise a valve segment within the frame structure comprising a biocompatible one-way valve. In some embodiments, at least a portion of the valve segment may be positioned within at least a portion of the frame structure. The valve segment may comprise at least one leaflet having an inner layer and an outer layer. The frame structure may be attached to the outer layer at one or more ends of the frame structure. The valve segment may comprise a plurality of leaflets.

Another aspect of the present disclosure provides a method for treating a diseased native valve in a patient. The method comprises advancing a frame structure and an anchor having a flat spiral shape from a first side of a native valve to a second side of a native valve; deploying the anchor adjacent the native valve; expanding the frame structure within the native valve from an unexpanded configuration to an expanded configuration; and anchoring the frame structure in the expanded configuration to the native valve with the anchor.

In some embodiments, anchoring the anchor may comprise deploying the anchor from a delivery configuration to a deployed configuration. The anchor may be configured to wrap at least partially around a delivery device in the deployed configuration. Alternatively, or in combination, he anchor may be configured to wrap at least partially around the frame structure in the deployed configuration. In some embodiments, a central point of the flat spiral shape may be co-axial with a longitudinal axis of a delivery device when the anchor is in the deployed configuration. In some embodiments, deploying the anchor may comprise deploying the anchor within a subvalvular plane of the heart. In some embodiments, the method may further comprise moving the deployed anchor into a subvalvular plane of the heart. In some embodiments, deploying the anchor may comprise actuating the anchor from the delivery configuration to the deployed configuration. In some embodiments, the method may further comprise maintaining the anchor in the deployed configuration with one or more locking mechanisms. In some embodiments, the one or more locking mechanisms may comprise a first feature disposed on a first loop of the anchor and a correspondingly-shaped second feature disposed on a second loop of the anchor and maintaining the anchor in the deployed configuration may comprise nesting the first and second features with one another when the anchor is in the deployed configuration. In some embodiments, actuating the anchor may comprise releasing the frame structure from radial constriction by a delivery device. In some embodiments, deploying the anchor comprises actuating the anchor from the delivery configuration to the deployed configuration on the second side of the native valve. In some embodiments, deploying the anchor may comprise actuating the anchor from the delivery configuration to the deployed configuration on the first side of the native valve and advancing the anchor in the deployed configuration through the native valve to the second side of the native valve. Advancing the anchor may comprise pushing the anchor through the native valve. Advancing the anchor may further comprise rotating the anchor through the native valve.

In some embodiments, the deployed configuration may comprise an intermediate deployed configuration and a fully deployed configuration. Actuating the anchor from the delivery configuration to the deployed configuration may comprise actuating the anchor from the delivery configuration to the intermediate deployed configuration. In some embodiments, the method may further comprise actuating the anchor from the intermediate deployed configuration to the fully deployed configuration adjacent a native valve in a patient. An outer perimeter of the flat spiral shape may be the same in the intermediate deployed configuration and the fully deployed configuration. In some embodiments, the anchor may comprise a first loop, a second loop, and one or more locking mechanisms. The method may further comprise coupling the first loop to the second loop with the one or more locking mechanisms to maintain the anchor in the fully deployed configuration.

In some embodiments, deploying the anchor may comprise positioning the anchor such that it is located only on the second side of the native valve.

In some embodiments, the frame structure may be detachably coupled to a distal end of a delivery device. Advancing the frame structure may comprise advancing the distal end of the delivery device from the first side of the native valve to the second side of the native valve. The method may further comprise releasing the frame structure from the distal end of the delivery device. In some embodiments, the method may further comprise steering the distal end of the delivery device such that the distal end of the delivery device points towards the first side of the native valve. In some embodiments, expanding the frame structure and releasing the frame structure may occur simultaneously. In some embodiments, the anchor may be detachably coupled to the distal end of the delivery device and advancing the frame structure and advancing the anchor may occur simultaneously.

In some embodiments, the anchor may be detachably coupled to a distal end of a delivery device. Advancing the anchor may comprise advancing the distal end of the delivery device from the first side of the native valve to the second side of the native valve. The method may further comprise releasing the anchor from the distal end of the delivery device. In some embodiments, the method may further comprise steering the distal end of the delivery device such that the distal end of the delivery device points towards the first side of the native valve. In some embodiments, the frame structure may be detachably coupled to a distal end of a second delivery device and advancing the frame structure and advancing the anchor may occur independently of one another.

In some embodiments, the frame structure may comprise a first and second opposite ends. Expanding the frame structure may comprise expanding the frame structure such that the first end extends above the first side of the native valve and the second end extends below second side of the native valve.

In some embodiments, expanding the frame structure may comprise expanding at least a portion the frame structure within at least a portion of the deployed anchor to anchor the frame structure to the native valve.

In some embodiments, the frame structure may be balloon-expandable. Expanding the frame structure may comprise inflating a balloon disposed within the frame structure, wherein inflation of the balloon causes expansion of the frame structure.

In some embodiments, the frame structure may be self-expanding. Expanding the frame structure may comprise releasing the frame structure from radial constriction by a delivery device.

In some embodiments, the anchor may comprise a free end. Anchoring may comprise rotating the free end of the anchor around one or more structures on the second side of the native valve. In some embodiments, the method may further comprise counter-rotating the free end of the anchor after rotating the free end around the one or more structures. In some embodiments, the one or more structures may comprise one or more valve leaflets of the native valve. Alternatively, or in combination, the one or more structures may comprise one or more chordae of the left ventricle. In some embodiments, the free end may comprise an atraumatic tip. For example, the free end may comprise a ball tip. In some embodiments, the free end may be configured for piercing tissue. In some embodiments, the free end may be bent distally. In some embodiments, the free end may be bent proximally.

In some embodiments, the anchor may comprise a spiral wire. The anchor may comprise a plurality of spiral wires.

In some embodiments, the anchor may comprise a planar spiral band.

In some embodiments, the anchor may comprise at least one channel or lumen disposed therein. For example, the anchor may comprise a hollow spiral band. In some embodiments, the at least one channel or lumen may comprise a stiffening member disposed therein.

In some embodiments, the anchor may have a circular, tubular, hollow, square, elongated, or triangular cross-section.

In some embodiments, the anchor may comprise a tapered spiral band. The tapered spiral band may be configured to taper in height axially. Alternatively, or in combination, the tapered spiral band may be configured to taper from a first end of the tapered spiral band to the free end. The first end may be a proximal end and the free end may be a distal end. In some embodiments, subsequent turns of at least a portion of the tapered spiral band may nest into each other to reduce a radial footprint of the tapered spiral band. Alternatively, or in combination, the tapered spiral band may comprise a support structure and a semi-permeable material or impermeable material disposed therein. The semi-permeable material or impermeable material may comprise a webbing material, a fabric, a polymeric material, or an elastomeric material. In some embodiments, the free end may be disposed radially outwards from the support structure. In some embodiments, the tapered spiral band further may comprise a lumen and a wire disposed within the lumen.

In some embodiments, the frame structure may comprise a valve segment therewithin comprising a biocompatible one-way valve.

In some embodiments, the native valve may be in a heart of a patient. The method may further comprise transseptally inserting a distal end of a delivery device detachably coupled to the frame structure or to the anchor into a left atrium of the heart. In some embodiments, the native valve may comprise a mitral valve. The first side of the native valve may comprise a left atrium, and the second side of the native valve may comprise a left ventricle.

In another aspect, valve comprising any of the features described herein in any combination thereof is provided.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

FIGS. 31-35 illustrate another valve device similar to the one of FIG. 6, in accordance with embodiments. FIG. 31 is a perspective view. FIG. 32 is a front view. FIG. 33 is a back view. FIG. 34 is a top view. FIG. 35 is an enlarged view of a bottom portion of the device, showing attachment of the anchor to the frame structure.

FIGS. 36 and 37 are perspective views. FIG. 38 is a front view. FIG. 39 is a top view.

FIGS. 40-42 are front views of valve devices similar to the one of FIG. 6, illustrating different anchors, in accordance with embodiments.

FIG. 44 is a front view of the device. FIG. 45 is a perspective top view. FIG. 46 is a bottom view. FIG. 47 is a perspective view. FIG. 48 is a perspective view of the valve device loaded on a delivery catheter. FIG. 49 is a bottom view of the device loaded on a delivery catheter.

FIGS. 63-64 show an optional tip orientation for a spiral band anchor, in accordance with embodiments.

FIGS. 65-66 show another optional tip orientation for a spiral band anchor, in accordance with embodiments.

DETAILED DESCRIPTION

Figure 1:
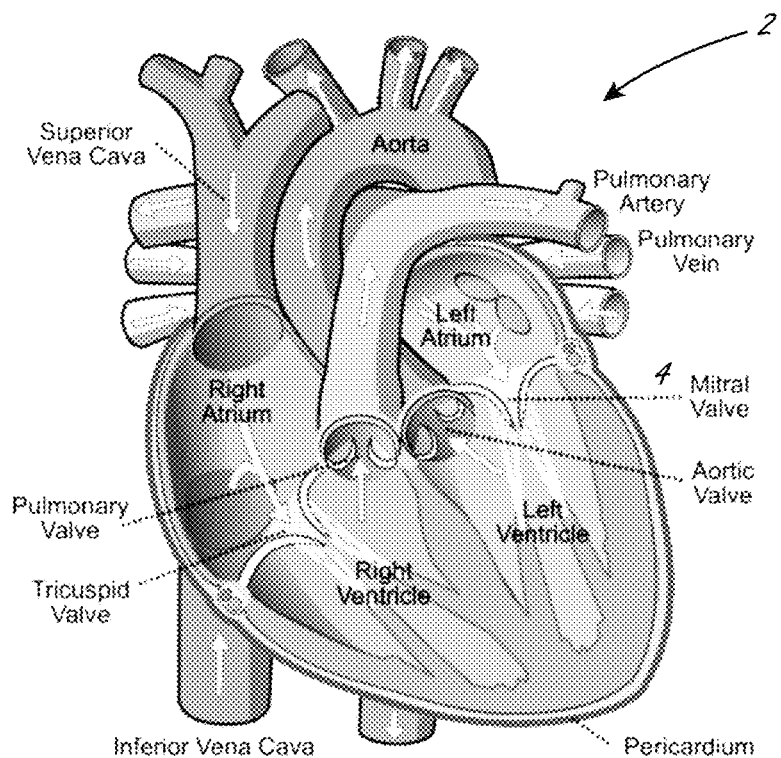
FIG. 1 is a schematic of a human heart illustrating the path of blood flow through the heart, in accordance with embodiments.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments, however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The present disclosure is described in relation to deployment of systems, devices, or methods for treatment of a diseased native valve of the heart, for example a mitral valve, aortic valve, or tricuspid. However, one of skill in the art will appreciate that this is not intended to be limiting and the devices and methods disclosed herein may be used in other anatomical areas and in other surgical procedures.

For convenience in explanation and accurate definition in the appended claims, the terms "up" or "upper", "down" or "lower", "inside" and "outside" are used to describe features of the present disclosure with reference to the positions of such features as displayed in the figures.

In many respects the modifications of the various figures resemble those of preceding modifications and the same reference numerals followed by subscripts "a", "b", "c", and "d" designate corresponding parts. It will be understood by one of ordinary skill in the art that modifications of corresponding parts of the various figures are interchangeable with one another between embodiments to arrive at multiple combinations with multiple modified parts.

Figure 2:
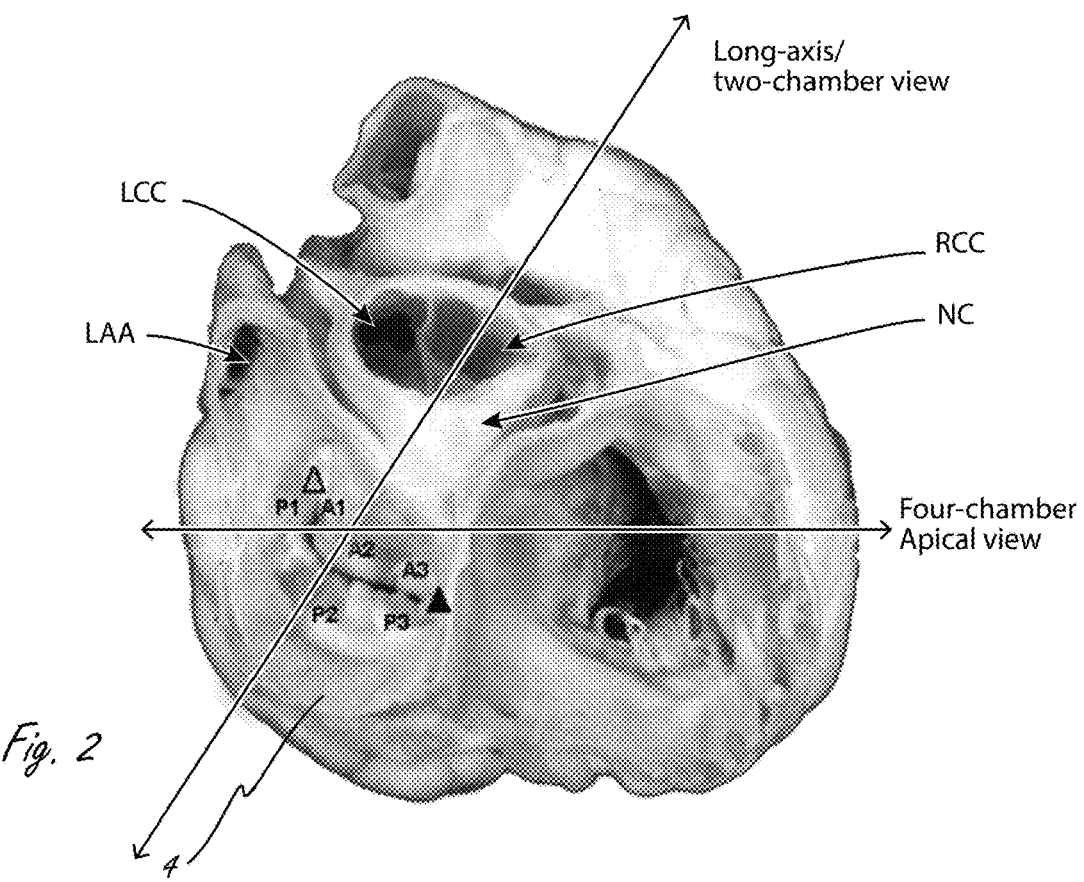
FIG. 2 is a cross-sectional view of a heart looking down through the mitral valve, aortic valve, and aorta, in accordance with embodiments.
Figure 3:
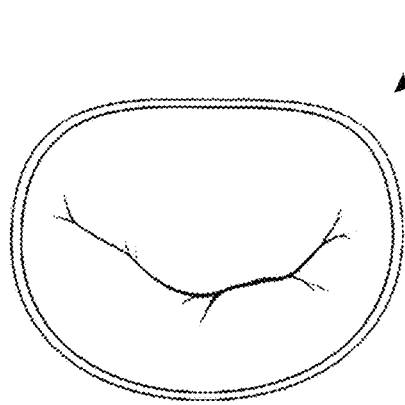
FIG. 3 is a schematic of a healthy mitral valve, in accordance with embodiments.

Turning now to the drawings, wherein like components are designated by like reference numerals throughout the various figures, attention is directed to FIGS. 1-5. FIG. 1 shows a human heart 2 and the blood flow pathways through the four chambers of the heart. FIG. 2 is a human heart 2 showing the mitral valve 4, aortic valve 9, and aorta 1. The mitral valve 4 includes two leaflets 4a, 4b. The anterior (aortic) leaflet 4a is adjacent the aorta 1. The posterior (mural) leaflet 4b is remote from the aorta 1. The aortic valve 9 includes three leaflets. In the current view, the heart 2 is in systole with the aortic valve 9 open and the mitral valve 4 closed. Whereas FIG. 1 illustrates a healthy heart 2, FIGS. 2-5 illustrate exemplary mitral valve 4 disease states which may be addressed by the prosthetic valve in accordance with the present disclosure. The prosthetic valve may also be used to treat functional regurgitation such as functional mitral regurgitation (FMR).

FIGS. 6-18 show an exemplary valve prosthesis 10 (also referred to herein as "valve device") for replacement of a diseased mitral valve in accordance with the present disclosure. The illustrated valve prosthesis 10 comprises a frame structure 12, a valve segment 14, and an anchor 15. FIGS. 6-10 show the valve prosthesis 10 in an expanded, deployed state. FIGS. 12-18 show the frame structure 12 without the valve segment 14. The frame structure 12 is in a collapsed state in FIGS. 12-15 and an expanded state in FIGS. 16-18. The anchor 15 is shown in a deployed state.

The exemplary valve prosthesis 10 will now be described with reference to FIGS. 6-11. In the illustrated embodiment, valve prosthesis 10 is configured for replacement of a native mitral valve. Valve 10 includes a frame structure 12, valve segment 14, and anchor 15. In the illustrated embodiment, the anchor 15 includes a wire 20 formed in a helical or spiral shape around the frame structure.

The exemplary frame structure 12 is configured like a stent. The frame structure 12 has an expanded state and an unexpanded (e.g., collapsed or compressed) state. The compressed state is sized and dimensioned for percutaneous insertion and the expanded state sized and dimensioned for implantation in a native valve of a patient. In various embodiments, the frame structure 12 comprises an expanded outer periphery and a compressed outer periphery when subject to an external radial force, the compressed outer periphery being slightly smaller in diameter than the expanded outer periphery. The frame structure 12 is shown in the expanded, deployed state in FIG. 6. The frame structure 12 is shown in the collapsed, delivery state in FIG. 12.

The exemplary frame structure 12 is a scaffold in a diamond pattern formed from a shape memory material (e.g. NiTi). One of ordinary skill in the art will appreciate from the description herein that many other structures, materials, and configurations may be employed for the frame structure 12. For example, the frame structure 12 may be formed of a polymer of sufficient elasticity. The frame structure 12 may be formed of a combination of a metal and polymer, such as a metal (e.g., shape memory material) covered in polymer. The frame structure 12 may include a variety of patterns besides diamond shapes.

Valve prosthesis 10 includes a valve segment 14 within the frame structure 12. The exemplary valve segment 14 is expandable and collapsible. In the illustrated embodiment, the valve segment 14 is affixed within the frame structure 12 and expands and collapses with the frame structure 12. Valve segment is used somewhat interchangeably with prosthetic valve leaflet and generally refers to the prosthetic leaflets and frame. As used herein, "prosthetic valve" may refer to all manner of prosthetic and artificial replacement valves including tissue (biological) valves, tissue-engineered valves, polymer valves (e.g. biodegradable polymer valves), and even certain mechanical valves.

In the illustrated embodiment, frame structure 12 is a closed frame such that blood flow is forced through valve segment 14 therein. One or more skirts and/or seals may help force blood through valve segment 14.

Figure 11:
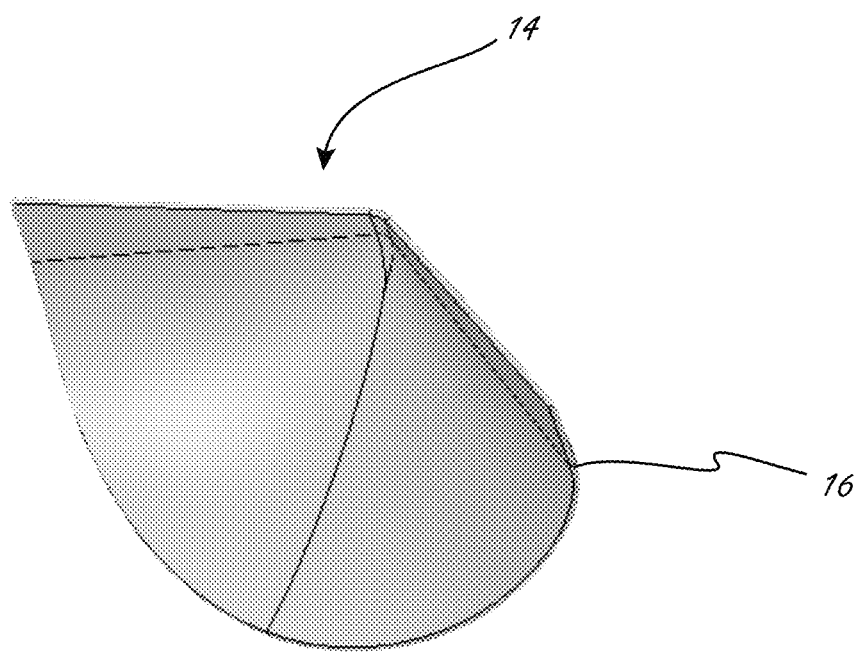
FIG. 11 is a perspective view of the prosthetic valve leaflet of the valve of FIG. 6, in accordance with embodiments.
Figure 12:
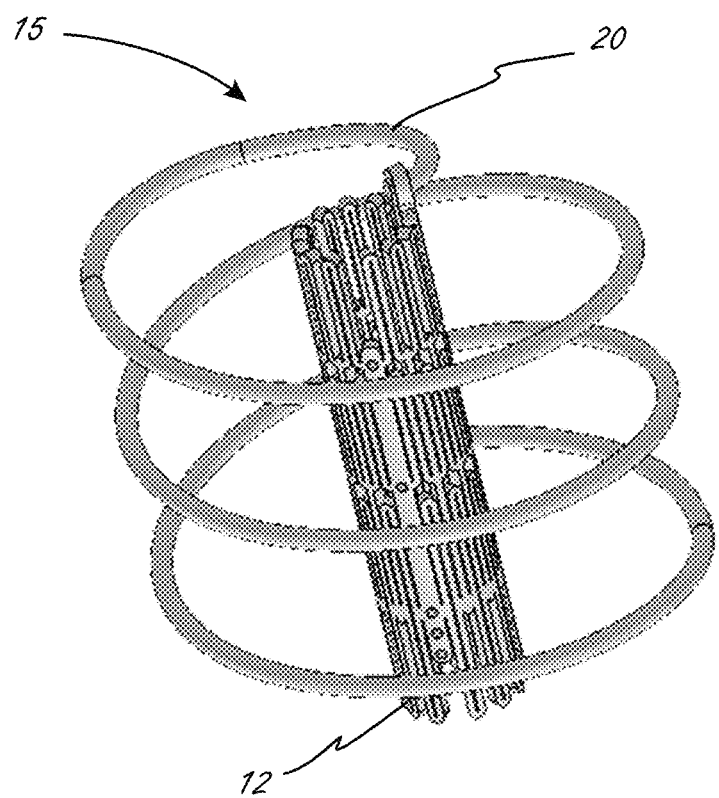
FIGS. 12-18 are several views of the frame structure of the valve of FIG. 6, in accordance with embodiments.
Figure 13:
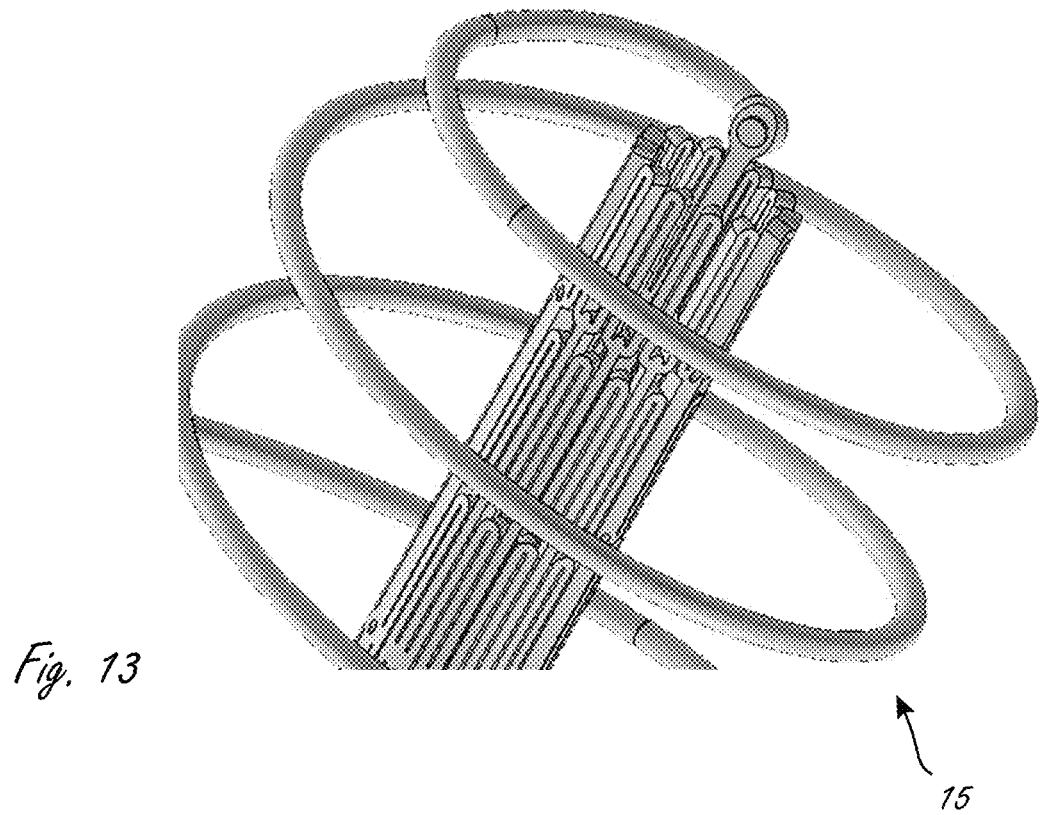
Figure 14:
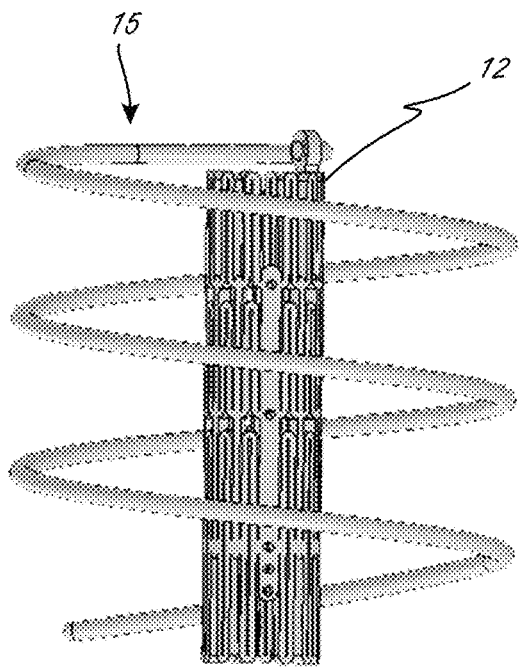
Figure 15:
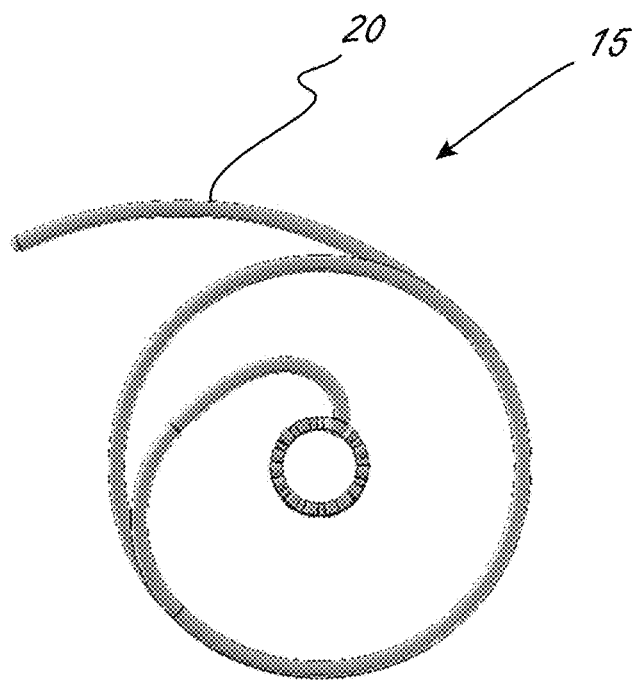
Figure 16:
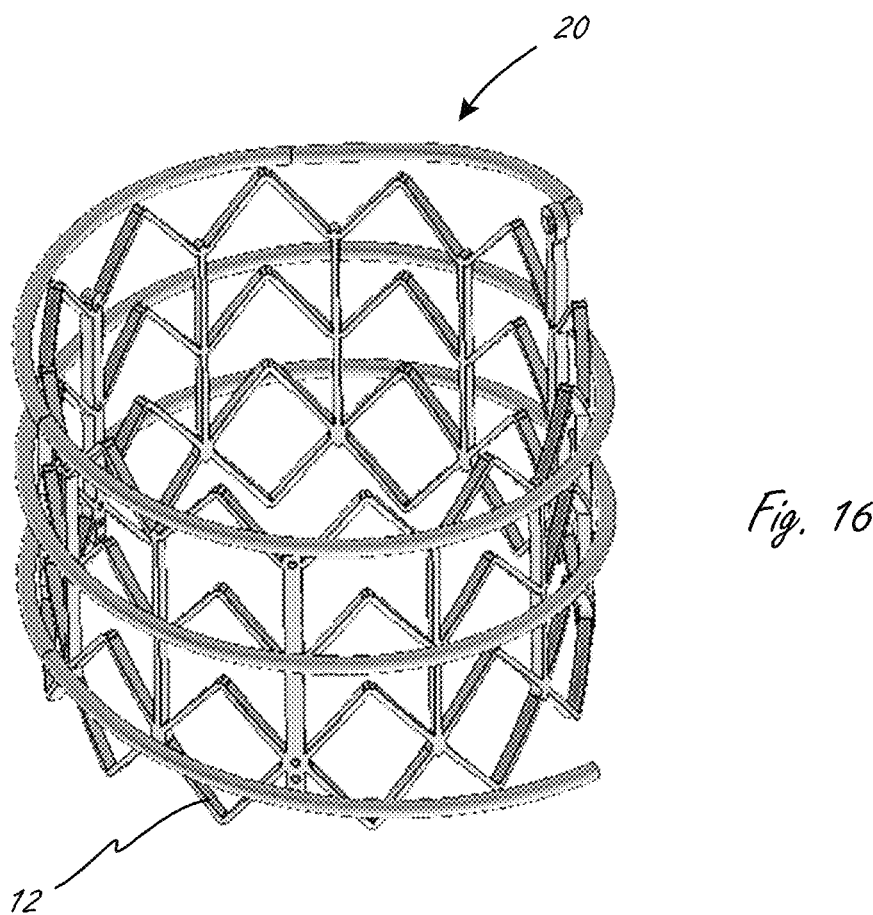
Figure 17:
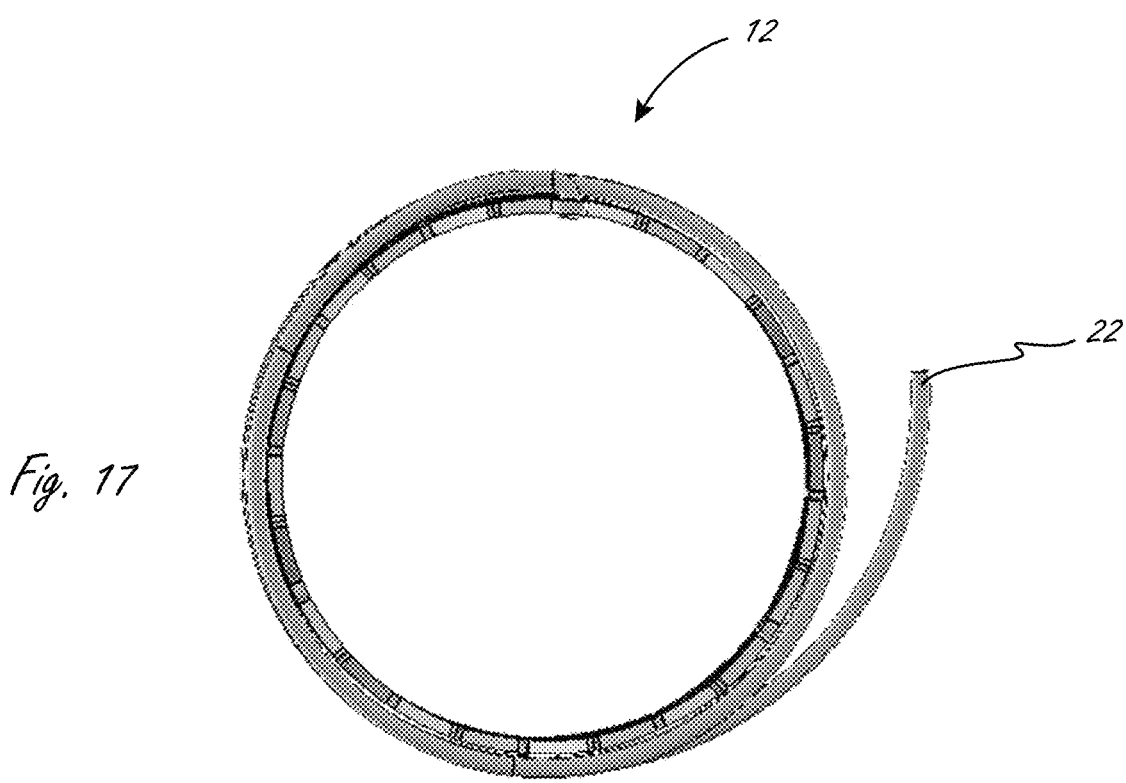
Figure 18:
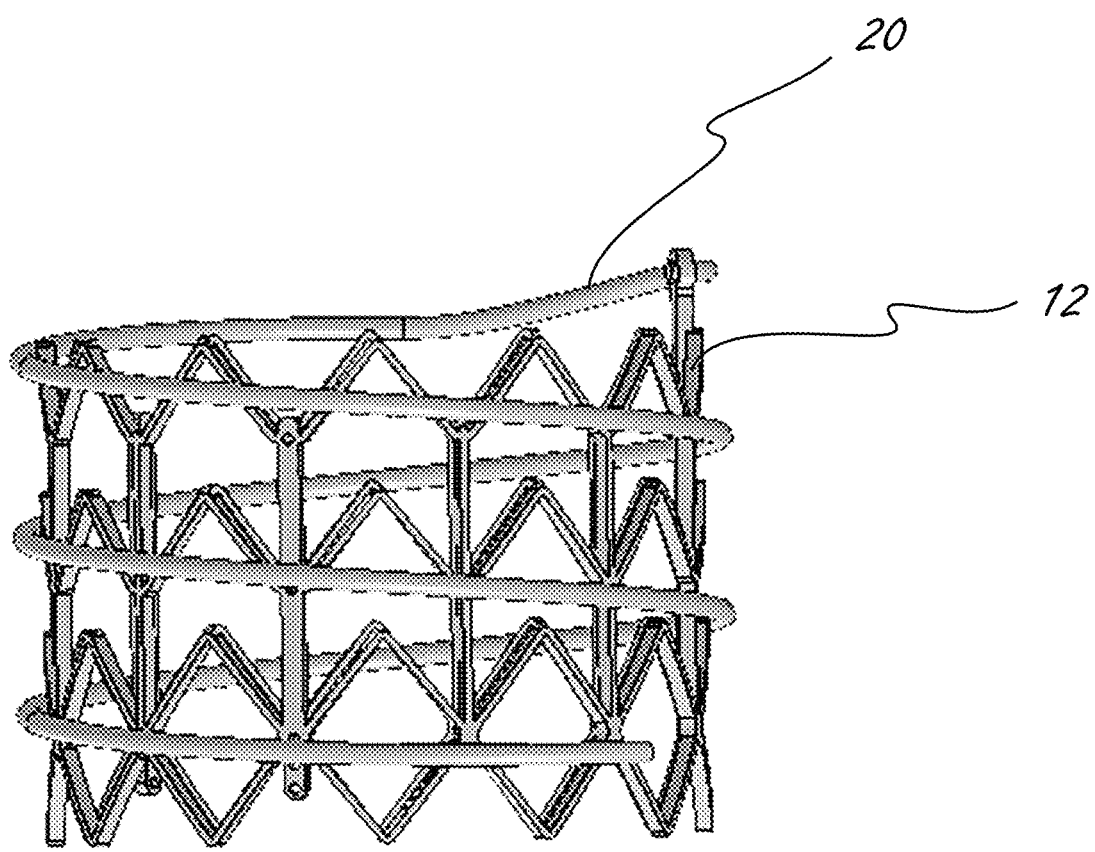

Valve segment 14 can be configured as would be understood by one of skill from the description herein. The valve segment 14 can be similar to existing transcatheter valves. The valve segment 14 can be similar to existing surgical tissue valves, and mechanical valves. In various embodiments, the valve segment 14 includes leaflets 16 formed of multi-layered materials for preferential function. At least one leaflet 16 may have an inner layer and an outer layer. In various embodiments, the leaflet 16 is connected to a valve structure which in turn is connected to the frame structure 12. The valve structure may be connected to the frame structure 12 before or after the frame structure 12 has been deployed adjacent a native valve. In various embodiments, the leaflet 16 is attached to the frame structure 12 directly. The leaflet 16 may have an inner layer and an outer layer, with the outer layer attached to the frame structure 12. The leaflet 16 may be attached to an end of the frame structure 12. Alternatively, or in combination, the leaflet 16 may be attached to an intermediate portion of the frame structure 12. In various embodiments, the valve segment 14 includes a plurality of leaflets 16, such as two, three, or more leaflets. In the illustrated embodiment, the valve segment 14 includes three leaflets 16 which are attached to frame structure 12. An exemplary leaflet 16 is shown in FIG. 11. The leaflet 16 is concave to permit flow in one direction. In particular, flow in one direction causes the leaflet(s) 16 to deflect open and flow in the opposite direction causes the leaflet(s) 16 to close.

Turning back to FIGS. 6-18, and more particularly FIGS. 12-18, an exemplary anchor 15 comprises a helical member, such as wire 20, having a free end 22. The other end of the wire 20 is attached to a top end of frame structure 12. In the illustrated embodiment, one end of the wire 20 is fixed to a strut of the frame structure 12. This end can be attached by suitable means as would be understood by one of skill in the art from the description herein including, but not limited to, a weld, an adhesive, and a mechanical fastener. In various embodiments, the helical wire 20 is attached to the frame structure only at the location of the second end.

Although referred to as an anchor, one will appreciate that anchor 15 does not require performing an anchor function in the traditional sense. As will be described in more detail below, the anchor guides valve prosthesis 10 into a desired position within a native valve. The anchor 15 may also mitigate against undesired entanglement and disturbances to the chordae tendineae and valve leaflets of the mitral valve.

Wire 20 is formed of a material having sufficient rigidity to hold a predetermined shape. In the exemplary embodiment, the wire 20 is formed of a shape memory material (e.g. NiTi). It may be desirable for at least an end portion to be relatively rigid such that it can exert a force to move chordae tendineae, while still retaining flexibility to be collapsed within a catheter. In various embodiments, the end portion (including free end 22) only needs sufficient rigidity to hold its shape and will deform under a load. For example, the end portion may be configured with similar rigidity to a guidewire, or slightly stiffer.

In various embodiments, the anchor 15 comprises a helical member. The helical member may comprise a helical wire or flat ribbon. The helical member may comprise a three-dimensional surface as described herein.

In various embodiments, the anchor 15 may comprise a first portion comprising the helical wire 20 and another portion. Alternatively, or in combination, the anchor 15 may comprise a plurality of helical wires 20. For example, the anchor 15 may comprise at least two helical wires 20 having the same or different diameters. Alternatively, or in combination, the anchor 15 may comprise at least two helical wires 20 having the same or different winding pitches.

In various embodiments, the anchor 15 may comprise a plurality of anchors, for example a plurality of helical wires 20 as described herein.

In various embodiments, the anchor 15 may comprise a flat spiral shape. Loops of the flat spiral shaped anchor may be generally positioned within the same plane (the plane being perpendicular to a longitudinal axis of a delivery device) as described herein.

Figure 4:
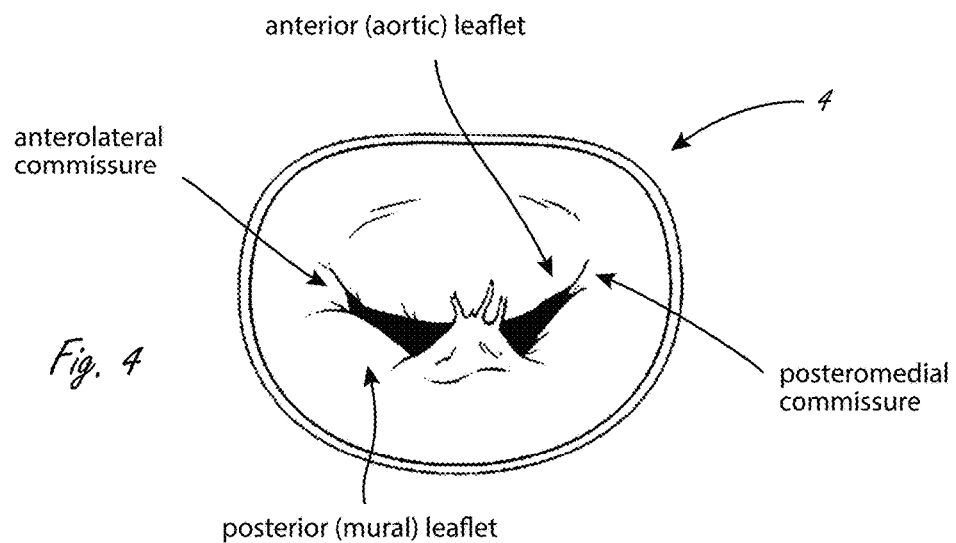
FIGS. 4 and 5 are schematics of diseased mitral valves, in accordance with embodiments.
Figure 5:
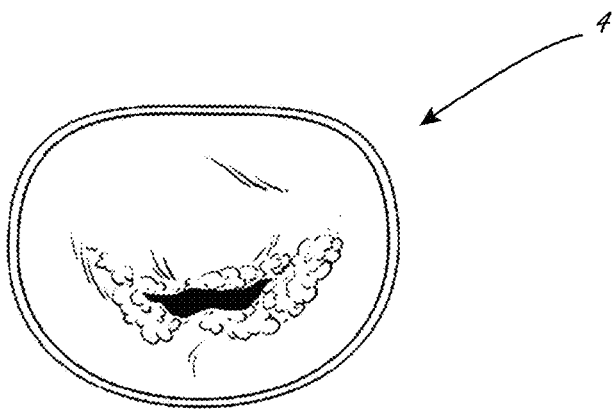

In the illustrated embodiment, valve prosthesis 10 is configured for replacing a mitral valve and free end 22 is configured for insertion through a commissure. FIG. 1 is a schematic of a human heart 2 having a mitral valve 4. FIGS. 2 and 4 show an exemplary mitral valve 4. As can be seen in the figures, several commissure points (anterolateral commissure 4d and posteromedial commissure 4e) are presented at the ends of the valve leaflets 4a, 4b.

With continued reference to FIGS. 6-18, the exemplary free end 22 is sized and dimensioned for insertion through one of the commissures. In the various embodiments, the free end 22 is configured to be atraumatic to avoid risk of injury to the valve tissue and leaflets. The free end 22 may be in the form of a blunt end, a ball tip, a curved tip (e.g., J-tip or pigtail), and other atraumatic shapes. In various embodiments, the free end 22 is configured with a sharp end to pierce tissue. In various embodiments, the free end 22 is separate from and extends outward from the main coils of the anchor 15. In various embodiments, the main body coils of the anchor 15 circumscribe an area (in the case of a spiral coil) or a volume (in the case of a helical coil) having a diameter, and the free end 22 extends to a radius greater than the diameter of the anchor 15. In various embodiments, the free end 22 extends to a radius substantially greater than the diameter of the anchor 15. In various embodiments, the free end 22 is configured to circumscribe a larger diameter than the anchor 15. In various embodiments, the free end 22 is configured to circumscribe all of the chordae tendineae of the native valve to be treated.

In various embodiments, wire 20 has varying stiffness along its length. The wire 20 may have two or more segments of differing stiffness and/or the stiffness may transition over its length. In various embodiments, wire 20 is attached to frame 12 at multiple points such that free end 22 is relatively flexible and the wire 20 is more rigid along portions where it is attached to the frame structure 12.

In various embodiments, free end 22 extends radially outward from frame structure 12, and in particular the remainder of wire 20. As will be described below, the free end 22 is configured to encircle a larger radius than the main coils of the wire 20. When the main coils of wire 20 have a generally curved shape (e.g., spiral, helical, tubular, frustoconical, etc.), the free end 22 may extend radially outward from the curved shape. For example, when the main coils of wire 20 have a generally spiral shape, the free end 22 may extend radially outward from the spiral shape. When the main coils of wire 20 have a generally tubular shape, the free end 22 may extend radially outward from the tubular shape. When the main coils of wire 20 have a generally helical shape, the free end 22 may extend radially outward from the helical shape. When the main coils of wire 20 have a generally frustoconical shape, the free end 22 may extend radially outward from the frustoconical shape. The larger diameter facilitates capturing of the valve leaflets and/or chordae tendineae within the sweep of the free end 22 during rotation as will be described in more detail below.

A method of implanting valve prosthesis 10 in accordance with the present disclosure will now be described with reference to FIGS. 19-28. Although shown and described with respect to a mitral valve, one of ordinary skill in the art will understand that the principles described herein may be applied equally to other atrioventricular valves. Aspects of the procedure, delivery tool, and implanted valve prosthesis are similar to those described in U.S. Pat. Nos. 9,034,032; 9,005,273; 8,323,336; 8,075,615; 7,621,948; and 7,175,656 and U.S. Pub. No. 2011/0288637, which are incorporated herein for all purposes in their entirety.

Figure 19:
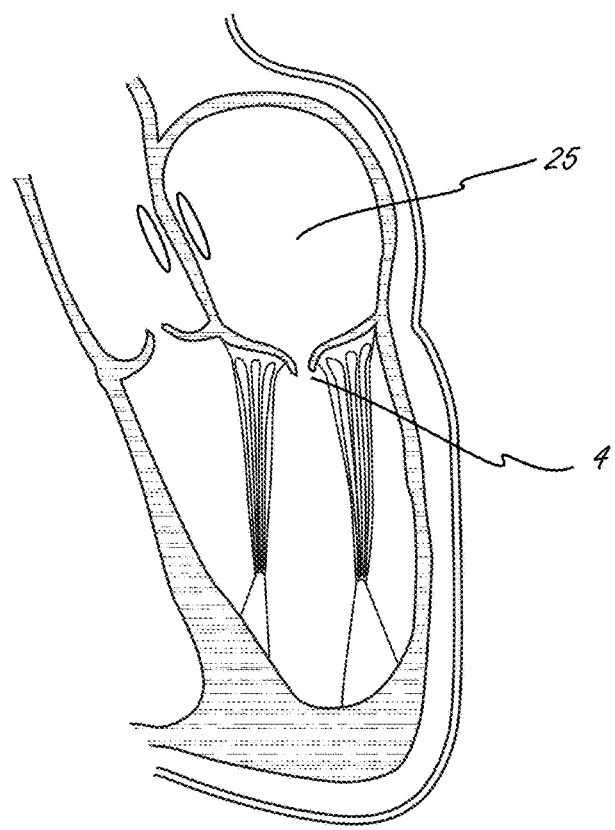
FIGS. 19-26 are several views of the method of implanting the valve of FIG. 6, in accordance with embodiments.

Prior to implantation, valve prosthesis 10 may be collapsed and loaded into a delivery device 30, for example, a delivery catheter. The valve system may optionally be primed before or after loading into the delivery catheter 30. FIG. 19 shows a cross-sectional side view of a heart 2 with a transsseptal puncture 27 in the atrial septum thereof. The leaflets 42 of valve 4 do not fully prolapse and the patient is experiencing regurgitation.

Figure 20:
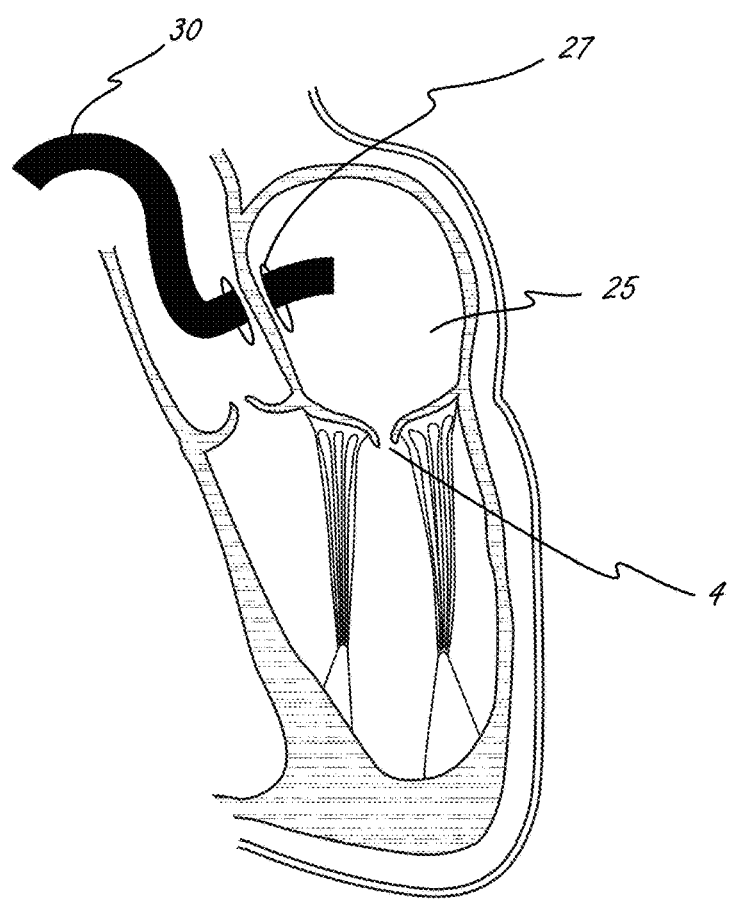

Next, the delivery catheter 30 is inserted through an introducer into a vessel. The delivery catheter 30 can be guided over a guidewire to a target location using the Seldinger technique. In the illustrated embodiment, the delivery catheter 30 is guided to the left atrium 25 through a transseptal puncture 27 in conventional fashion as shown in FIG. 20.

Figure 21:
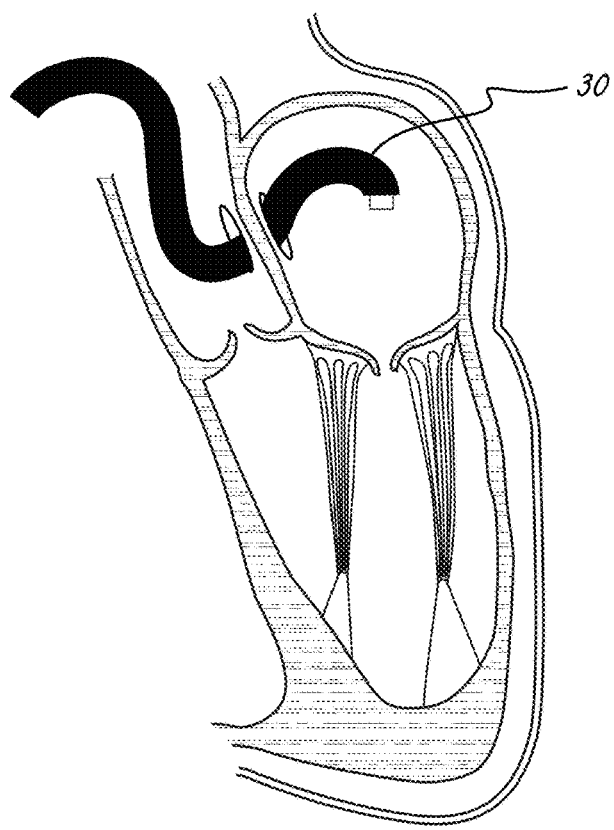
Figure 22:
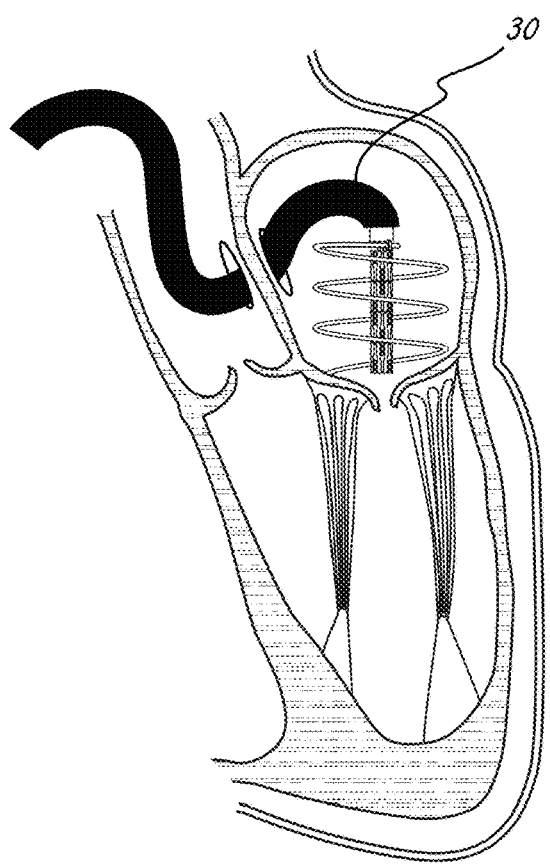

Turning to FIGS. 21-22, at this point, the end of the delivery catheter 30 is pointed towards the mitral valve 4. Valve prosthesis 10 is then pushed out of the distal end of delivery catheter 30. The delivery device 30 may comprise an outer catheter 50 and an inner catheter or shaft 52. Delivery device 30 may refer to various components in certain embodiments. For example, delivery device 30 may refer to a steerable catheter for transseptal delivery. Delivery device 30 may refer to a catheter for delivery of the replacement valve, frame structure, and/or anchor. In some embodiments, delivery device 30 may refer to a first delivery device component detachably coupled to the anchor and a second delivery device component detachably coupled to the frame structure. In some embodiments, one or more valve prosthesis components may be different delivery devices or different components of a delivery device system. In some embodiments, once the delivery device 30 is in position, the delivery tube 52 extends out of the outer catheter 50 to move valve device 10 distally towards the native valve 4. As the valve prosthesis 10 comes out from the delivery catheter 30, an anchor 15, such as wire 20, is deployed (e.g., from a straightened shape within the delivery device 30) to its pre-formed deployed shape and wraps around frame 12, which remains in its collapsed state as shown in FIG. 22. The valve prosthesis 10 is then aligned with the target native valve 4 so the axis of the prosthetic valve 10 is aligned with a central axis of the native valve 4.

Figure 23:
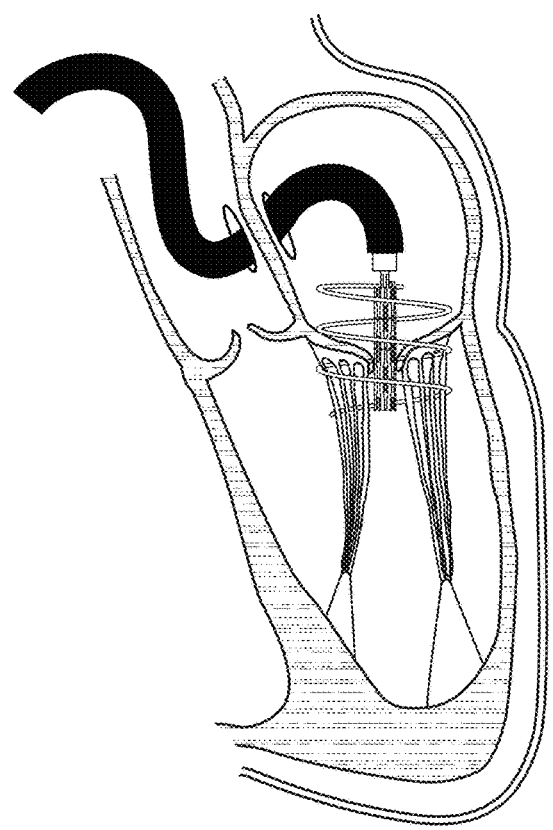
Figure 24:
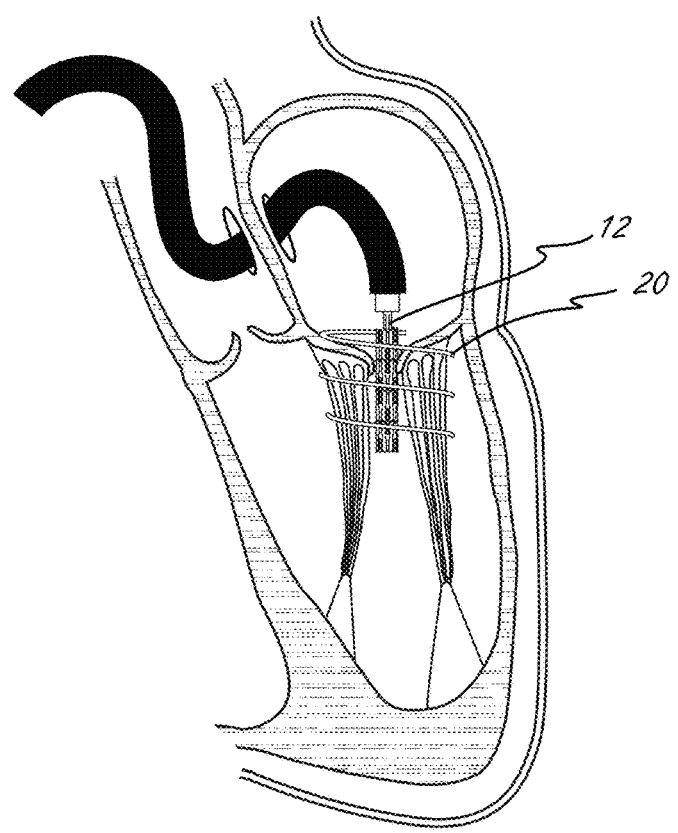

Turning to FIGS. 23-24, valve 10 is anchored to the native valve 4 using exemplary helical wire 20. The valve prosthesis 10—frame structure 12, wire 20, and valve segment 14—are slowly rotated into the native mitral valve 4. In the illustrated embodiment, a torquer is provided in the delivery catheter 30 for rotating valve 10. Free end 22 of wire 20 is rotated through a commissure and extends below the native valve 4 annulus. The valve prosthesis 4 is further rotated so the free end 22 captures the chordae tendineae (also referred to as "papillary muscles") 40 and/or native valve leaflets 42. As the wire 20 is continually rotated, the chordae tendineae 40 are gathered and pulled radially inward. Free end 22 has a larger radius than the main body of the helical coil (e.g., is disposed radially outward of the main body of the helical coil) in order to facilitate capture of the chordae tendineae 40 during rotation of the valve prosthesis 10. Frame structure 12 also moves into the native valve 4 as the wire 20 is rotated. Valve prosthesis 10 is in the correct position when the chordae tendineae 40 have been captured to a sufficient degree and/or frame structure 12 is in the desired location in the native valve 40. Insertion of the device through the native valve may be facilitated by the natural opening and closing of the native valve during the cardiac cycle. In the illustrated embodiment, the chordae tendineae 40 are pulled inwardly into a bunches (best seen in FIG. 25). The native valve leaflets 42 are also in communication with the helical coil 20. At this stage valve device 10 is rigidly anchored adjacent the native valve 40 annulus.

If the clinician desires to remove or reposition the valve, the helical wire 20 can be counter-rotated to back out the device 10 from the native valve 4. The implant rotation procedure can then be repeated.

Figure 25:
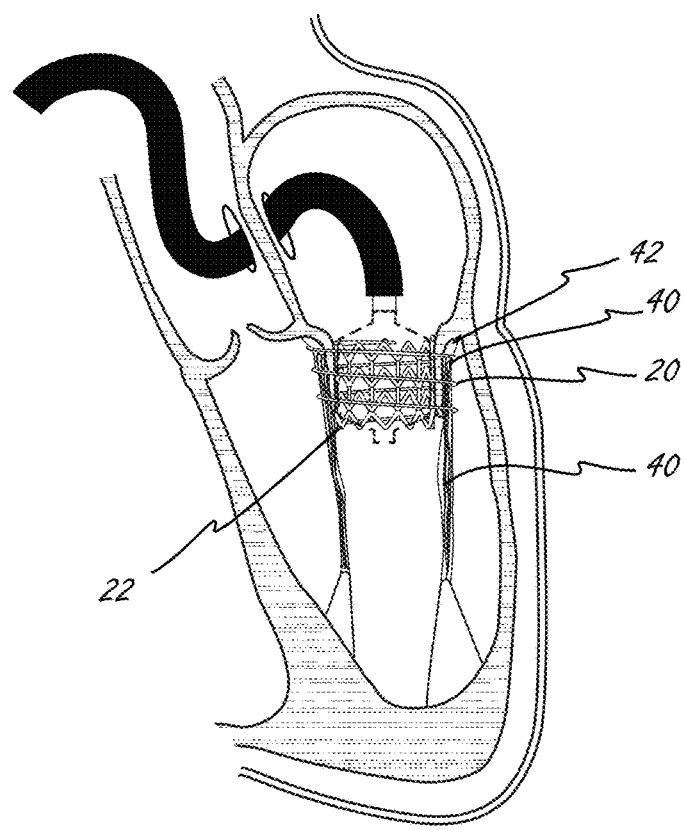
Figure 27:
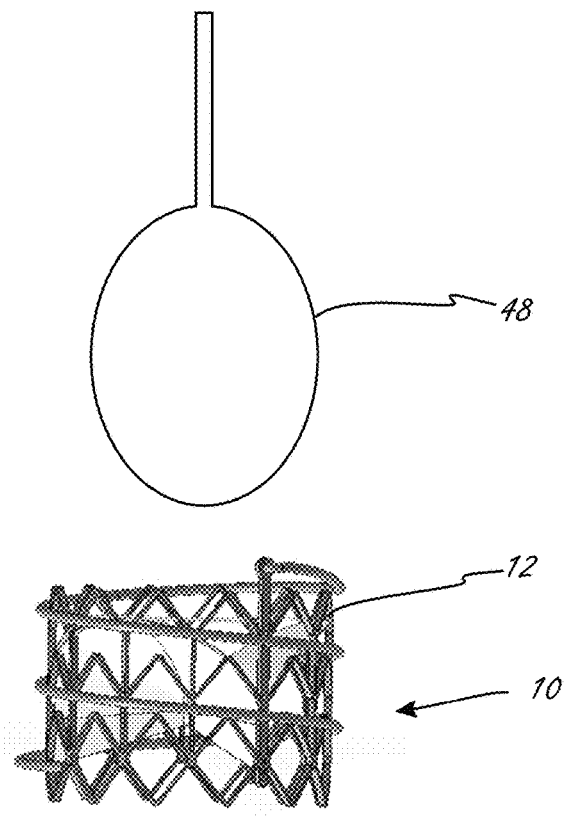
FIGS. 27 and 28 illustrate expanding of the frame structure using a balloon, in accordance with embodiments.
Figure 28:
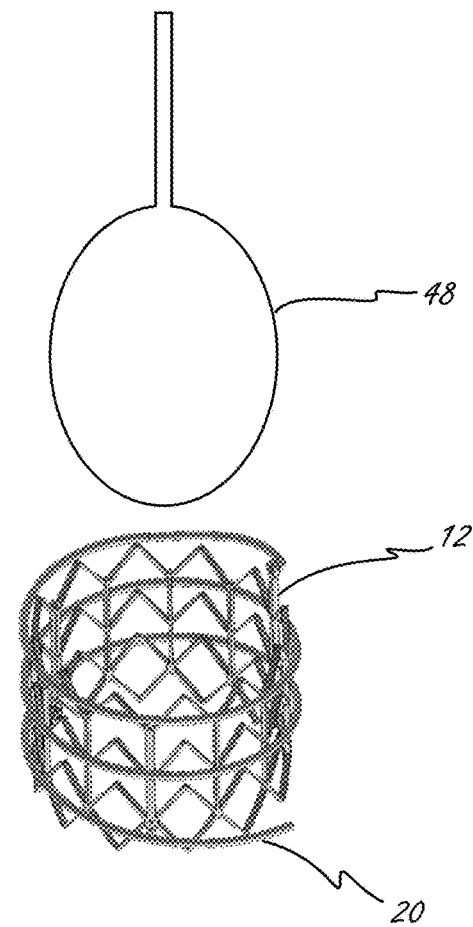

Frame structure 12 is expanded once valve 10 is in the desired location as shown in FIG. 25. The frame structure 12 may comprise a first and second opposite ends, the first end extending above a native valve and the second end extending below the native valve when the frame structure 12 is anchored to the native valve 4. In the illustrated embodiment, the frame structure 12 is expanded with a balloon 48 as shown in FIGS. 27-28. In various embodiments, the frame structure 12 is self-expanding. The self-expanding exemplary frame structure 12 is formed of a shape memory material or any material having superelastic properties. The self-expanding frame structure 12 is configured and expands in a similar manner to a self-expanding stent or scaffold. Expanding the frame structure 12 comprises removing a sheath (for example, outer sheath 50) of the delivery device 30 from the frame structure 12.

Figure 26:
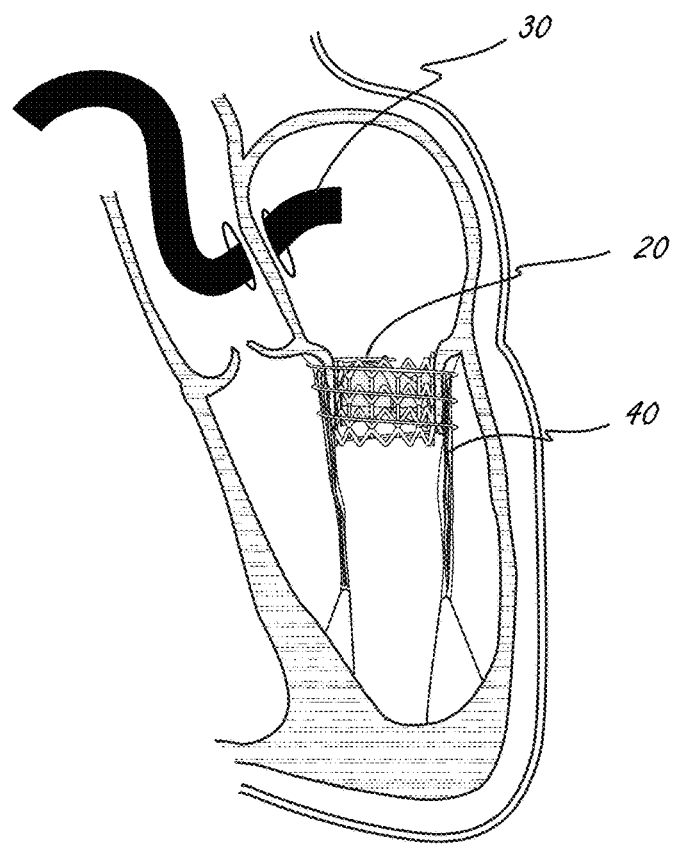

Once the frame structure 12 is expanded the entire valve assembly 10 is released from the delivery catheter 30 and the delivery catheter 30 is removed as shown in FIG. 26. In some embodiments, expansion of the frame structure 12 may occur simultaneously with release of the frame structure 12 from the delivery catheter 30.

In the illustrated embodiment, the valve structure 14 and frame structure 12 are deployed together. One of ordinary skill in the art will appreciate, however, that the frame structure 12 can be deployed first and then receive the prosthetic valve segment 14.

In various embodiments, valve prosthesis 10 does not include a valve segment 14. Instead, the frame structure 12 and anchor 15 are positioned within the native valve 4. The frame structure 12 is configured to receive a valve segment 14 delivered separately. In certain embodiments, the frame structure 12 can be configured to receive one of several valve sizes and types. In this manner, a clinician can choose the proper valve for the individual patient.

In the illustrated embodiment, the helical wire 20 of anchor 15 guides the valve system 10 along a desired axis into position adjacent the native valve 4. The wire 20 also provides an initial anchoring. The valve prosthesis 10 is finally anchored when the frame structure 12 is expanded within the native valve 4. The frame structure 12 dilates the valve leaflets 14 and the compressive force fixes the valve prosthesis 10 into position. Thereafter tissue ingrowth ensures the valve prosthesis 10 remains seated and does not migrate.

The valve devices described herein in accordance with the present disclosure provides several advantages over conventional valve systems. Embodiments described herein provide an easy-to-use, repositionable device. Unlike conventional valve systems, the valve prosthesis described herein reduces the risk of injuring or tearing chordae. Typical mitral valve replacement systems involve implanting a prosthetic annulus or ring around the valve. The ring increases the circumference of the valve and risks occluding the entry to the aortic valve. The valve device described herein overcomes these and other problems.

Figure 29:
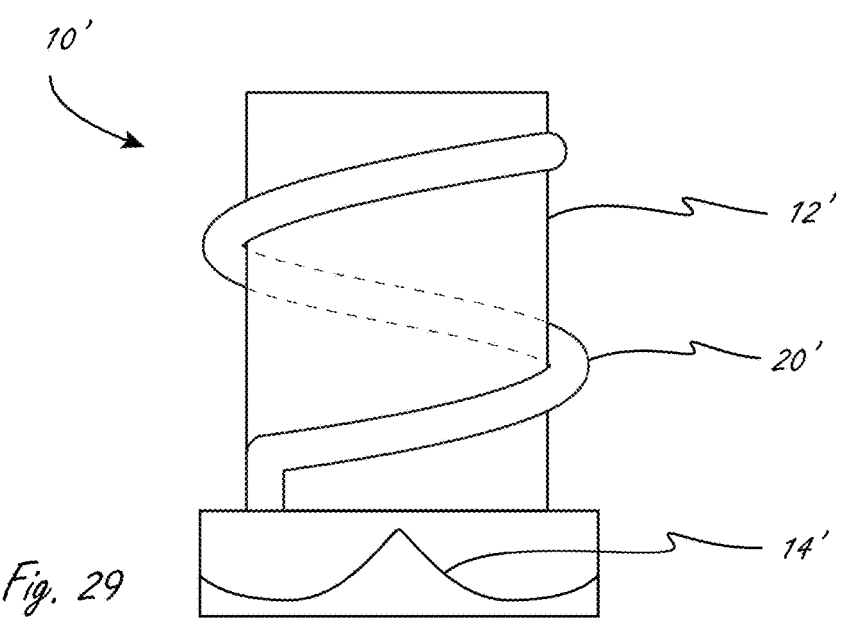
FIG. 29 is a front view of another percutaneous valve similar to the one of FIG. 6, in accordance with embodiments.

FIG. 29 illustrates another embodiment in accordance with the present disclosure. A valve prosthesis 10' includes a helical wire 20' and frame structure 12'. Valve structure 10' is similar to valve 10 except that valve segment 14' is fixed within a separate end of frame structure 12'. Wire 20' is wrapped around a lower portion of the frame structure 12 having a smaller diameter than the upper portion of the frame structure 12 to which the valve segment 14' is fixed.

FIGS. 30A to 30F illustrate several other embodiments in accordance with the present disclosure. Each of valves 10a to 10f includes a helical wire and frame. Each can optionally include a valve segment within the frame.

Figure 30A:
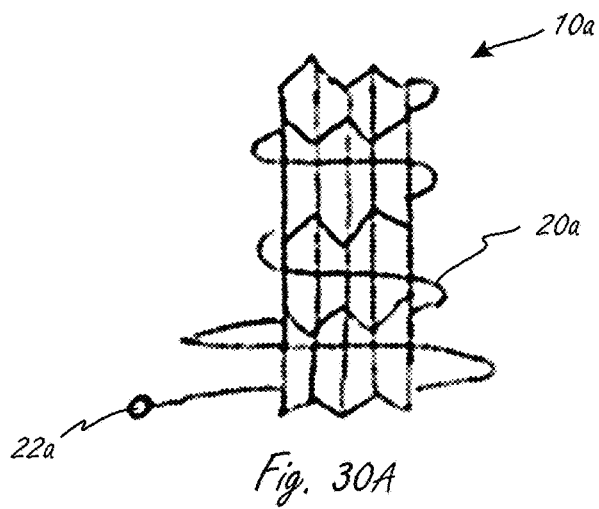
FIGS. 30A-30F are front views of other percutaneous valves similar to the one of FIG. 6, in accordance with embodiments.

FIG. 30A shows a valve prosthesis 10a which is similar to valve prosthesis 10 except that free end 22a includes an atraumatic ball tip. Also, wire 20a has a tubular shape at one end and a frustoconical shape at another end. Frame structure 12a is substantially similar to frame structure 12.

Figure 30B:
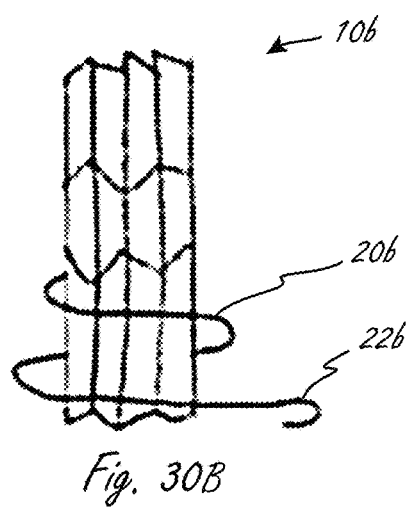

FIG. 30B shows a valve prosthesis 10b which is similar to valve prosthesis 10 except that free end 22 has a pigtail tip. Also, wire 20b is attached to an intermediate portion of frame structure 12b instead of an end of the frame structure 12b. Frame structure 12b is substantially similar to frame structure 12.

Figure 30C:
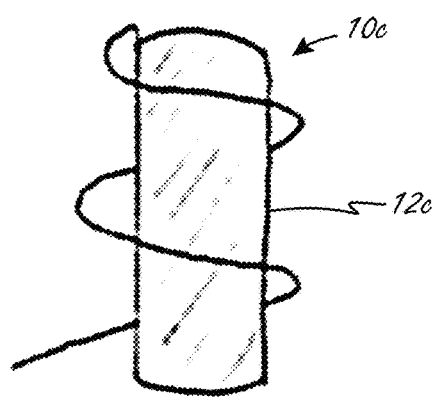

FIG. 30C shows a valve prosthesis 10c which is similar to valve prosthesis 10 except that frame structure 12c is a tubular structure instead of a scaffold or stent-like structure. The frame structure 12c can be formed of expandable materials such as polyurethane or polycarbonate urethane. The wire 20c is substantially similar to wire 20. The free end 22c is substantially similar to free end 22.

Figure 30D:
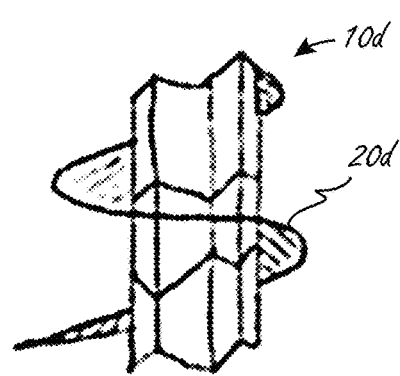

FIG. 30D shows a valve prosthesis 10d which is similar to valve prosthesis 10 except that the anchor 15 is formed of a three-dimensional surface 20d instead of a wire 20. Three-dimensional surface 20d comprises a free end 22d, which may be substantially similar to any of the free ends described herein. Frame structure 12d is substantially similar to frame structure 12.

Figure 30E:
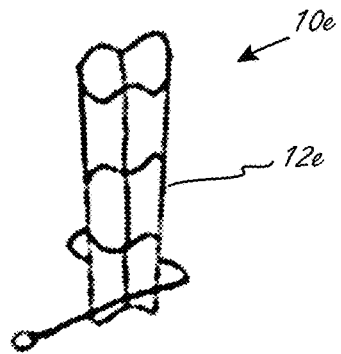

FIG. 30E shows a valve prosthesis 10e which is similar to valve prosthesis 10 except that frame structure 12e has a conical shape instead of a tubular shape. One will appreciate from the description herein that the frame structure 12 may take a variety of shapes in accordance with the present disclosure. The wire 20e is substantially similar to wire 20. The free end 22e is substantially similar to free end 22.

Figure 30F:
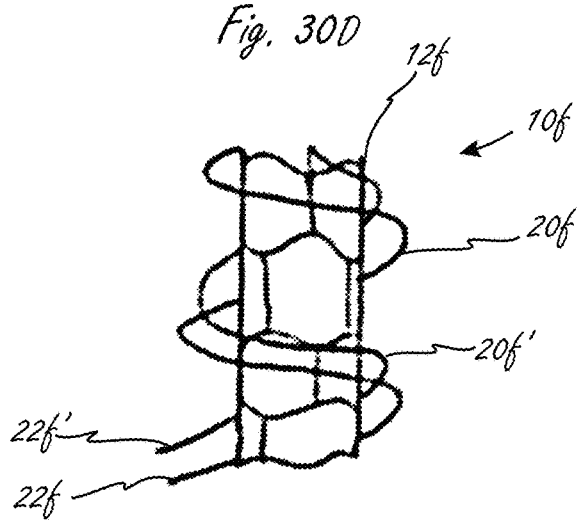

FIG. 30F shows a valve prosthesis 10f which is similar to valve prosthesis 10 except that the valve device 10f includes a plurality of wires 20f and 20c. The use of a plurality of wires 20f and 20f provides increased anchoring security. Because it may be difficult to insert both free ends 22f and 22f, one or both free ends 22f and 22f may include a sharp point for piercing tissue. In this manner, the sharp end can pierce the valve annulus or leaflets. Barbs or other mechanisms may be employed to increase anchoring of the wire. For example, one or both of the wires 20f and 20f may include a braided surface or barbs to prevent axial dislocation once it is screwed into place.

FIGS. 31-35 illustrate another valve prosthesis 10g embodiment which is similar to valve prosthesis 10 except that the valve prosthesis 10g is configured for anchoring from the bottom (i.e., ventricular side) of the native mitral valve annulus. By comparison to valve prosthesis 10, valve prosthesis 10g includes a helical anchor 15g in a frustoconical (or conical) shape with a narrow section at the bottom of the frame structure 12g and a wider section along a central portion of the device 10g. In the illustrated embodiment, the widest section of the anchor 15g is near a top of the coil 15g. In the illustrated embodiment, the coiled anchor 15g extends from a bottom of the frame structure 12g to a top section of the frame structure 12g in the collapsed (e.g., unexpanded) configuration. The frame structure 12g, anchor 15g, and valve segment (not shown) are otherwise generally similar to those of valve 10 or any of the frame structures, anchors, or valve segments described herein.

Figure 6:
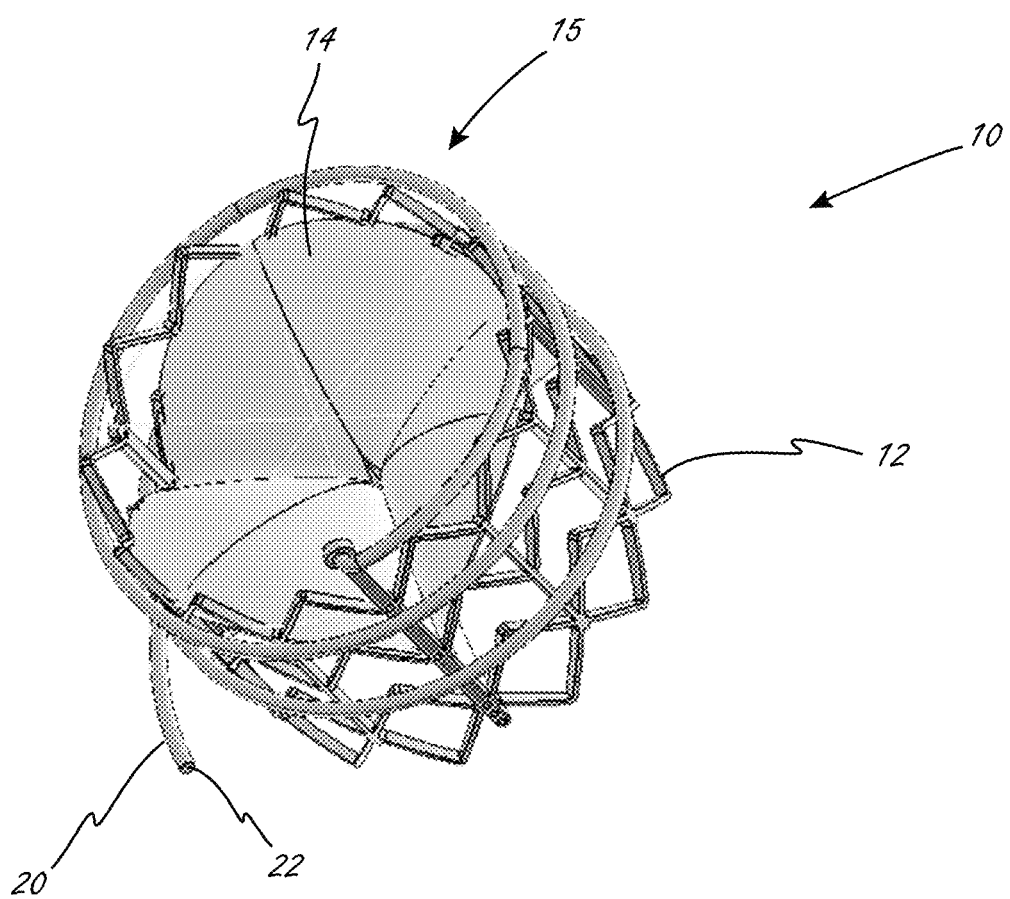
FIGS. 6-10 are several views of a percutaneous valve for replacement of a diseased native valve, in accordance with embodiments.
Figure 7:
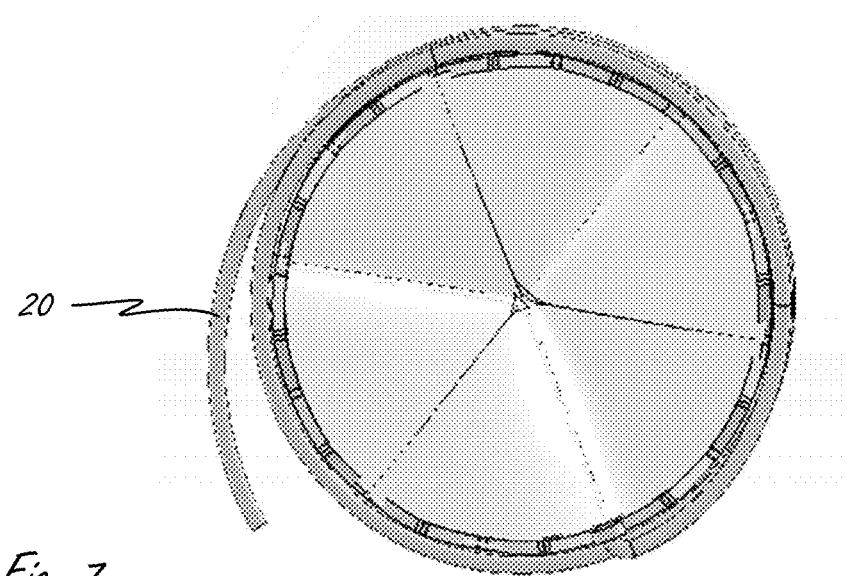
Figure 8:
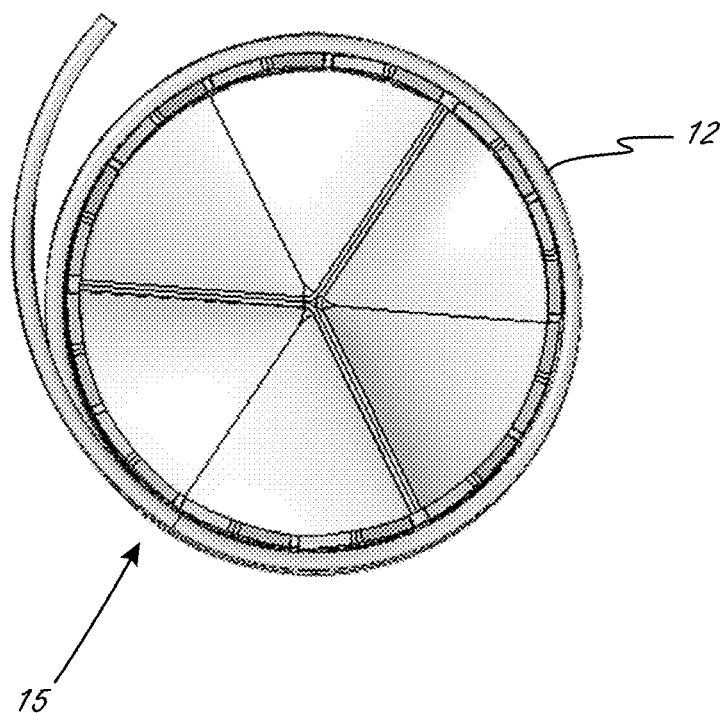
Figure 9:
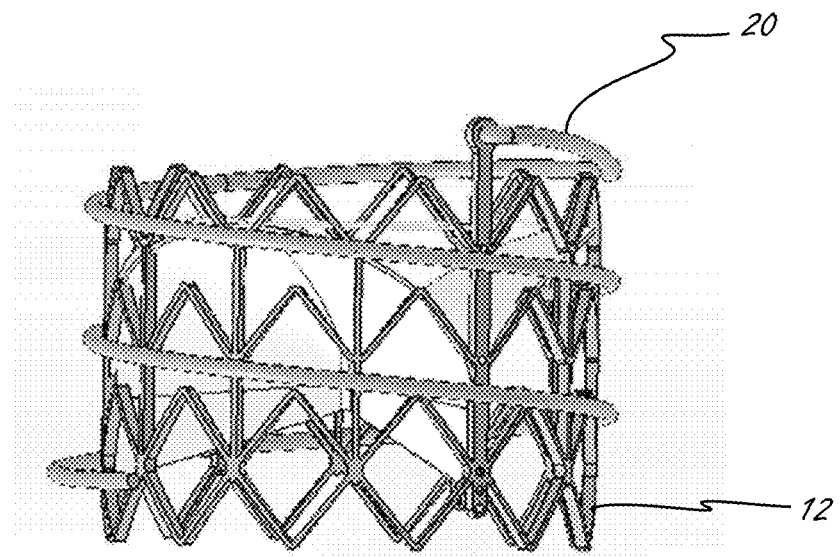
Figure 10:
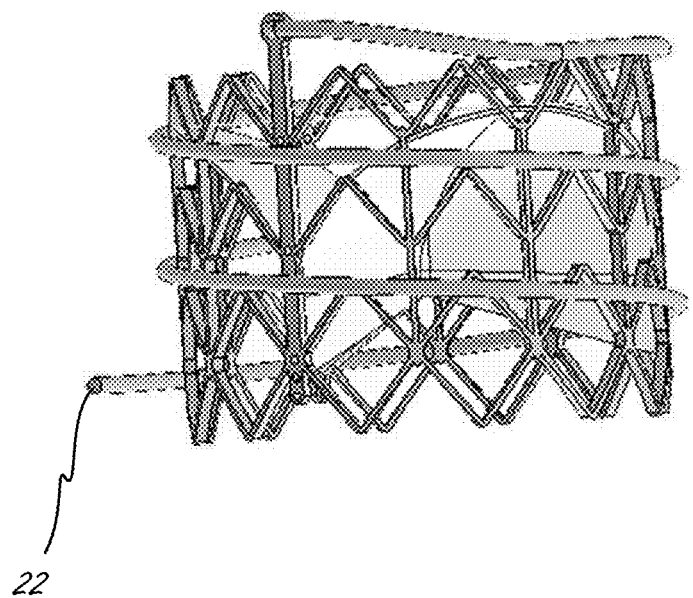

The anchor 15g is inverted compared to anchor 15 in FIG. 6. A free end 22g is positioned along a central section of the valve prosthesis 10g. As will be described below in more detail with reference to FIGS. 43A-43AF, the valve prosthesis device 10g may be configured to be inserted through the native valve (e.g. mitral valve) and anchored from below. In particular, the anchor 15g may be configured to capture the chordae and/or native valve leaflets from below the valve annulus. This inverted design provides a simple transcatheter approach to the diseased native valve while providing a long-term and clinically useful anchoring mechanism.

Figure 35:
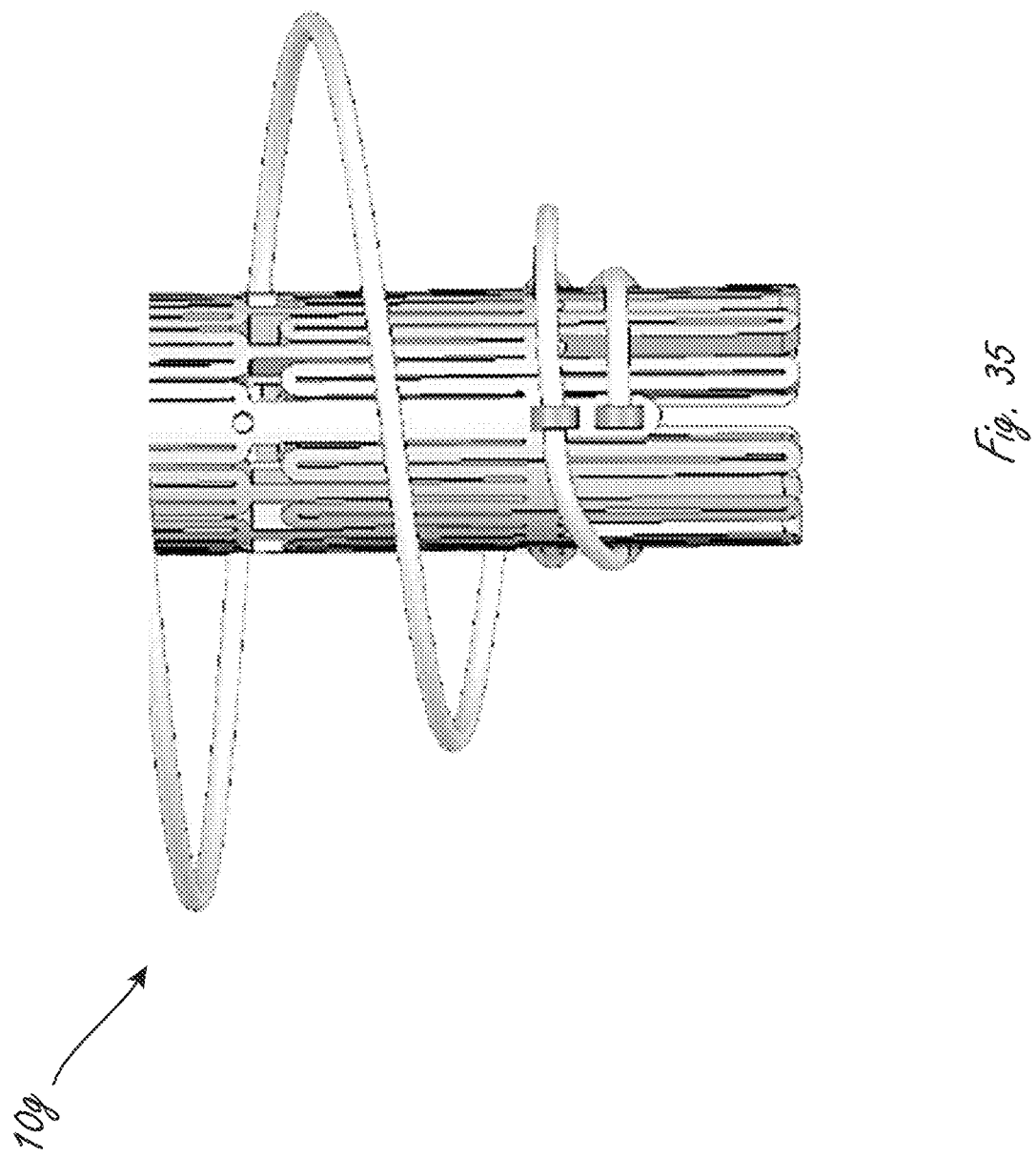
Figure 37:
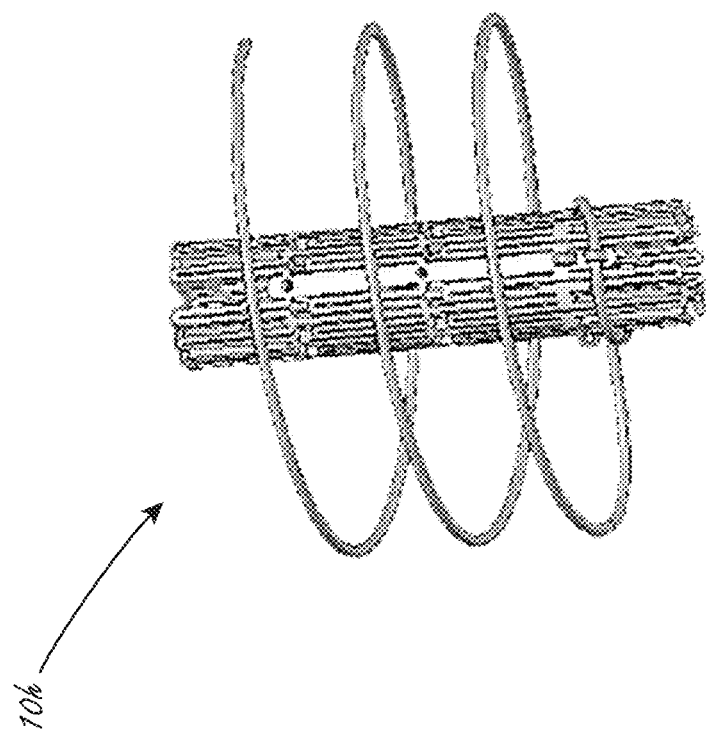
FIGS. 36-39 illustrate another valve device similar to the one of FIG. 6, in accordance with embodiments.
Figure 36:
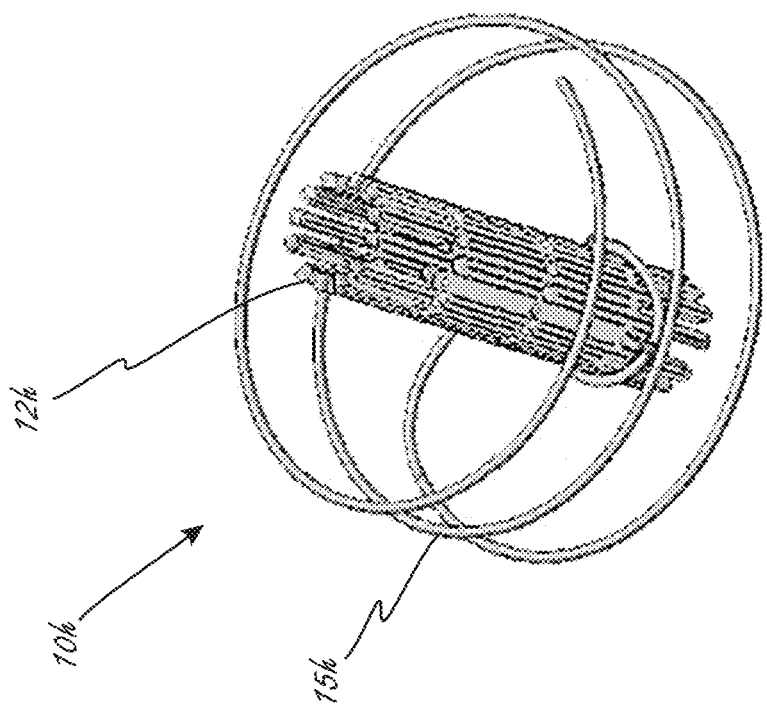
Figure 39:
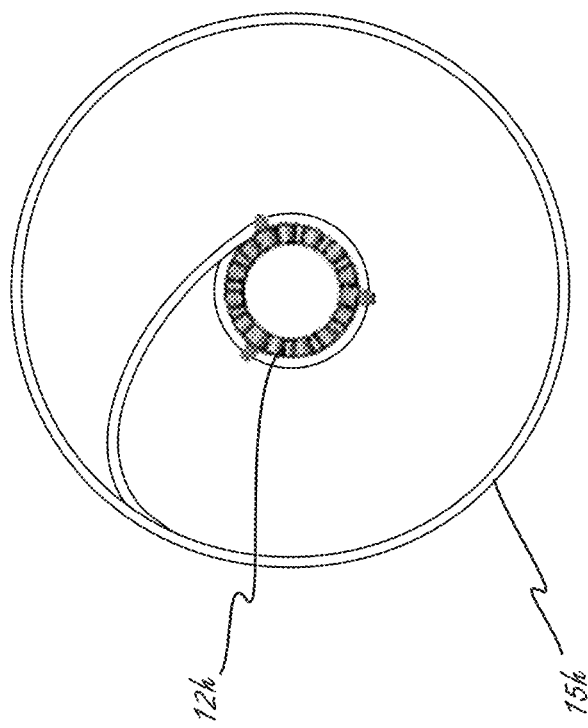
Figure 38:
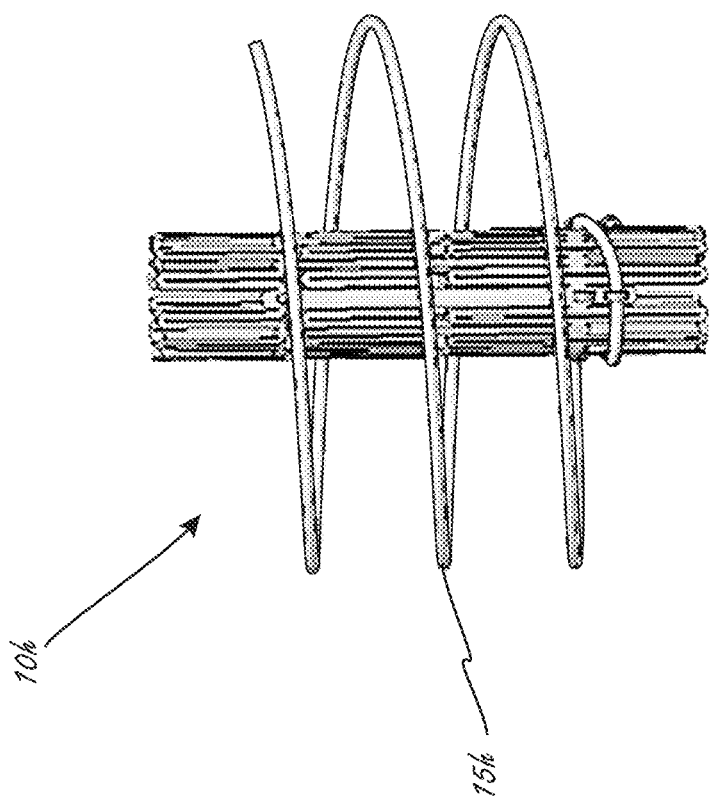

The exemplary anchor 15g is attached to the frame structure 12g at one end 57. In the illustrated embodiment, as best shown in FIG. 35, the end is fixed to a strut of the frame structure 12g. This attached end can be attached by suitable means as would be understood by one of skill in the art from the description herein including, but not limited to, a weld, an adhesive, and a mechanical fastener. In the illustrated embodiment, the valve prosthesis 10g includes optional eyelets 55 for supplemental securement of the coil anchor 15g. The exemplary anchor 15g is formed in the shape of a coil wire similar to the other anchor wires described herein and with a section extending through the eyelets 55. The coil 15g is slidably held within the eyelets 55. The coil 15g may be configured to retain its shape after deployment. As the frame structure 12g is subsequently expanded, the coil wire anchor 15g slides through the eyelets 55 to allow the frame structure 12g to expand within the larger diameter of the anchor 15g. The eyelets 55 hold the coil wire anchor 15g in a radial position relative to the frame structure 12g. This may mitigate against the risk of the coil 15g bending away from the frame structure 12g and/or fracture failure.

Figure 32:
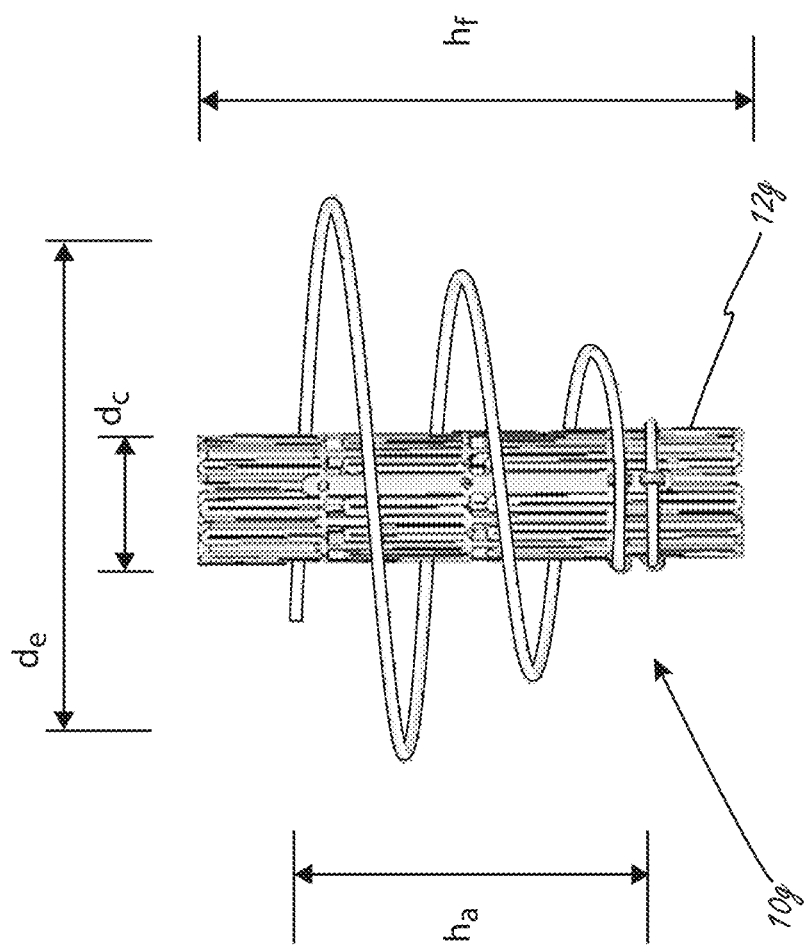
Figure 31:
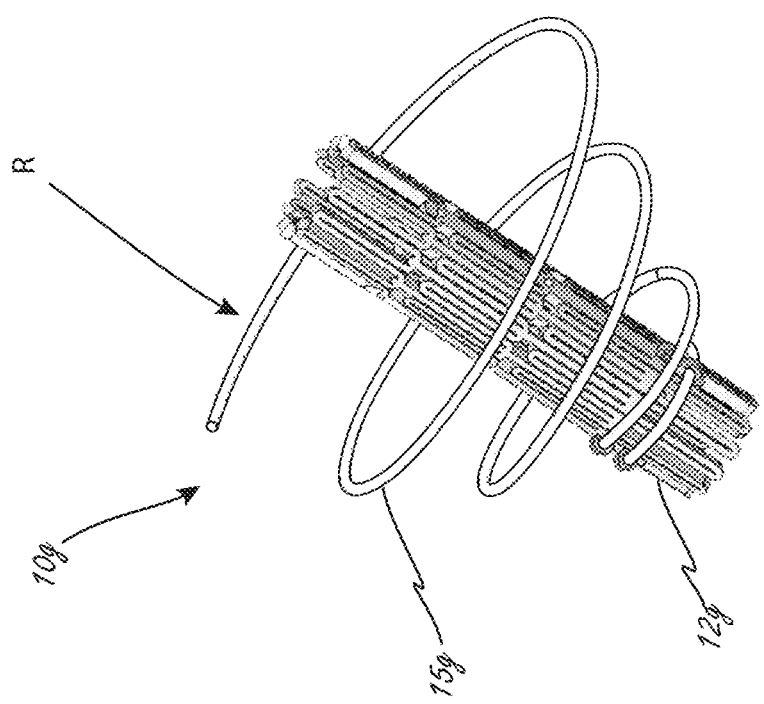

With continued references to FIGS. 31-32, in an exemplary embodiment, the anchor 15g has a radius of curvature (R) is between about 15 mm and about 50 m. In various embodiments, R is about 35 mm. In various embodiments, the height of the anchor ($H_a$) is between about 10 mm and about 60 mm. In various embodiments, the height of the anchor ($H_a$) is between about 3 mm and about 60 mm. In various embodiments, the height of the anchor ($H_a$) is between about 3 mm and about 6 mm. In various embodiments, the height of the anchor ($H_a$) is between about 3 mm and about 50 mm. In various embodiments, $H_a$ is about 30 mm. In various embodiments, the height of the frame structure ($H_f$) is between about 20 mm and about 55 mm. In various embodiments, $H_f$ is about 30 mm. In various embodiments, the width of the frame structure in a collapsed configuration ($W_c$) is between about 4 mm and about 8 mm. In various embodiments, $W_c$ is about 6 mm. In various embodiments, the width of the frame structure 12g in an expanded configuration ($W_e$) is between about 25 mm and about 35 mm. In various embodiments, $W_e$ is about 30 mm. In various embodiments, the anchor 15g is formed as a coil with varying widths and the minimum width (or radius) is about 10 mm and the maximum radius is about 30 mm.

It will be understood by one of ordinary skill in the art that any of the anchor embodiments described herein may be formed with similar dimensions as those described herein with reference to anchor 15g, or any of the other anchors described herein.

It will be understood by one of ordinary skill in the art that any of the frame structure embodiments described herein may be formed with similar dimensions as those described herein with reference to frame structure 12g, or any of the other frame structures described herein.

FIGS. 36-39 illustrate another valve prosthesis 10h embodiment which is similar to valve prosthesis 10g except that the anchor 15h has a generally symmetrical tubular profile. A proximal end 57h of anchor 15h extends inwardly from the coil body to an attachment point on the frame structure 12h. The end 57h wraps around the frame structure 12h and is fixed to the frame structure 12h as described herein. The coil 20h can have a portion of a turn around the collapsed frame structure 12h. The coil 20h can have one or more turns around the collapsed frame structure 12h. A portion of the coil 20h may extend through eyelets 55h as described herein. Similar to valve 10g, the frame structure 12g may be allowed to expand by the coil anchor 15g sliding through the eyelets 55h. At the same time, the eyelets 55h may maintain a relative radial position of the respective portion of the coil anchor 15g. Although the embodiment shows eyelets 55g, one of ordinary skill in the art will appreciate from the description herein that other mechanisms may be suitable for guiding the anchor 15g including, but not limited to, hooks and guiderails or the like, or any combination thereof.

FIGS. 40-42 illustrate exemplary valve prosthesis embodiments 10i, 10j, and 10k which are similar to valve prosthesis 10g and having anchors 15i, 15j, and 15k of varying configurations. In the illustrated embodiments, the exemplary anchors include an atraumatic tip 60 as described herein.

FIG. 40 illustrates a valve prosthesis 10i which is similar to valve prosthesis 10g except that the anchor 15i does not have a linear or symmetrical shape. At least a portion of anchor 15i has a tapered shape. In the illustrated embodiment, the anchor 15i is formed as a coil and at least one turn of the windings has a curvilinear shape. Whereas at least some of the turns in the windings of anchor 10g are generally flat in a plane, the respective turns in the valve prosthesis 10i are configured to extend out of the plane in a three-dimensional, degenerate surface. In the illustrated embodiment, the curvilinear shape is more pronounced, and the radius of curvature is greater, on the turn at the top than the turns at the bottom. The overall shape of anchor 15i is generally conical. This shape may promote insertion of the anchor through the native valve leaflets as will be described in more detail below.

FIG. 41 illustrates a valve prosthesis 10j which is similar to valve prostheses 10g, 10h, 10i, and 10j. Anchor 15j is formed as a coil with a complex, tapered shape. FIG. 41 illustrates a valve prosthesis 10k which is similar to valve prostheses 10g, 10h, 10i, and 10j except that the anchor 15k is configured for facilitating easier insertion through the native valve. In the illustrated embodiment, the anchor 15k is formed as a coil with a relatively smaller form factor than the other anchors. The smaller radial width of the coil may promote insertion through the native valve while still having sufficient width to capture a necessary number of chordae and/or the native valve leaflets.

Any of the anchor embodiments described herein may have windings with varying shapes and curvatures. In various embodiments, a lower portion of the anchor has windings which curve in a first direction and an upper portion has windings which curve in a second direction (in planes generally perpendicular to a major axis of the frame structure and/or anchor). In various embodiments, the second direction is opposite the first direction. In various embodiments, the anchor includes a first portion having a first radius of curvature (in a plane generally perpendicular the major axis of the frame structure and/or anchor), and a second portion having a second radius of curvature. In various embodiments, the anchor includes a third portion having a third radius of curvature. In various embodiments, the anchor includes a fourth portion having a fourth radius of curvature. In various embodiments, the anchor includes a plurality of portions each having a unique radius of curvature. In various embodiments, the respective radii of curvature are all different. In various embodiments, the second radius of curvature is greater than the first, and the third radius of curvature is greater than the second. In various embodiments, the radius of curvature of the upper windings is greater than 30 mm. In various embodiments, the radius of curvature of the lower windings is greater than 10 mm.

FIG. 42 illustrates an exemplary modality for attachment of the anchor 15j to a frame structure 12j. In various embodiments, the anchor 15j is welded to the frame structure 12j, for example, to one of the struts of the frame structure 12j. In various embodiments, one end of the anchor 15j is configured to extend inside the frame structure 12j where it is mechanically fastened. In the embodiment illustrated in FIG. 42, the anchor 15j is fixed to a bottom-most (inferior) end of the frame structure 12j.

A method of using a valve device similar to valve devices 10g, 10h, 10i, 10j, 10k, 10l, 10m, 10n, 10o, 10p, etc. will now be described with reference to FIGS. 43A to 43AF.

Figure 43B:
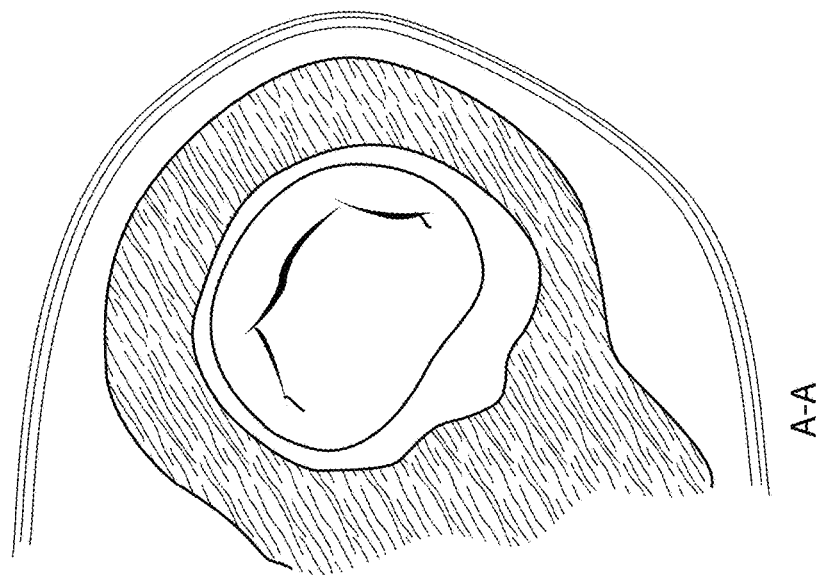
FIGS. 43A-43AF are sequential views of a method of implanting a device similar to the one of FIGS. 6 and 31, in accordance with embodiments.
Figure 43A:
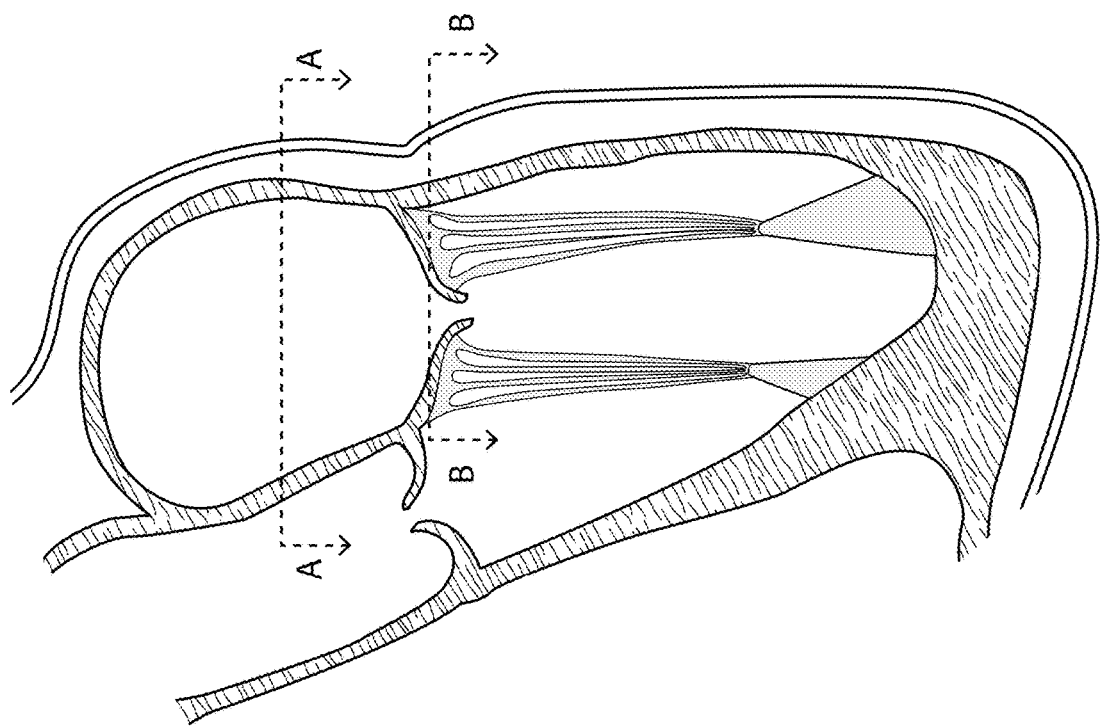

FIGS. 43A-43AF show sequential views of a method of implanting a valve prosthesis 10 using a delivery device 30'. The valve prosthesis 10 may be similar to any of the valve prostheses described herein or understood by one of ordinary skill in the art from the description herein. For example, valve prosthesis 10 may be substantially similar to the valve prosthesis 10g shown in FIGS. 31-35 and may comprise a frame structure 12g and anchor 15g as described herein. The delivery device 30' may be substantially similar to any of the delivery devices described herein or understood by one of ordinary skill in the art from the description herein. The delivery device 30' may comprise an inner shaft or delivery tube 52 as described herein. The delivery device 30' may optionally comprise an outer shaft or outer catheter 50, a guidewire 54, and/or an inflatable balloon 48, in any combination thereof as desired by one of ordinary skill in the art. Not all elements are labeled in each of FIGS. 43A-43AF in order to make the illustrations less cluttered and easier to see.

While the method shown in FIGS. 43A-43AF is described in relation to a mitral valve replacement procedure, it will be understood by one of ordinary skill in the art that the methods described herein may be applied to a variety of procedures or anatomical areas, for example other atrioventricular valves of the heart or the like. For example, the methods described herein may be applied to replacement of a diseased aortic valve or tricuspid valve.

Figure 43D:
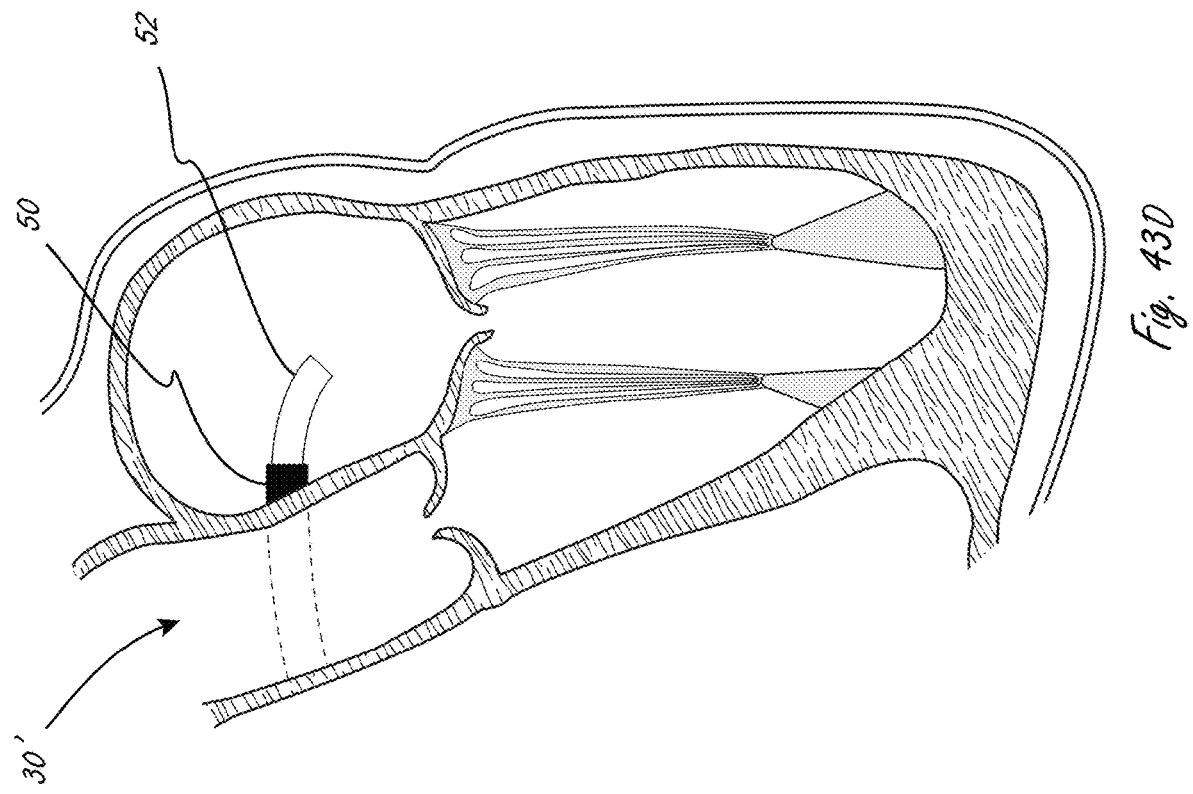
Figure 43C:
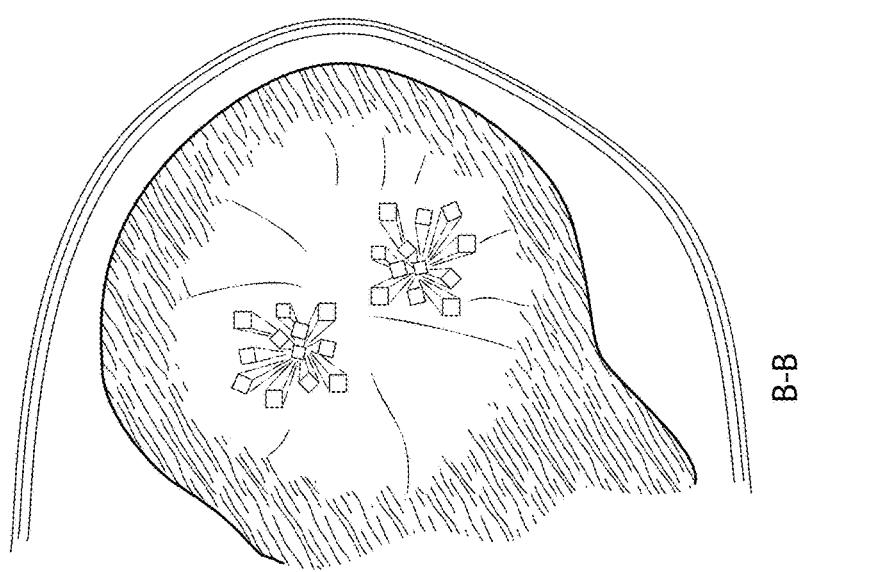
Figure 43F:
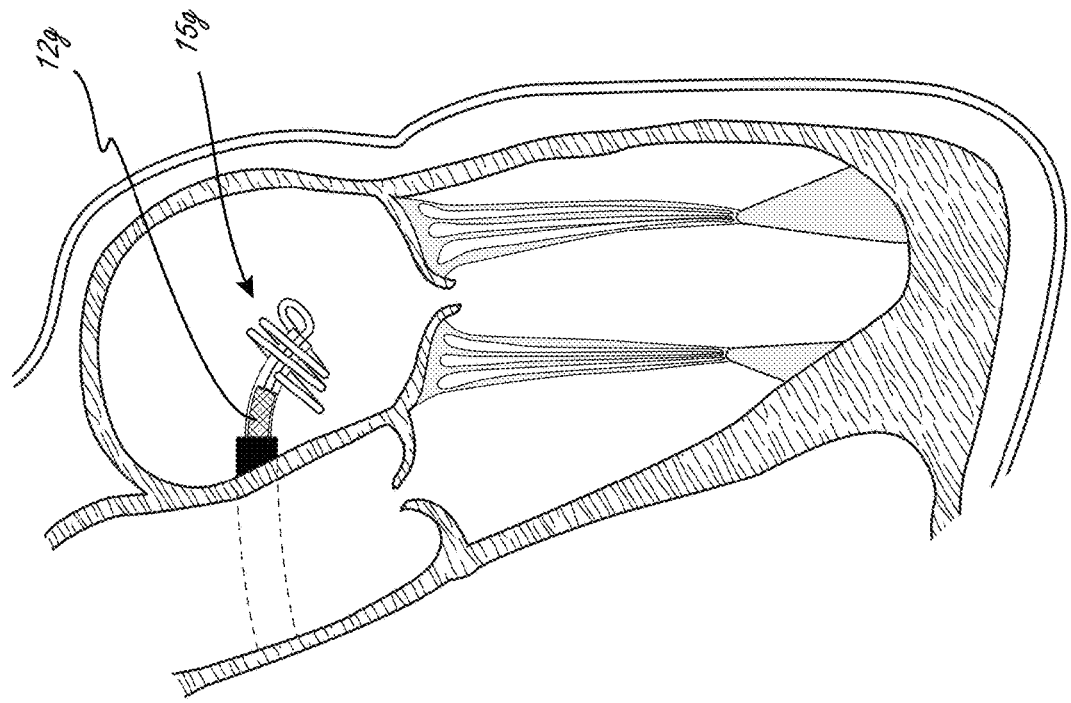
Figure 43E:
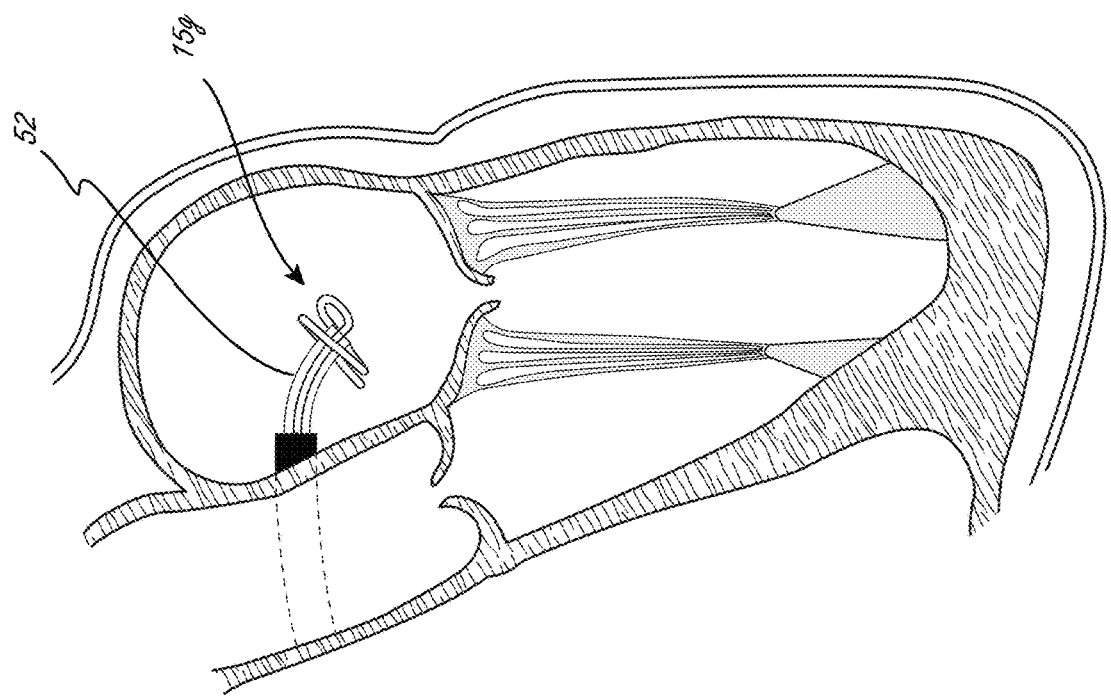

FIGS. 43A-43C shows various cross-sectional views of a heart 2 having a diseased mitral valve 4 which may be treated using the devices, systems, and methods described herein. The mitral valve 4 sits between the left atrium 25 and the left ventricle 26 and, when functioning properly, allows blood to flow from the left atrium 25 to the left ventricle 26 while preventing backflow or regurgitation in the reverse direction. As shown in FIG. 43A, the native valve leaflets 42 of the diseased mitral valve 4 do not fully prolapse and the patient experiences regurgitation. FIG. 43B shows a cross-sectional view of the heart 2 taken along line A-A, shown in FIG. 43A, which shows the native valve leaflets 42 of the mitral valve 4 from the viewpoint of the left atrium 25. FIG. 43C shows a cross-sectional view of the heart 2 taken along line B-B, shown in FIG. 43A, which shows the chordae tendineae 40 of the left ventricle 26.

As shown in FIG. 43D, a distal end of the delivery device 30' may be inserted into the left atrium 25 of the heart 2 via a transseptal puncture as described herein. For example, the distal ends of inner shaft 52 and/or outer sheath 50 may be advanced into the left atrium 25 of the heart 2. The inner shaft 52 may optionally be advanced distally into the left atrium 25 away from the distal end of the outer sheath 50. In some embodiments, advancing the inner shaft 52 relative to the outer sheath 50 may aid in deployment and/or placement of the valve prosthesis 10g as described herein. Alternatively, both the inner shaft 52 and the outer sheath 50 may be advanced distally into the left atrium 25 through the transseptal puncture.

Figure 43H:
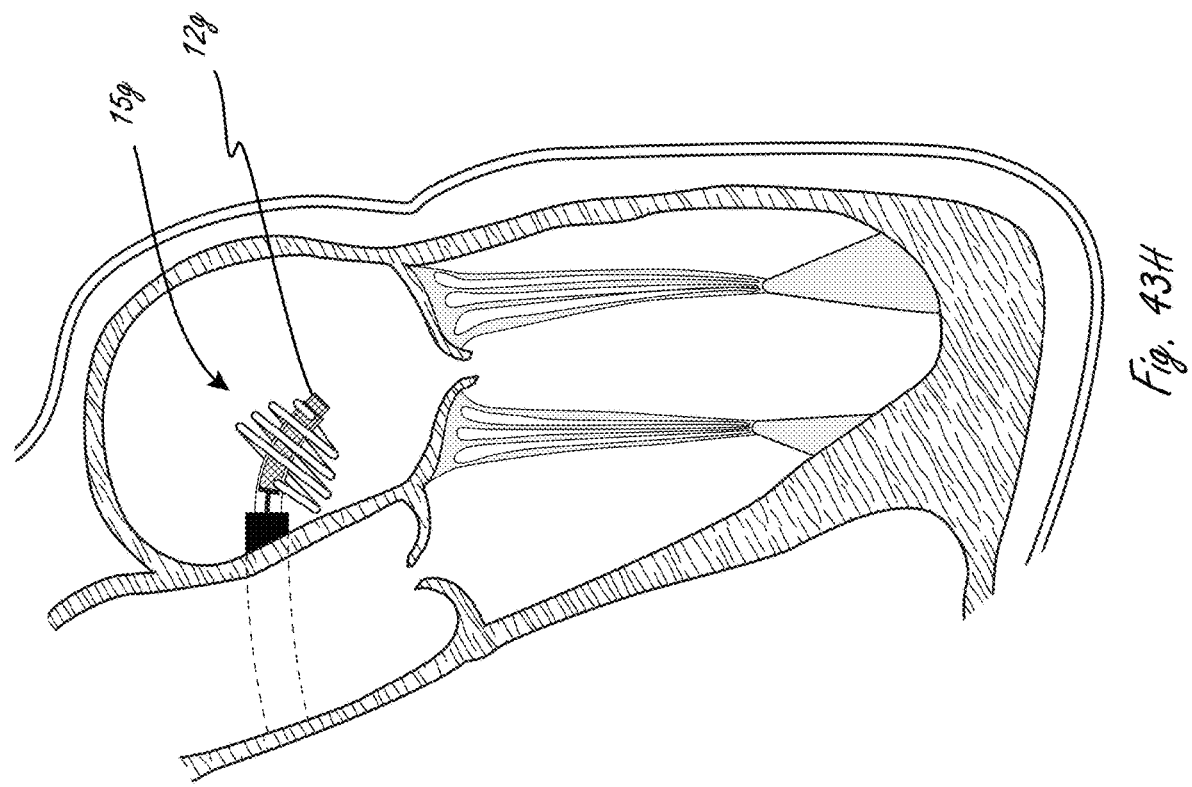
Figure 43G:
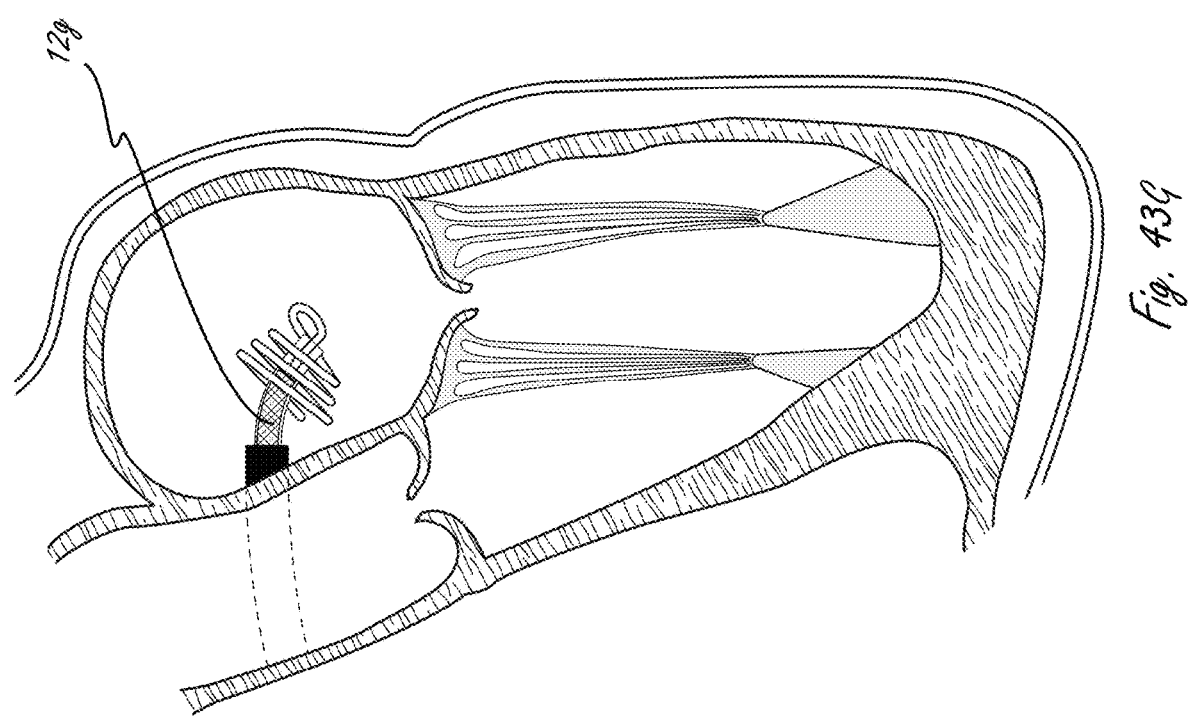

FIGS. 43E-43H show deployment of the anchor 15g from the distal end of the delivery device 30'. As described herein, at least a portion of the valve prosthesis 10g may be deployed from an undeployed (for example, compressed or unexpanded) configuration to an expanded configuration within the left atrium 25. At least a portion of the anchor 15g may be deployed from a delivery and/or elongated configuration to a deployed configuration within the heart. For example, anchor 15g may be actuated from an elongated configuration (e.g., from a straightened shape) to a deployed configuration (e.g., a pre-formed shape for implantation, such as a spiral, helical, or conical shape) within the left atrium 25 as described herein. In some embodiments, the anchor 15g may be deployed from the inner shaft 52 by pushing the anchor 15g out of the inner shaft 52, releasing the anchor 15g from radial constraint by retracting the outer sheath 50, or the like as described herein. In some embodiments, the anchor 15g may be pushed out the inner shaft 52 using a pusher on a proximal handle (not shown) located outside the body. After the anchor 15g has been deployed from the delivery device 30', the frame structure 12g may be at least partially deployed from the delivery device 30' as shown in FIG. 43H so as to place the frame structure 12g within the anchor 15g. The frame structure 12g may be deployed from the delivery device 30' in either the unexpanded configuration or the expanded configuration, depending on the location of deployment, as will be understood by one of ordinary skill in the art based on the teachings herein.

Figure 43J:
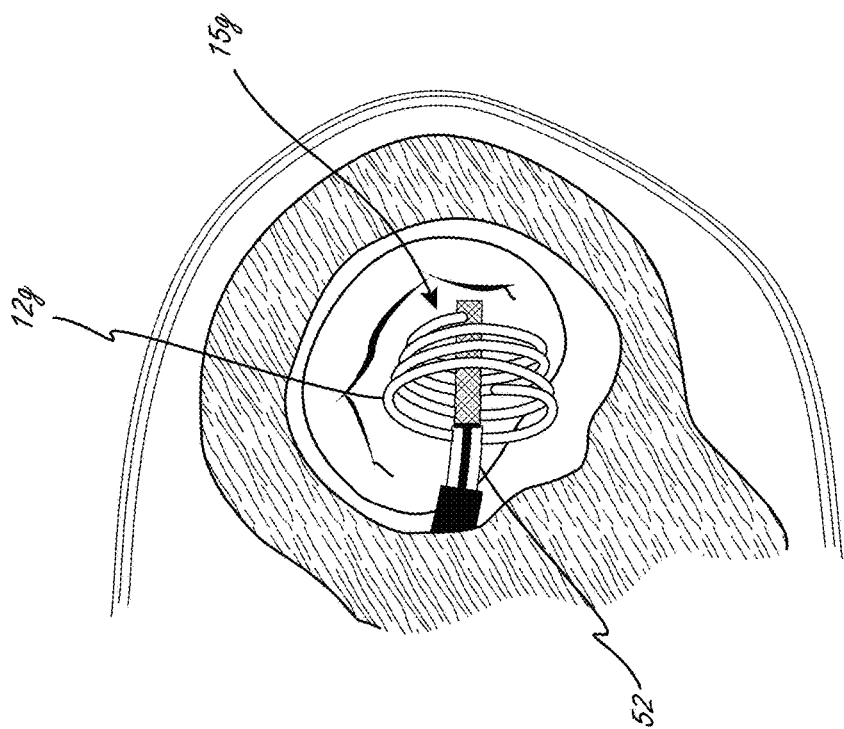
Figure 43I:
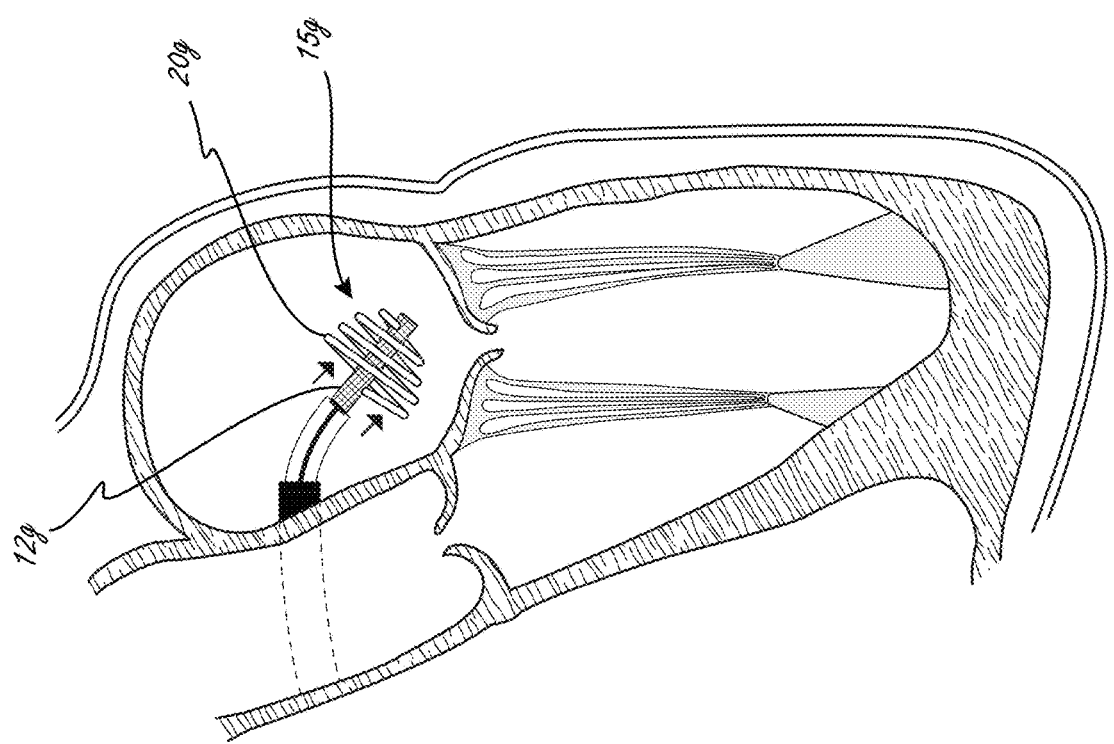

FIGS. 43I-43K show advancement of the valve prosthesis 10g, with anchor 15g deployed around the unexpanded frame structure 12g, towards the native valve 4 requiring treatment. The distal end of the delivery device 30' (for example, the distal end of the inner shaft 52 and/or the outer sheath 50) may be steered such that the distal end of the delivery device 30' points toward the atrial side of the native valve 4. Such steering may occur prior to, during, or after deployment of at least a portion (for example deployment of an anchor 15g) of the valve prosthesis 10g. In some embodiments, the distal end of the outer sheath 50 may be steerable. Alternatively, or in combination, the inner shaft 52 may comprise a joint configured to change an angle of the distal portion of the inner shaft 52 relative to a proximal portion of the inner shaft 52. The inner shaft 52 may be steered by changing the angle of the distal portion of the inner shaft 52 relative to the proximal portion of the inner shaft 52. The angle of the joint may be changed passively or actively. In various embodiments, the angle may be selectively controlled by a proximal handle. For example, pull wires or other mechanisms may connect to the joint to controls on the handle.

FIGS. 43L-43P show the valve prosthesis 10g being advanced through the native valve 4 by the delivery device 30' from the left atrium 25 to the left ventricle 26. Advancement of the valve prosthesis 10g and optionally delivery device 30' through the mitral valve 4 may be facilitated by the natural opening and closing of the valve 4 during the cardiac cycle. The distal end of the delivery device 30' and/or valve prosthesis 10g may be configured to be advanced from a first side of a native valve to a second side of the native valve. For example, the distal end of the delivery device 30' and/or valve prosthesis 10g may be advanced from a left atrial side of a mitral valve 4 to a left ventricular side of a mitral valve 4. Advancing the anchor 15g may comprise pushing the anchor 15g through the native valve 4. Alternatively, or in combination, advancing the anchor 15g may comprise rotating the anchor 15g through the native valve 4. In some instance, the combination of rotational motion and pushing may facilitate advancement of the device from the first side of the native valve 4 to the second side of the native valve 4. Rotation of the valve prosthesis 10g, for example rotation of the anchor 15g and/or frame structure 12g, may be facilitated by the inner shaft 52 described herein. For example, the inner shaft 52 may transmit rotational motion to the valve prosthesis 10g in order to rotate the valve prosthesis 10g during advancement through the native valve 4.

Figure 43P:
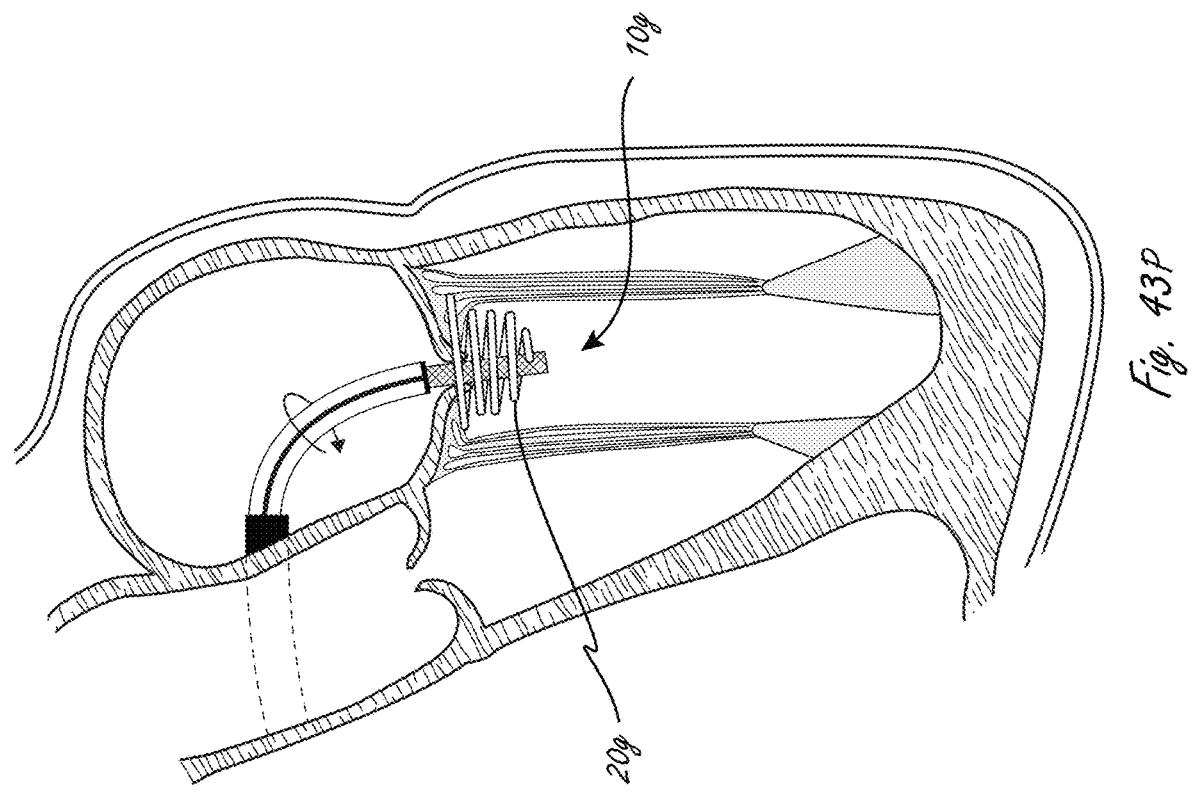
Figure 43O:
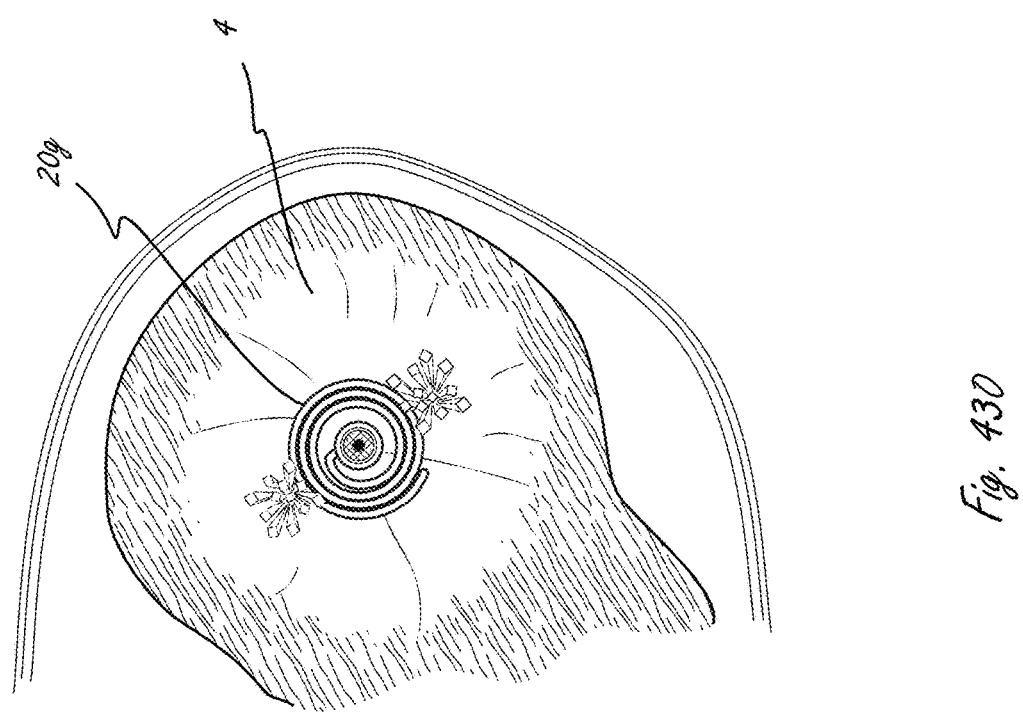

In some instances, advancing the anchor 15g through the native valve 4 may cause the anchor 15g to be stretched or elongated as shown in FIG. 43M. Rotation of the anchor 15g during advancement may assist with the stretching process by aiding in unwinding the anchor 15g. Additionally, the rotational motion may reduce the risk of the free end 22g of the anchor 15g undesirably engaging other anatomy during insertion through the native leaflets 43. The anchor 15g may be sufficiently elastic so as to enable relatively easy insertion through the native valve 4 and/or reduce the risk of injury to the native leaflets 43. At the same time, the anchor may be sufficiently rigid for guiding through and anchoring to the structures in the heart. After the anchor 15g has stretched through the native valve 4 it may return to the deployed configuration as shown in FIG. 43N. FIGS. 43O-43P show the position of the valve prosthesis 10g within the ventricle 26 and, in particular, the position of the anchor 15g relative to the native chordae tendineae 40 and native valve annulus.

In some embodiments, the anchor 15g may be advanced into the ventricle after being fully deployed from the delivery (e.g., elongated) configuration to the deployed configuration.

In some embodiments, the anchor 15g may be advanced into the ventricle before being deployed from the delivery (e.g., elongated) configuration to the deployed configuration.

Figure 43R:
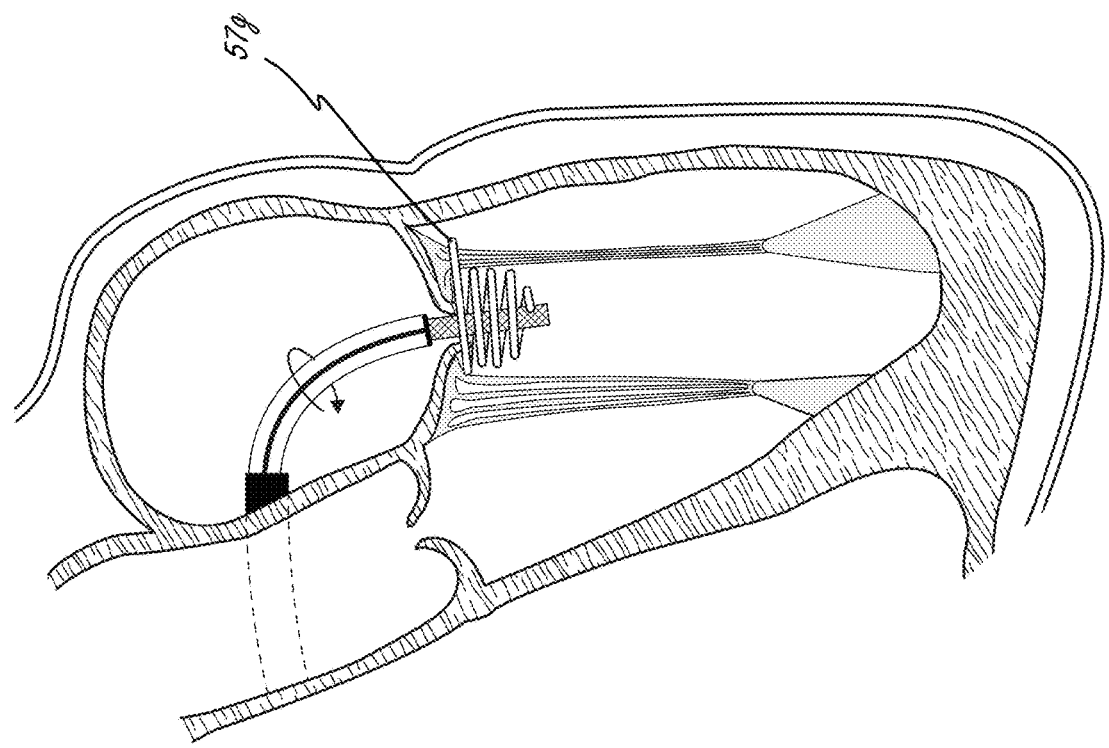
Figure 43Q:
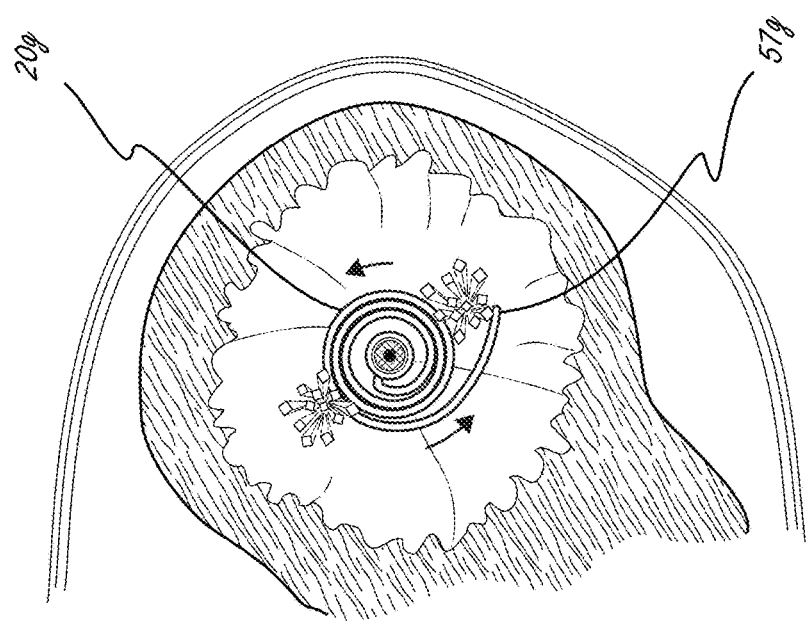
Figure 43T:
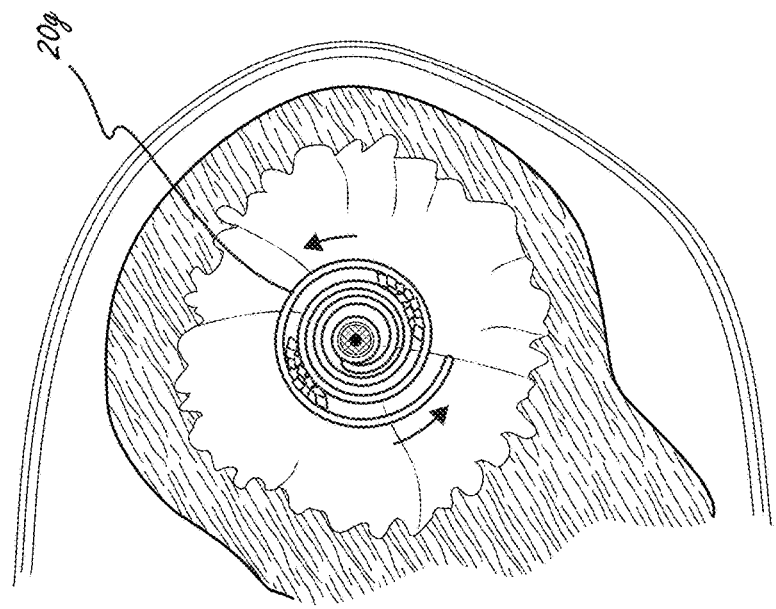
Figure 43S:
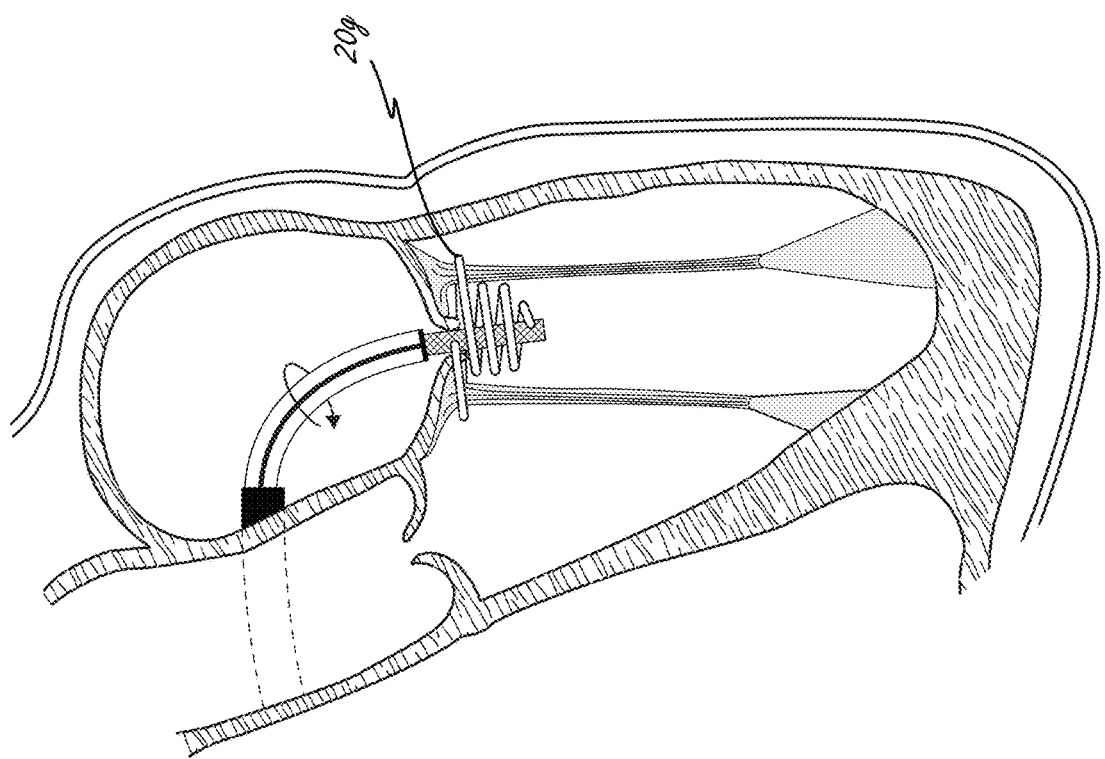

FIGS. 43Q-43T show rotation of the valve prosthesis 10g around one or more structures on the ventricular side of the mitral valve 4. The one or more structures may comprise one or more valve leaflets 43 and/or one or more chordae tendineae 40. After the anchor 15g has been at least partially deployed within the left ventricle 26 adjacent one or more chordae tendineae 40, the valve prosthesis 10g may be rotated to capture and anchor the native chordae 40 and/or native leaflets 43. The free end 22g of the anchor 15g may extend radially outward from the rest of the anchor 15g to facilitate capture of the native structures. The free end 22g of the coil 15g may be rotated around one or more of the chordae tendineae 40 as shown in FIGS. 43Q-43R. Additional rotation of the valve coil 15g may gradually capture additional chordae tendineae 40 as shown in FIGS. 43S-43T.

Rotation of the valve prosthesis 10g, for example, rotation of the anchor 15g and/or frame structure 12, may be facilitated by the delivery device 30' described herein. For example, the inner shaft 52 may be rotated and rotational motion may be transmitted from the inner shaft 52 to the valve prosthesis 10g in order to rotate the valve prosthesis 10g around one or more of the structures on the ventricle side of the mitral valve 4 as described herein.

In some embodiments, the valve prosthesis 10g, for example anchor 15g, may be counter-rotated in order to reposition the anchor 15g with respect to the chordae tendineae 40 before continuing the rotation in the first direction. For example, counter-rotation may be applied if the chordae tendineae 40 are caught by the free end of the anchor 15g (or another part of the valve prosthesis 10g or delivery device 30) during the initial rotation. In such instances, counter-rotation may enable to the clinician to disengage some or all of the chordae tendineae 40 to reduce the stress or torque on the chordae tendineae 40 (e.g., by adjusting the position of the valve prosthesis 10g) before resuming rotation. As another example, the anchor 15g may encounter friction or other resistance to rotation. In this case the clinician may counter-rotate the anchor 15g to return to the original position and then begin rotating the anchor 15g to re-start and/or continue encircling chordae tendineae 40. Rotation and counter-rotation may be applied as many times as desired by the clinician in order to properly position the anchor 15g around the valve structures.

Figure 43V:
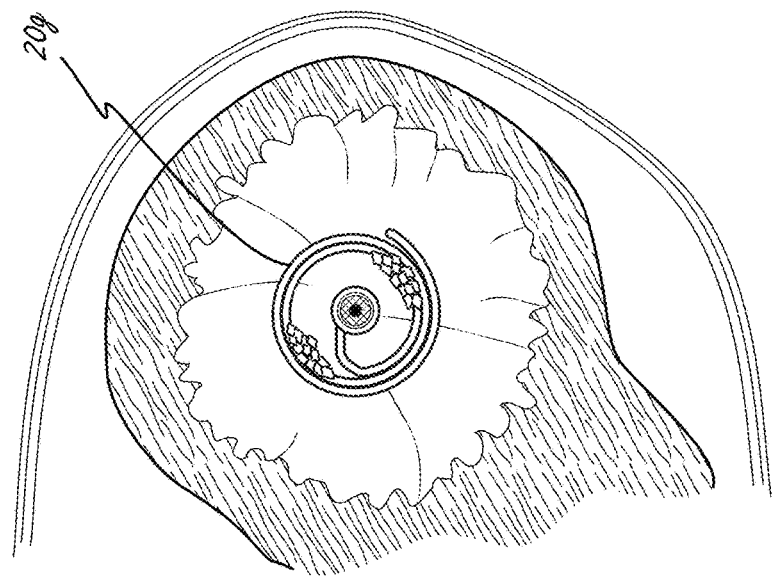
Figure 43U:
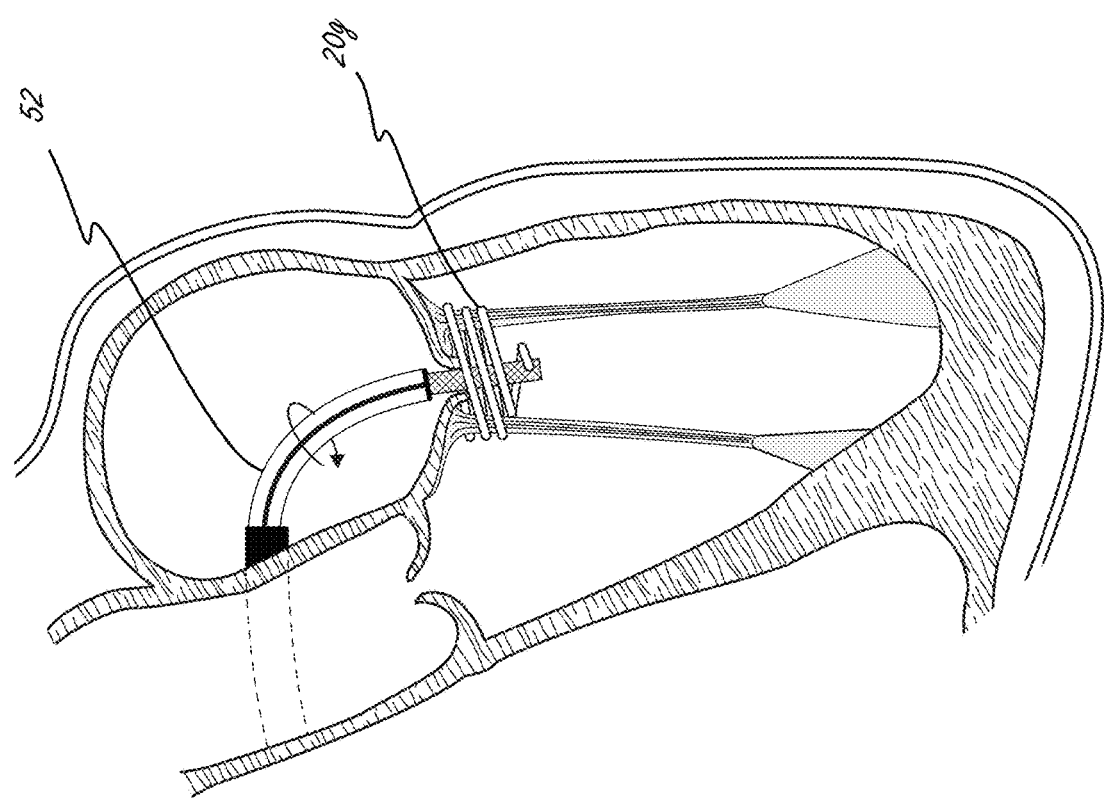

FIGS. 43U-43V show the valve prosthesis 10g wrapped around the captured chordae tendineae 40. The valve prosthesis 10g may be rotated around the chordae tendineae 40 such that the chordae tendineae 40 are pulled inwardly into bunches. As shown in FIG. 43U, the native valve leaflets 43 may also be in communication with the valve prosthesis 10g. The valve prosthesis 10g may be rotated to capture enough chordae tendineae 40 and/or valve leaflets 43 to rigidly anchor the anchor 15g adjacent the native valve annulus. The valve prosthesis 10g may be anchored by wrapping around only a portion of the chordae 40. Although it may be possible to capture all or substantially all the chordae 40, this may not be necessary to provide sufficient anchoring of the prosthesis 10g. As described further herein, the prosthesis may be further anchored by expansion of the frame structure 12g within the native valve and against the anchor 15g.

In some embodiments, the anchor 15g may be deployed such that at least a portion of the anchor 15g resides within a subvalvular plane. For example, at least 50%, 60%, 70%, 80%, 90%, 100% of the anchor 15g may reside within the subvalvular plane after being deployed. The subvalvular plane may be located at the posterior valve annulus, below the valve annulus and around the native valve leaflets 43, and/or parallel to a plane within at least three points of the plane in which the valve annulus resides. In some instances, the anchor 15g may be rotated in the subvalvular plane around the chordae tendineae 40. In some instances, the anchor 15g may be rotated in a plane below to the subvalvular plane in order to encircle the chordae tendineae 40 before the anchor 15g is moved into the subvalvular plane (e.g., by pulling the anchor 15g into the sub-annular space).

Once the anchor 15g has been anchored adjacent to the native valve 4, the frame structure 12g and prosthetic valve segment 14 may be expanded at least partially within the anchor 15g as described herein. The frame structure 12g and the valve segment 14g may be deployed (e.g., expanded) simultaneously. Alternatively, or in combination, the frame structure 12g and the valve segment 14g may be deployed sequentially, for example by first expanding the frame structure 12g and then receiving the prosthetic valve segment 14g therein.

Figure 43X:
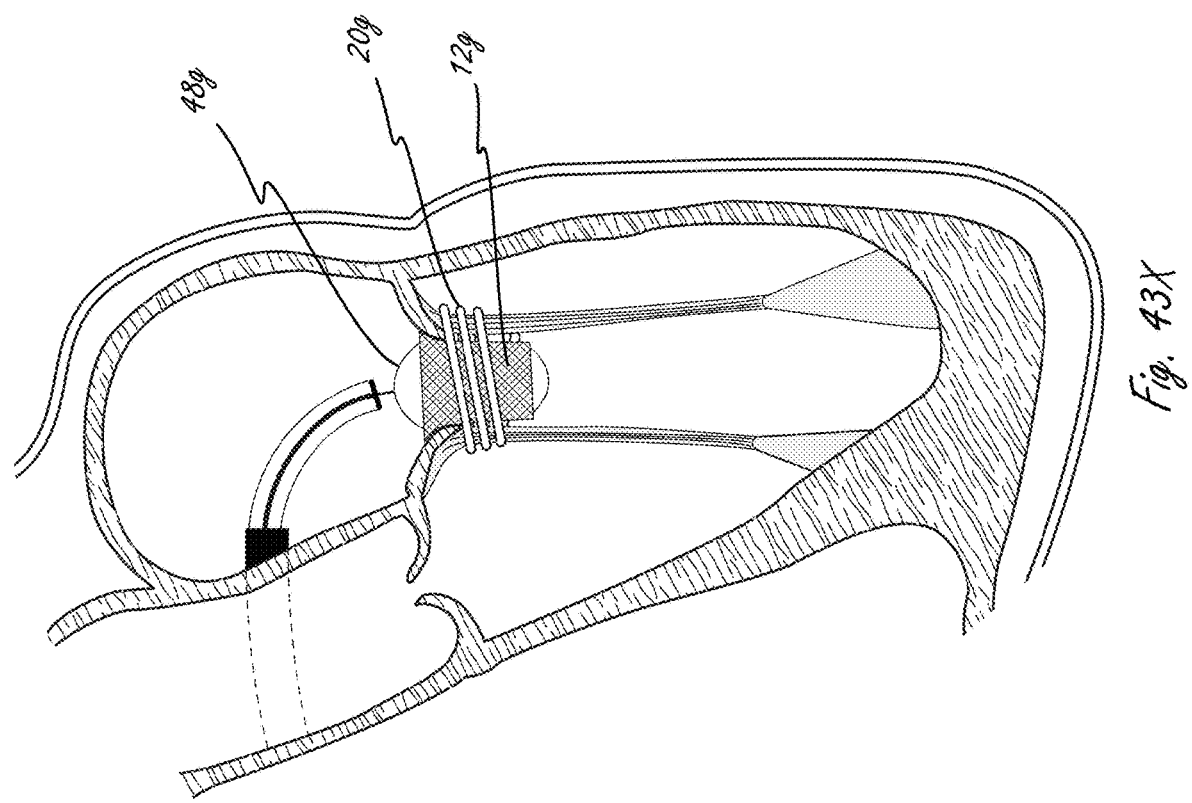
Figure 43W:
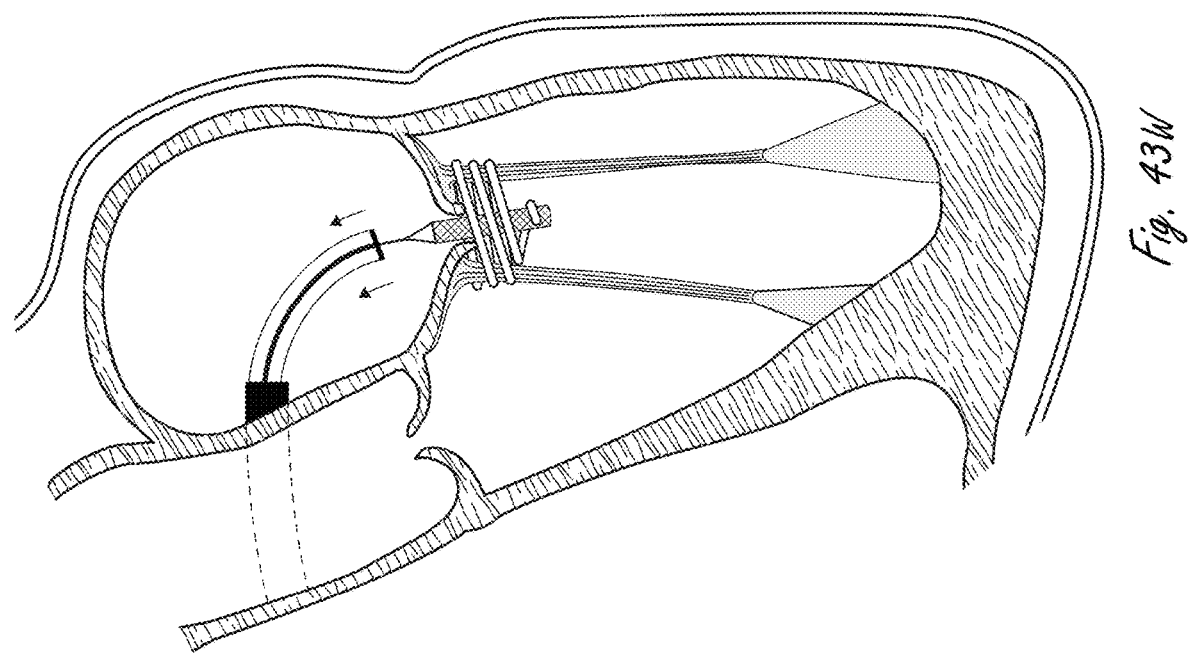
Figure 43Z:
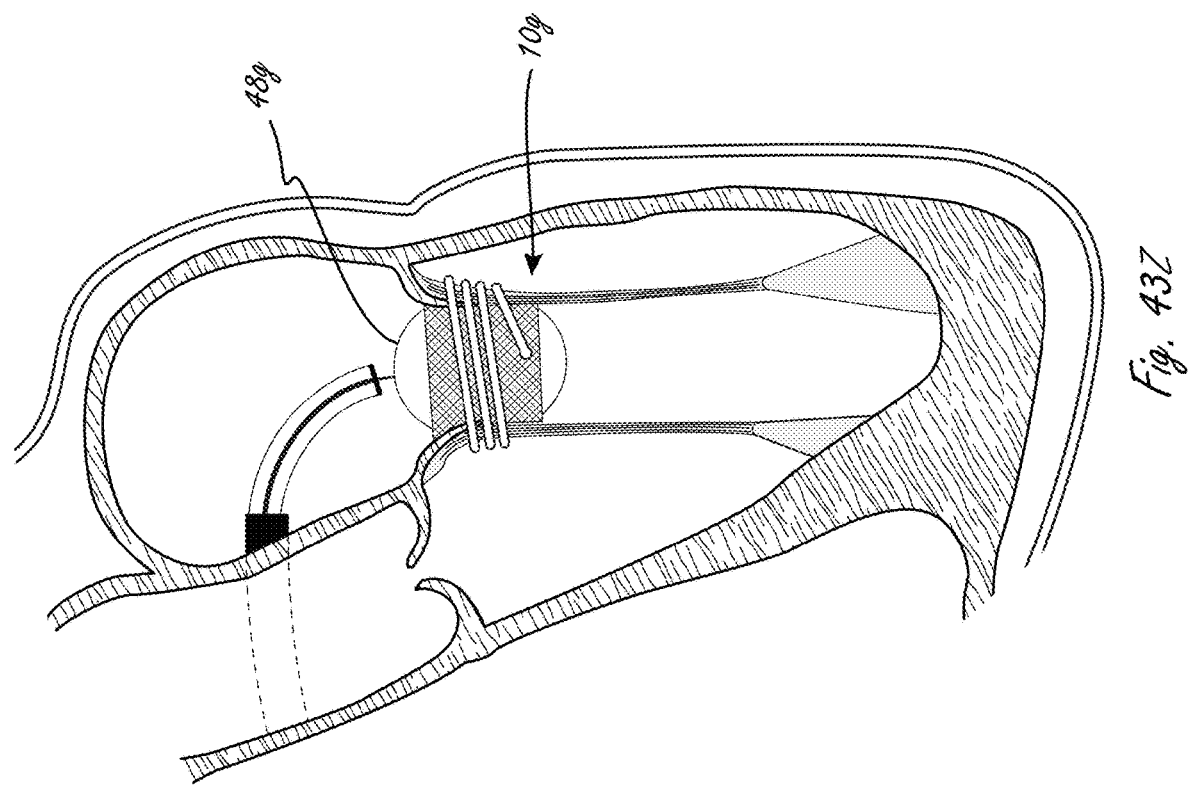
Figure 43Y:
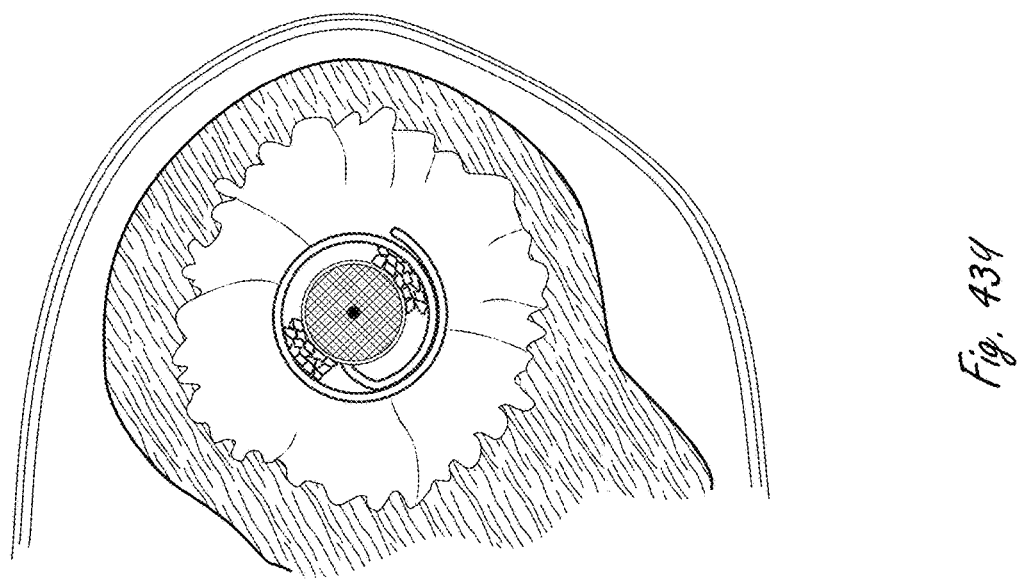
Figure 43A:
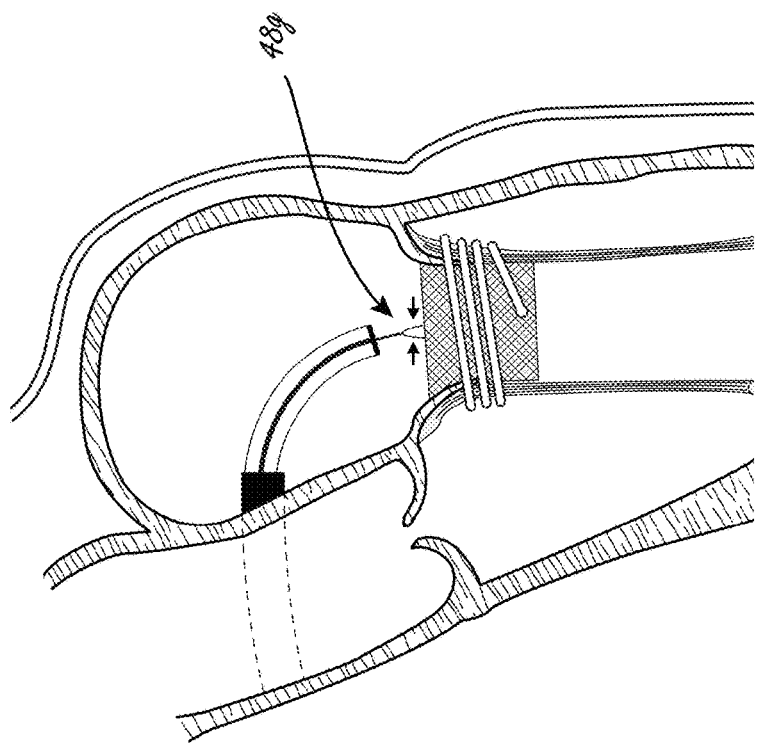
Figure 43A:
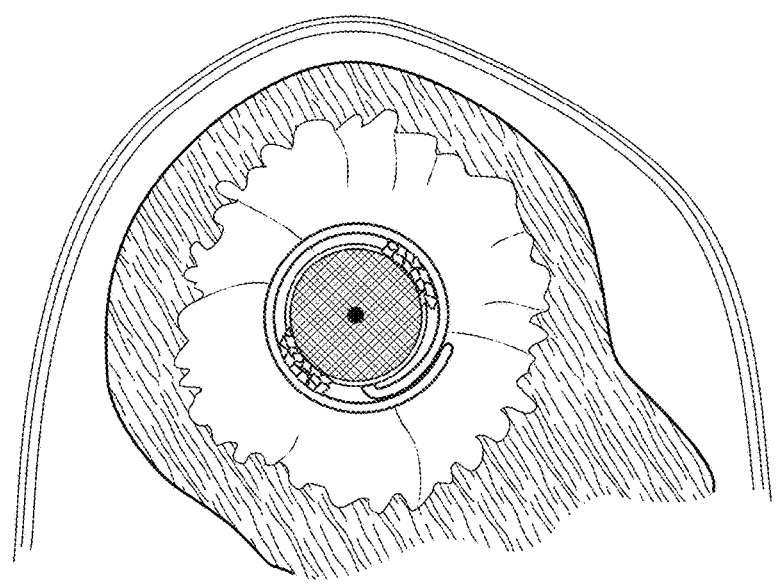
Figure 43A:
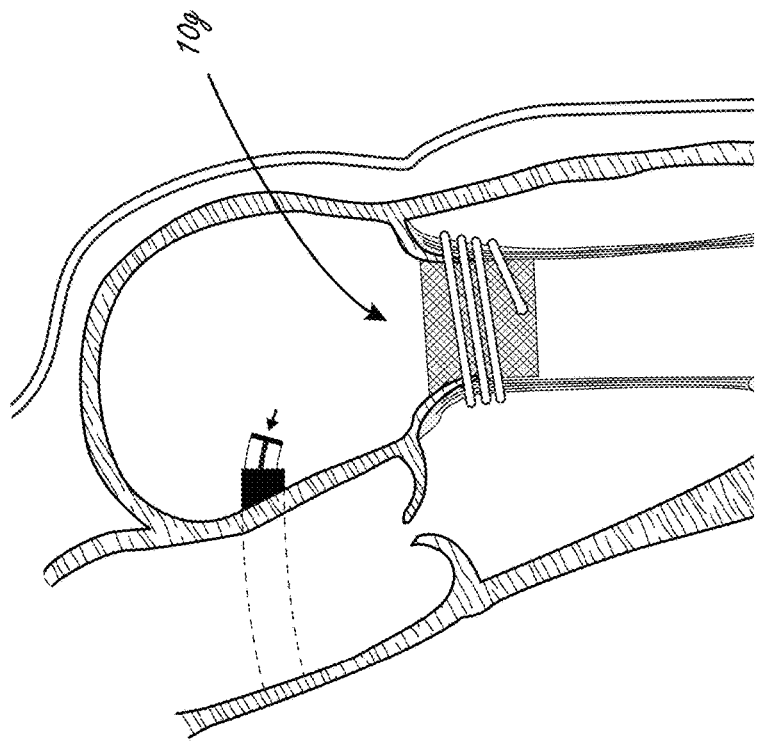
Figure 43A:
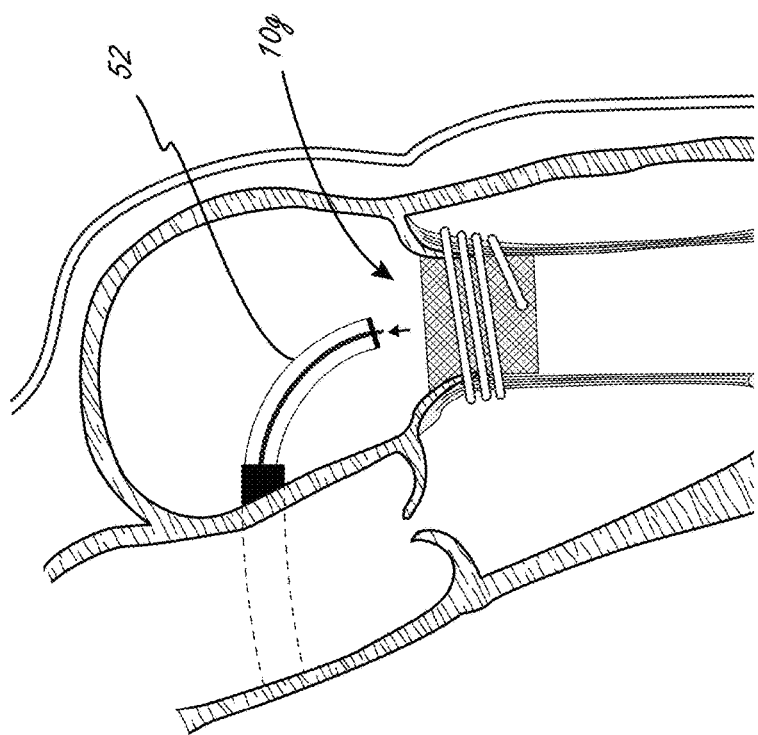
Figure 43A:
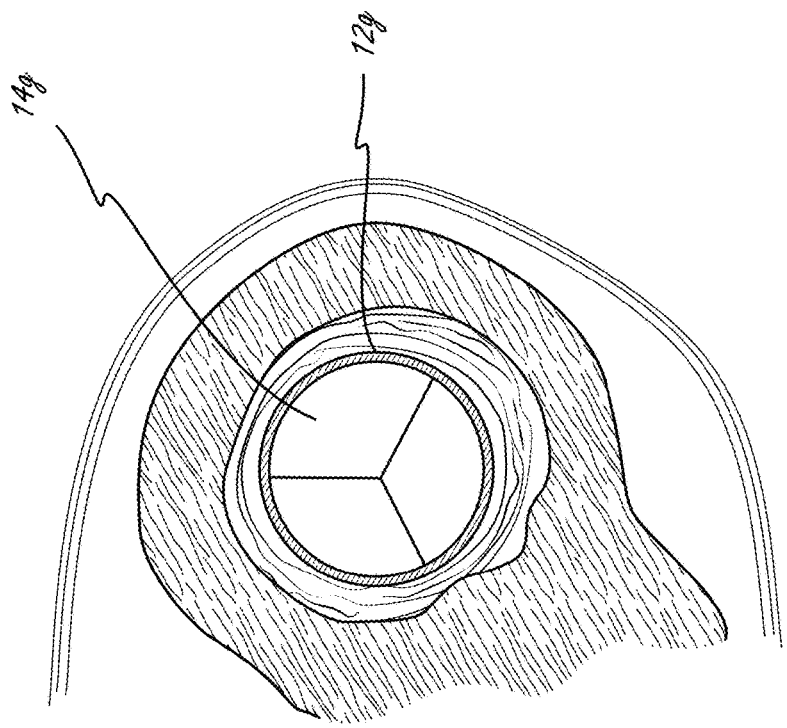
Figure 43A:
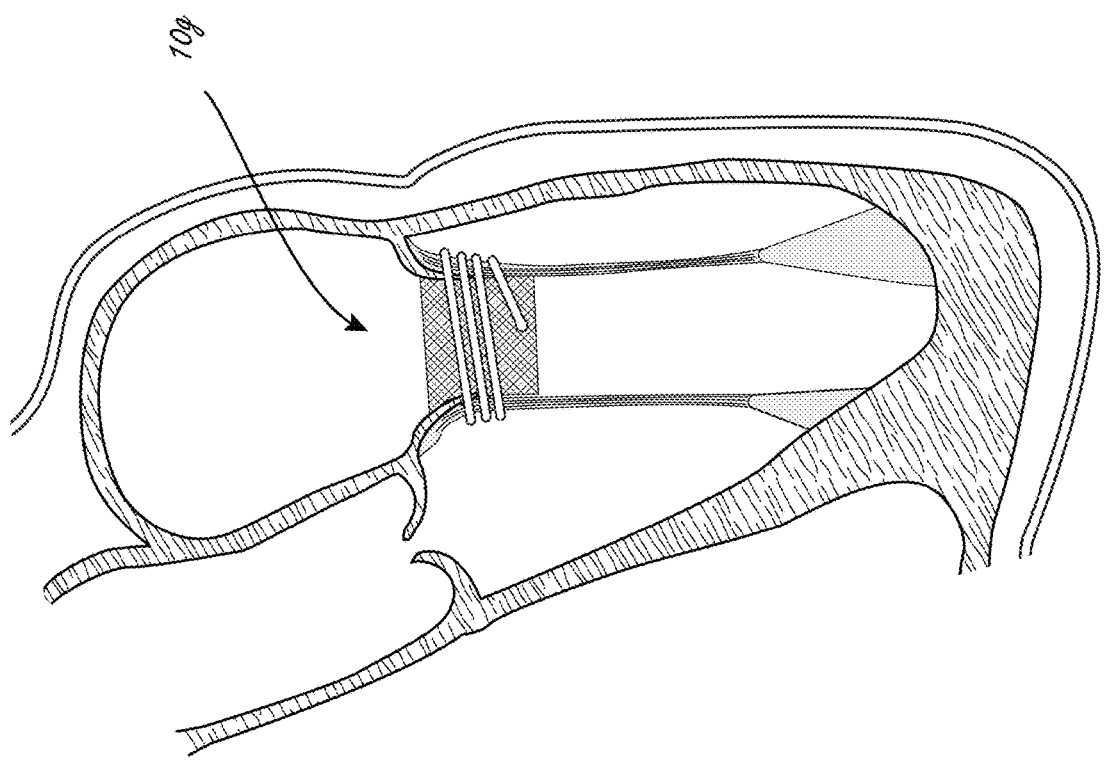
Figure 45:
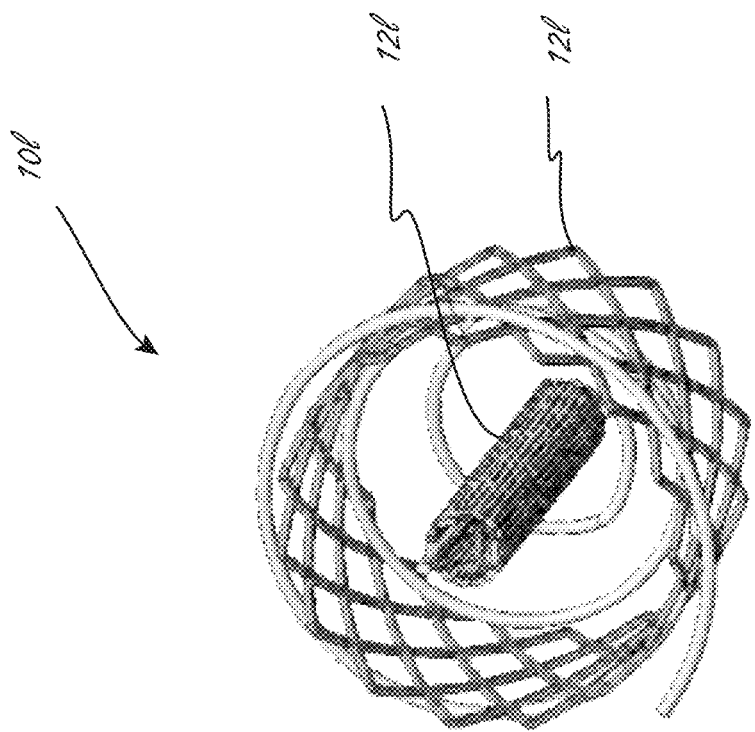
FIGS. 44-49 show a valve device similar to the one of FIG. 6, except that the frame structure is self-expanding, in accordance with embodiments.
Figure 44:
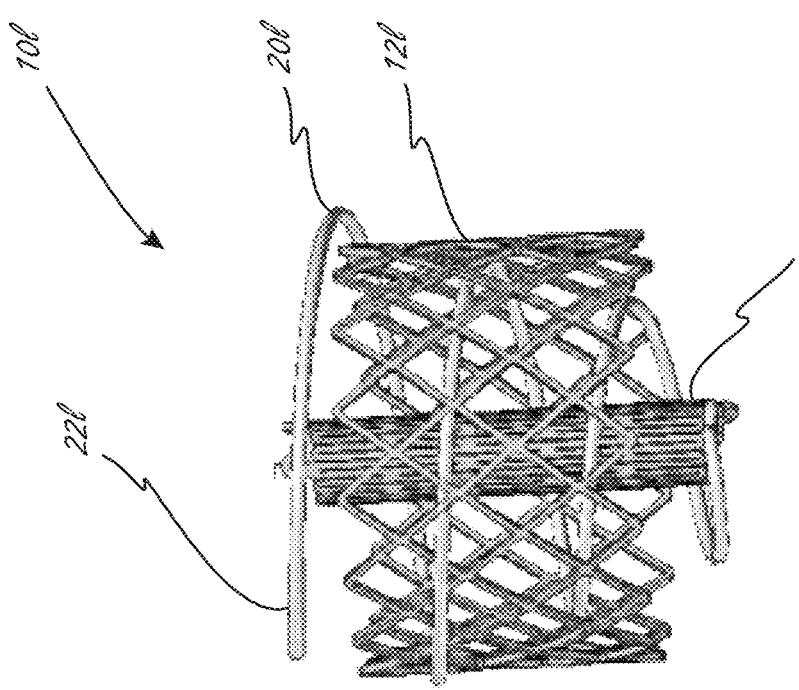
Figure 47:
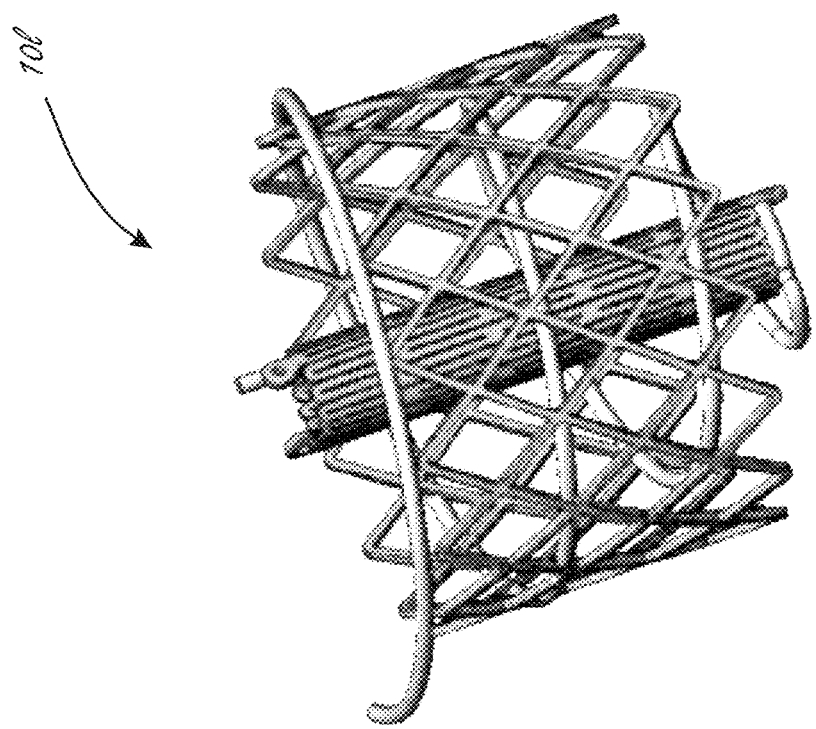
Figure 46:
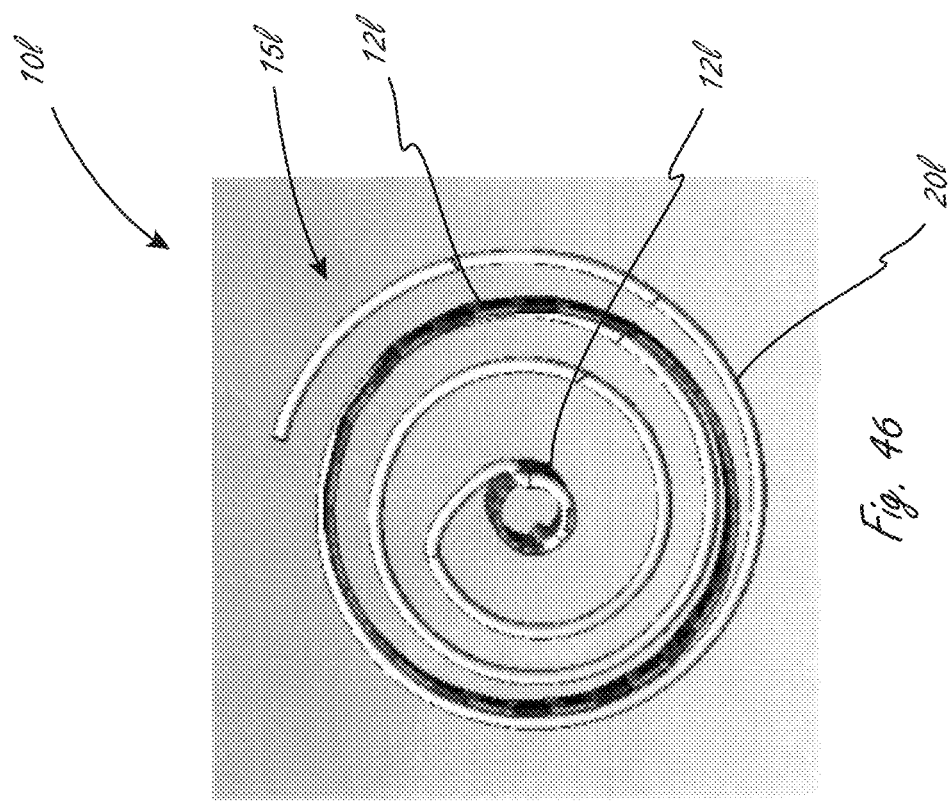

FIGS. 43W-43AA show expansion of the frame structure 12g within the native valve 4. The frame structure 12g may be expanded within the native valve 4 from an unexpanded configuration to an expanded configuration. In some embodiments, at least a portion the frame structure 12g may be expanded within at least a portion of the deployed anchor 15g to anchor the frame structure 12g to the native valve 4. In some embodiments, the frame structure 12g may comprise an expandable stent. In some embodiments, the frame structure 12 of valve prosthesis 10g may be self-expandable. In some embodiments, the frame structure 12 of valve prosthesis 10g may be balloon-expandable. The delivery device 30' may comprise a balloon 48g which may be disposed within the valve prosthesis 10g in order to expand the valve prosthesis 10g. The balloon 48g may be positioned within at least a portion of the valve prosthesis 10g, for example within at least a portion of frame structure 12 in an uninflated configuration, as shown in FIG. 43W, prior to being inflated. The inflatable balloon 48g may, for example, be disposed within the inner shaft 52 or outer sheath 50 while the anchor 15g is being positioned adjacent the native valve 4 and then advanced therefrom (or the inner shaft 52 or outer sheath 50 is retracted therefrom) to be positioned within the frame structure 12g. Alternatively, the inflatable balloon 48g may be disposed within the frame structure 12g during placement of the valve prosthesis 10g. FIGS. 43X-43Y show the frame structure 12g partially expanded by partially-inflated balloon 48g. As shown in FIG. 43Y, the frame structure 12g may be partially expanded towards the anchor 15g in order to capture the chordae tendineae 40 therebetween. As the frame structure 12g continues to be expanded to a fully expanded state, as shown in FIGS. 43Z-43AA, the chordae tendineae 40 may be sandwiched between the anchor 15g and the frame structure 12g. The frame structure 12g and anchor 15g may thus be anchored to the chordae tendineae 40.

The valve prosthesis 10g may then be released from the delivery device 30'. In some embodiments, releasing the valve prosthesis 10g may comprise releasing the anchor 15g and/or the frame structure 12g. Releasing the valve prosthesis 10g from the delivery device 30' may comprise expanding the valve prosthesis 10g from the unexpanded configuration to the expanded configuration. For example, expanding the frame structure 12g and releasing the frame structure 12g may occur simultaneously as described herein. Alternatively, the frame structure 12g may be released prior to or after being expanded.

FIGS. 43AB-43AD show deflation of the balloon 48g (FIG. 43AB), retraction of the balloon 48g into inner shaft 52 (FIG. 43AC), and removal of the delivery device 30' from the heart 2 (FIG. 43AD). After the frame structure 12g has been expanded and anchored to the native valve 4 as described herein, the inflatable balloon 48g may be deflated. The balloon 48g may be retracted back into the delivery device 30', for example into inner shaft 52. The delivery device 30' may then be removed from the heart 2.

FIGS. 43AE-43AF show the valve prosthesis 10g fully expanded with the native valve leaflets 42 and chordae tendineae 40 captured between the frame structure 12g and the anchor 15g. As described herein, the valve prosthesis 10g may comprise one or more valve segments 14g disposed therein to replace the native valve leaflets 42.

Although the steps above show a method of deploying a valve prosthesis 10 within a native valve 4 in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as necessary to assemble at least a part of an article.

For example, in some embodiments deploying the valve prosthesis 10 may occur in multiple steps such that a portion of the valve prosthesis 10 (e.g., anchor 15) may be deployed before another portion the valve prosthesis 10 (e.g., frame structure 12). Alternatively, or in combination, in some embodiments, deploying the anchor 15 may occur in multiple steps such that a portion of the anchor 15 may be deployed before being advanced through the native valve 4 and another portion of the anchor 15 may be deployed after being advanced through the native valve 4. Alternatively, or in combination, the delivery device 30 may be advanced from the left atrium 25 to the left ventricle 26 with the valve prosthesis 10 undeployed. In many embodiments, the frame structure may 12 be self-expanding and the balloon 48 may not be necessary for expansion of the frame structure 12. Alternatively, or in combination, the anchor 15 may be released after the frame structure 12 has been expanded within it.

In some embodiments, any of the valve prostheses described herein may be deployed to replace a diseased mitral valve. The first side of the native valve may comprise a left atrium and the second side of the native valve may comprise a left ventricle.

In some embodiments, any of the valve prostheses described herein may be deployed to replace a diseased tricuspid valve. The first side of the native valve may comprise a right atrium and the second side of the native valve may comprise a right ventricle.

In some embodiments, any of the valve prostheses described herein may be deployed to replace a diseased aortic valve. The first side of the native valve may comprise a left ventricle and the second side of the native valve may comprise an aorta.

It will be understood by one of ordinary skill in the art that, while FIGS. 43A-43AF refer to delivery of valve prosthesis 10g, similar steps may be used for delivery of any of the valve prosthesis described herein.

FIGS. 44-49 show another exemplary valve prosthesis device 10l which is similar to valve prosthesis devices 10 and 10g-10j except that the frame structure 12l is self-expanding. As shown in FIGS. 44-47, the valve prosthesis 10l includes a helical coil 20l similar to helical coils 20 and 20g. Frame structure 12l is similar frame structures 12 and 12g-12j except that it is configured to expand to the deployed shape upon removal of the sheath of the delivery device. The frame structure 12l is shown in the drawings in both the collapsed and deployed shapes for ease of understanding. The exemplary frame structure 12l may be formed of a shape memory material or any material having superelastic properties. The exemplary frame structure 12l is formed with a diamond pattern, but one of ordinary skill in the art will appreciate from the description herein that many other patterns and configurations will be suitable. The exemplary frame structure 12l is configured to expand in a similar manner to a self-expanding stent or scaffold.

Figure 49:
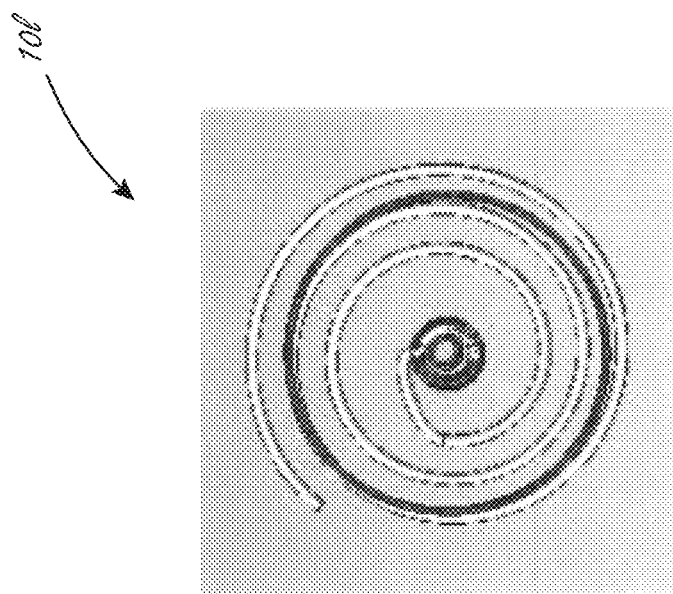
Figure 48:
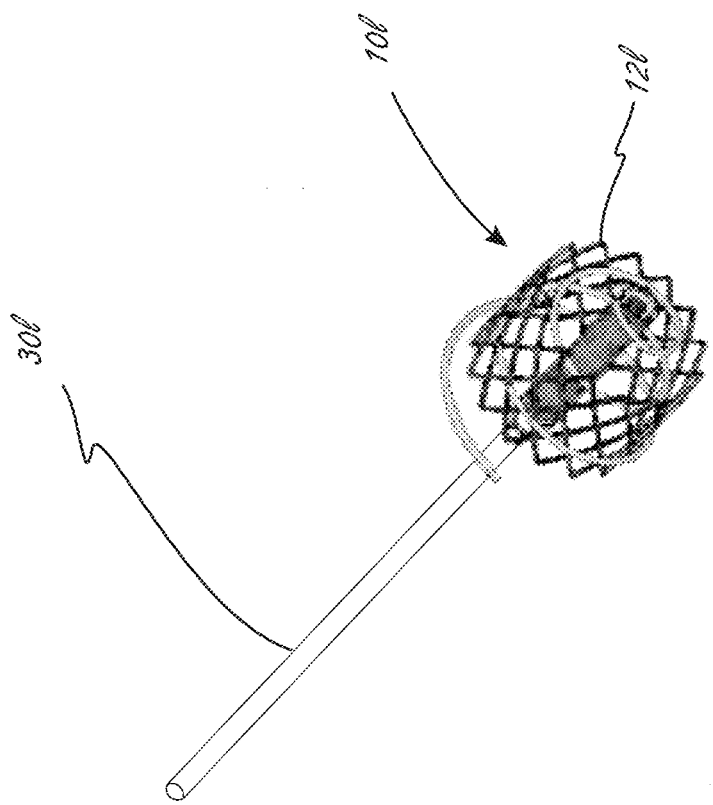

FIGS. 48 and 49 show the exemplary valve prosthesis device 10l loaded on an exemplary delivery tool or catheter 30l. The manner of implanting the valve prosthesis device 10l is similar to the method described herein with respect to valve device 10g except that the frame structure 12l is configured to expand on its own rather than under the force of a balloon. In this case, the frame structure 12l and prosthetic valve segment can be easily deployed in one shot after the coil 15l has been anchored to one or more structures adjacent the native valve. This may reduce the time of the implantation procedure and may eliminate complications like a system for deploying, inflating, and deflating the balloon used in a balloon-expandable embodiment.

The valve prosthesis device and implant method described herein in accordance with the present disclosure may provide many advantages as will be understood by one of ordinary skill in the art. The overall device and method may provide a simpler way to approach the native valve compared to existing devices. The system may enable a transcatheter approach through the septal wall compared to more invasive transapical approaches. The device may provide a consistent and relatively easy mechanism for anchoring to the native valve. Clinicians need only use the common technique of inserting the device through the valve and then rotating the anchor. The coil may provide preliminary anchoring in the native valve. If desired, the clinician can readjust the anchor and/or retrieve the anchor (e.g. by counterrotation). The device is then easily set by expanding within the native valve leaflets. The device and methods in accordance with the present disclosure may also address unmet clinical needs with atrioventricular repair and replacement. Existing devices face challenges with the complex anatomy of the mitral and tricuspid valves, for example. The present disclosures address these complications by reshaping the native valve annulus to a conventional round shape and providing a robust, yet simple, anchoring mechanism.

Figure 50:
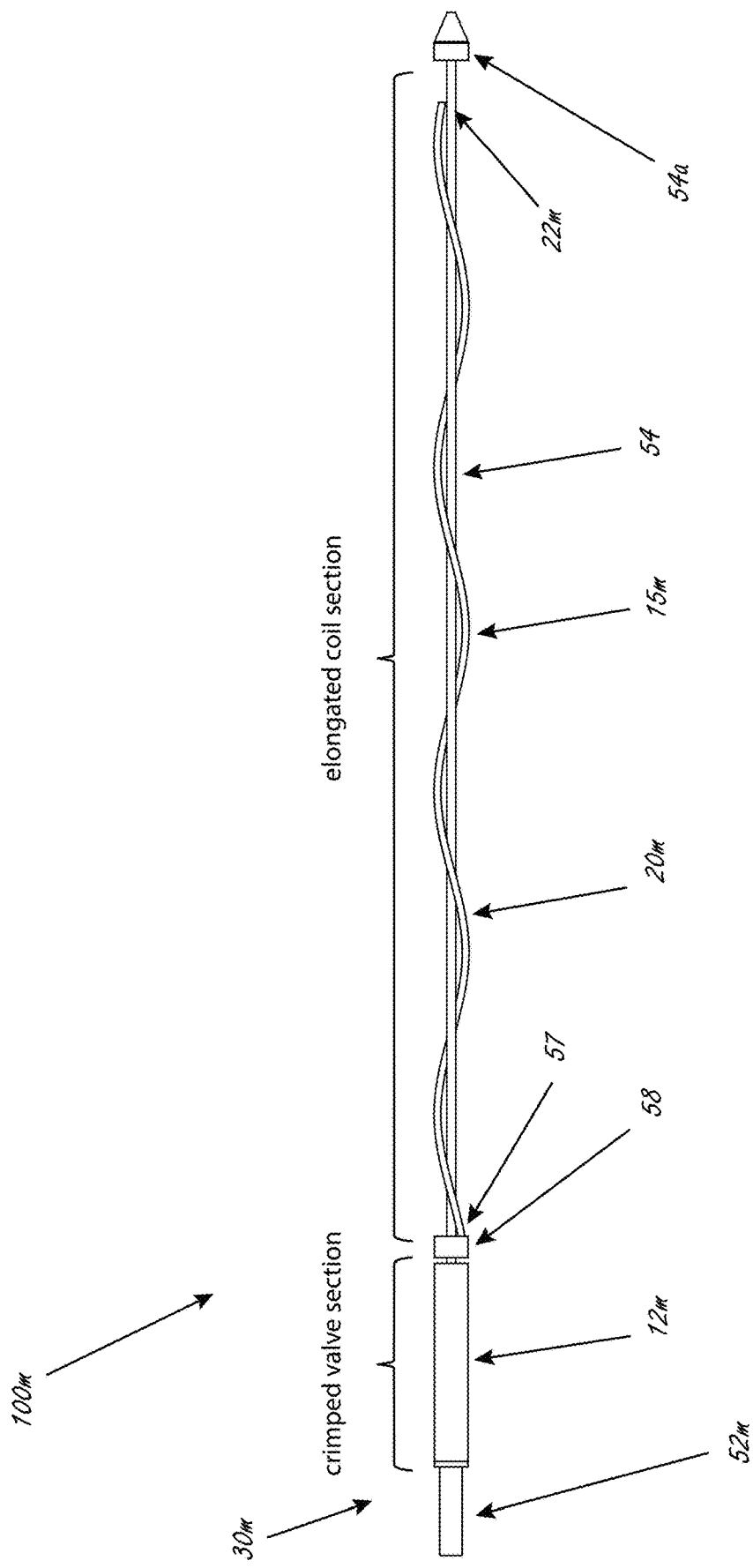
FIG. 50 shows a side view of a valve prosthesis system comprising a frame structure and an anchor loaded on a delivery device with the anchor in a delivery (e.g., elongated) configuration, in accordance with embodiments.
Figure 51:
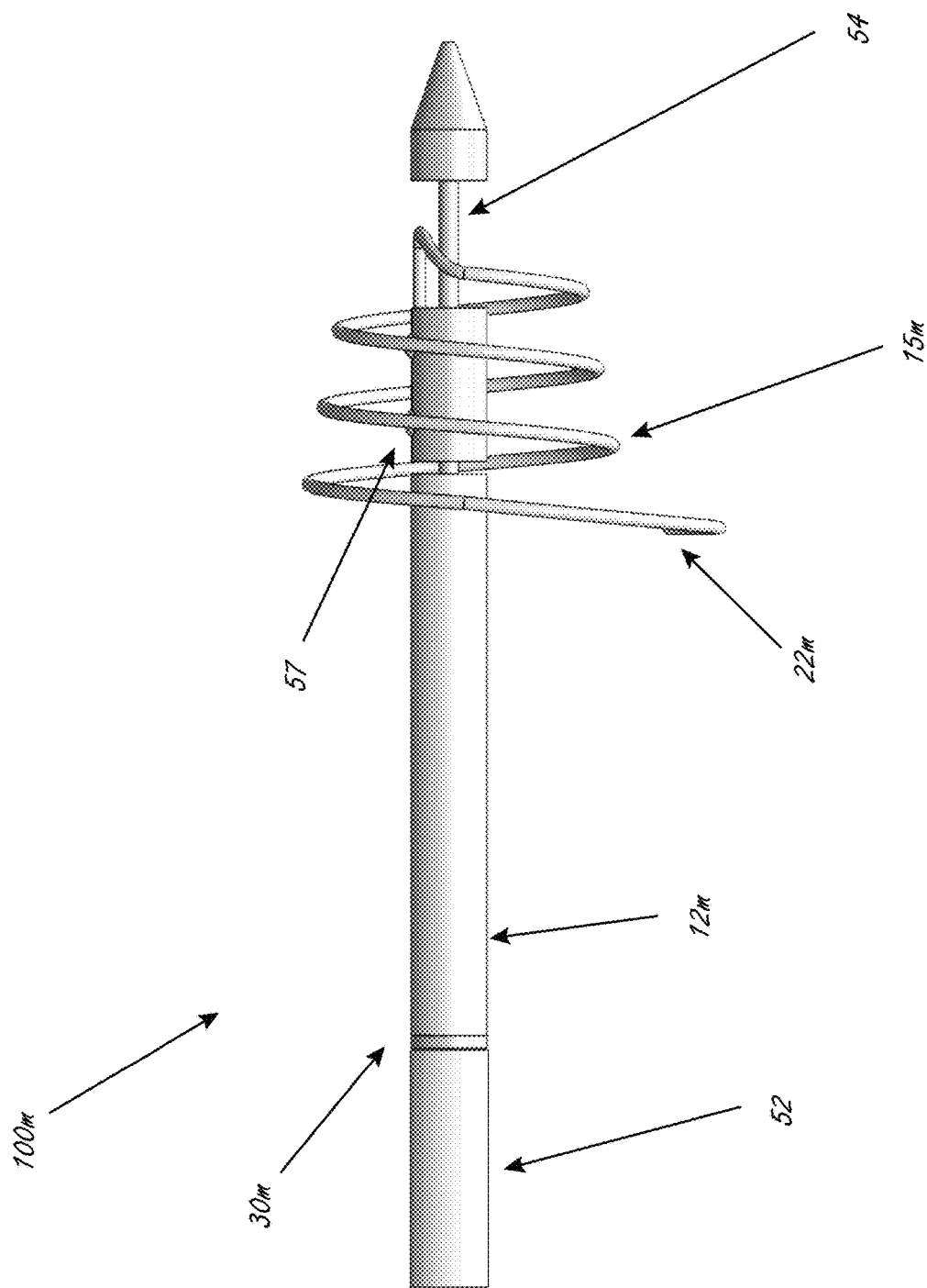
FIG. 51 shows a side view of the valve prosthesis system of FIG. 50 with the anchor in a deployed configuration, in accordance with embodiments.

FIG. 50 shows a side view of a valve prosthesis system 100m comprising a frame structure 12m and an anchor 15m loaded on a distal end of a delivery device 30m with the anchor 15m in an elongated delivery configuration. FIG. 51 shows a side view of the valve prosthesis system 100m of FIG. 50 with the anchor 15m in a deployed configuration. The valve prosthesis may be substantially similar to any of the valve prostheses described herein except that the anchor may be detachably coupled to the delivery device during delivery as described herein instead of the frame structure. By coupling the anchor to the delivery device instead of the frame structure, the frame structure may be expanded inside the anchor without altering the shape or position of the deployed anchor during expansion, which may lead to a better connection between the anchor and the frame structure adjacent the native valve than may have been possible if expansion of the frame structure caused deflection or movement of the deployed anchor.

The frame structure 12m may have an unexpanded (for example, a compressed configuration) and an expanded configuration (not shown). The frame structure 12m is shown in the unexpanded configuration. The anchor 15m may comprise a wire 20m having a free end 22m. The anchor 15m may be configured to be fully advanced from a first side of a native valve in a patient (e.g. an atrial side) to a second side of the native valve (e.g., into a ventricle of the heart) and anchor the frame structure 12m to the native valve when the frame structure 12m is in the expanded configuration adjacent the native valve. The delivery device 30m may comprise an outer sheath (e.g. an outer catheter, not shown), an inner shaft 52 (e.g., a delivery tube) disposed within a lumen of the outer sheath, and a guidewire 54 disposed within a lumen of the inner shaft 52. A proximal end 57 of the anchor 15m may be detachably coupled to the inner shaft 52 during delivery to the native valve. The outer sheath may be steerable.

The anchor 15m may comprise an elongated delivery configuration (shown in FIG. 50) and a deployed configuration (shown in FIG. 51). The anchor 15m may be configured to be actuated from the delivery configuration to the deployed configuration adjacent the native valve. In various embodiments, the anchor 15*m* may be self-expanding and may move to the deployed configuration as it is removed from the delivery sheath. In various embodiments, the anchor may be configured to self-assemble when it is deployed in the heart cavity (e.g. in a left atrium). Retraction of the guidewire 54 into the lumen of the inner shaft 52 may actuate the anchor 15*m* into the deployed configuration. Alternatively, or in combination, the anchor 15*m* may be maintained in the elongated configuration by radial constriction from the outer sheath. Advancement of the inner shaft 52 out of the lumen of the outer sheath may actuate the anchor 15*m* into the deployed configuration.

A proximal end 57 of the anchor 15*m* may be detachably coupled to the inner shaft 52 of the delivery device 30*m*. The proximal end 57 may be configured to remain engaged with the inner shaft 52 after being actuated from the elongated configuration to the deployed configuration adjacent the native valve. The frame structure 12*m* may be configured to remain in its unexpanded configuration while the anchor 15*m* is in the deployed configuration.

The proximal end 57 of the anchor 15*m* may be detachably coupled to the inner shaft 52 of the delivery device 30*m* by radial constriction from the outer sheath. Retraction of the outer sheath away from the proximal end 57 of the anchor 15*m* may detach the anchor 15*m* from the delivery device 30. Alternatively, or in combination, the proximal end 57 of the anchor may be detachably coupled to the inner shaft 52 of the delivery device 30*m* by an attachment element 58. Alternatively, or in combination, the proximal end 57 of the anchor 15*m* may be detachably coupled to the inner shaft 52 of the delivery device 30*m* by a weak adhesive.

The anchor 15*m* may be configured to rotate when the inner shaft 52 is rotated. Rotation of the anchor may aid in advancement of the anchor to the second side of the native valve. Alternatively, or in combination, rotation of the anchor, for example a wire 20*m* comprising a free end 22*m*, may aid in capture of one or more structures on the second side of the native valve by the free end 22*m* as described herein. By capturing one or more structures on the second side of the native valve, the anchor 15*m* may maintain its position relative to the native valve and provide an anchor point for the frame structure 12*m* when in the expanded configuration.

The frame structure 12*m* may comprise an unexpanded configuration and an expanded configuration as described herein. The expanded configuration may have a generally tubular expanded shape. The frame structure 12*m* may be configured for expanding within the native valve of the patient. In some embodiments, the unexpanded configuration may be sized and dimensioned for percutaneous insertion and the expanded configuration may be sized and dimensioned for implantation in the native valve of the patient.

Similar to the other frame structures described herein, the frame structure 12*m* may comprise a first and second opposite ends, the first end extending above a native valve and the second end extending below the native valve when the frame structure 12*m* is anchored to the native valve. Alternatively, the frame structure 12*m* may be configured to sit entirely below the native valve when the frame structure 12*m* is anchored to the native valve.

In some embodiments, similar to other frame structures described herein, the frame structure may comprise an expanded outer periphery in the expanded configuration and a compressed outer periphery when subject to an external radial force in the unexpanded configuration. The compressed outer periphery may be smaller in diameter than the expanded outer periphery.

The frame structure 12*m* may be balloon-expandable, self-expanding, or otherwise expansible as will be understood by one of ordinary skill in the art from the description herein.

For example, the delivery system 30*m* may comprise an inflatable balloon (not shown) disposed within the frame structure 12*m*. Inflation of the balloon may cause expansion of the frame structure 12*m* as described herein.

Alternatively, or in combination, the frame structure 12*m* may be maintained in the unexpanded configuration by radial constriction from the outer sheath of the delivery device 30*m*. Advancement of the inner shaft out of the lumen of the outer sheath may actuate the frame structure into the expanded configuration.

The frame structure 12*m* may be detachably coupled to the delivery device 30*m* in the unexpanded configuration during delivery to the native valve. Expansion of the frame structure 12*m* to the expanded configuration may detach the frame structure from the delivery device.

Similar to other frame structure and anchor embodiments described herein, at least a portion the frame structure 12*m* may be expanded within at least a portion of the deployed anchor 15*m* to anchor the frame structure 12*m* to the native valve. For example, the anchor 15*m* may be deployed such that it captures one or more structures therein, for example one or more chordae tendineae and/or one or more valve leaflets. Expansion of the frame structure 12*m*, or a portion thereof, within the anchor 15*m* may compress the capture structures between the frame structure 12*m* and the anchor 15*m* to anchor the frame structure 12*m* in place.

The guidewire 54 may comprise a nosecone 54*a* configured to facilitate guidance of the guidewire to the native valve.

Similar to other wires described herein, the wire 20*m* may comprise a helical wire in the deployed configuration. The free end 22*m* of the helical wire 20*m* may extend radially outward from the frame structure 12*m*, and in particular from the remainder of the wire 20*m*. In some embodiments, the helical wire 20*m* may have a generally tubular shape. The free end 22*m* of the helical wire 20*m* may extend radially outward from the tubular shape. In some embodiments, the helical wire 20*m* may have a generally frustoconical shape. The free end 22*m* of the helical wire 20*m* may extend radially outward from the frustoconical shape. In some embodiments, the helical wire 20*m* may have a generally cylindrical shape. The free end 22*m* of the helical wire 20*m* may extend radially outward from the cylindrical shape. The free end 22*m* may be configured to encircle a larger radius than the main coils of the helical wire 20*m*. The larger diameter may facilitate capturing of one or more structures, for example the valve leaflets of the chordal tendineae within the sweep of the free end 22*m* when rotated as described herein.

Optionally, the anchor 15*m*, or any of the anchors described herein, may comprise a first portion comprising the helical wire 20*m* and another portion. Alternatively, or in combination, the anchor 15*m* may comprise a plurality of helical wires 20*m*. For example, the anchor 15*m* may comprise at least two helical wires 20*m* having the same or different diameters. Alternatively, or in combination, the anchor 15*m* may comprise at least two helical wires 20*m* having the same or different winding pitches.

As with other anchors described herein, the free end 22*m* of the wire 20*m* may be sized and dimensioned for insertion through the native valve, for example through tissue at or near a commissure of the native valve or through the valve opening itself. In some embodiments, the free end 22m of the wire 20m may comprise an atraumatic tip to avoid reduce risk of injury to the native valve tissue and leaflets. For example, the free end may comprise a blunt end, a ball tip, a curved tip (e.g. J-tip or pigtail), or other atraumatic shapes. Alternatively, the free end 22m of the wire 20m may be configured for piercing tissue. In various embodiments, the free end 22m is separate from and extends outward from the main coils of the anchor 15m. In various embodiments, the main body coils of the anchor 15m circumscribe an area (in the case of a spiral coil) or a volume (in the case of a helical coil) having a diameter, and the free end 22m extends to a radius greater than the diameter of the anchor 15m. In various embodiments, the free end 22m extends to a radius substantially greater than the diameter of the anchor 15m. In various embodiments, the free end 22m is configured to circumscribe a larger diameter than the anchor 15m. In various embodiments, the free end 22m is configured to circumscribe all of the chordae tendineae of the native valve to be treated.

Wire 20m, or any of the wires described herein, may be formed of a material having sufficient rigidity to hold a predetermined shape. The wire may, for example, be formed of a shape memory material (e.g. NiTi). It may be desirable for at least an end portion (e.g. free end 22m) to be relatively rigid such that it can exert a force to move chordal tendineae, while still retaining flexibility to be collapsed within a delivery device. In various embodiments, the end portion only needs sufficient rigidity to hold its shape and will deform under a load. For example, the end portion may be configured with a similar rigidity to a guidewire, or slightly stiffer.

The frame structure 12m, or any of the frame structures described herein, may be configured like a stent. The frame structure 12m may, for example, comprise a scaffold in a diamond pattern formed from a shape memory material (e.g. NiTi). One of ordinary skill in the art will appreciate that many other structures, materials, and configurations may be employed for the frame structure 12m, or any of the other frame structures described herein. For example, the frame structure 12m may be formed of a polymer of sufficient elasticity. The frame structure 12m may be formed of a combination of metal and polymer, such as metal (e.g. shape memory material) covered in polymer. The frame structure 12m may include a variety of patterns besides diamond shapes.

The frame structure 12m, or any of the frame structures described herein, may comprise a valve segment (not shown) disposed therein. As described above, valve segment is used somewhat interchangeably with prosthetic valve leaflet and generally refers to the prosthetic leaflets and frame. As used herein, "prosthetic valve" may refer to all manner of prosthetic and artificial replacement valves including tissue (biological valves), tissue-engineered valves, polymer valves (e.g. biodegradable polymer valves), and even certain mechanical valves. The valve segment can be similar to existing transcatheter valves. The valve segment can be similar to existing surgical tissue valves, and mechanical valves. At least a portion of the valve segment may be positioned within at least a portion of the frame structure. The valve segment may include leaflets formed of multi-layered materials for preferential function. The valve segment may comprise at least one leaflet having an inner layer and an outer layer. The valve segment may be attached to a valve structure which is in turn connected to the frame structure 12m. The valve structure may be connected to the frame structure 12m before or after the frame structure 12m has been deployed adjacent a native valve. The valve segment may be attached directly to the frame structure 12m. The frame structure 12m may be attached to a leaflet, for example an outer layer of a leaflet, at one or more ends of the frame structure 12m. The frame structure 12m may be attached to a leaflet, for example an outer layer of a leaflet, at one or more intermediate portions of the frame structure 12m. The valve segment may comprise a plurality of leaflets. The valve segment may comprise a biocompatible one-way valve. Flow in one direction may cause the leaflet(s) to deflect open and flow in the opposite direction may cause the leaflet(s) to close.

One of ordinary skill in the art will recognize based on the description herein that any of the valve prostheses described herein may comprise any of the frame structure shapes, frame structure designs, frame structure materials, anchor shapes, anchor windings, anchor materials, free end tips, leaflet(s) configurations, or any other of the variable features described herein in any combination thereof as desired.

Method of Use

The distal end of the delivery device 30m may be configured to be advanced from a first side of a native valve to a second side of the native valve. For example, the distal end of the delivery device 30m may be advanced from a left atrial side of a mitral valve to a left ventricular side of a mitral valve. In some instances, the distal end of the delivery device 30m may be transseptally inserted into the left atrium of the heart prior to advancement into the left ventricle. Alternatively, or in combination, the distal end of the delivery device 30m may be steerable such that it is positionable to point towards the first side of the native valve before being advanced to the second side of the native valve.

After advancing to the second side of the native valve, the anchor 15m may be fully deployed on the second side of the native valve. Fully deploying the anchor 15m may comprise actuating the anchor 15m from an elongated configuration to a deployed configuration as shown in FIG. 51.

In some embodiments, fully deploying the anchor 15m may comprise actuating the anchor 15m from an elongated configuration to a deployed configuration on the first side of the native valve (e.g., in the left atrium) and advancing the anchor 15m, in the deployed configuration, through the native valve to the second side of the native valve (e.g., into the left ventricle). Advancing the anchor 15m may comprise pushing the anchor 15m through the native valve as described herein. Advancing the anchor 15m may further comprise rotating the anchor 15m through the native valve.

In some embodiments, fully deploying the anchor 15m may comprise positioning the anchor 15m such that it is located only on the second side of the native valve.

In some embodiments, the anchor 15m may be actuated from the delivery configuration to the deployed configuration on a first side of the native valve prior to being advanced to a second side of the native valve. For example, the anchor 15m may be fully deployed in a left atrium of a heart prior to being advanced to a left ventricle of the heart as described herein.

Alternatively, the anchor 15m may be actuated from the delivery configuration to the deployed configuration on a second side of the native valve after being advanced to the second side from a first side of the native valve. For example, anchor 15m may be advanced from a left atrium of a heart prior to being deployed in a left ventricle of the heart.

The free end 22m of the deployed anchor 15m may optionally be rotated around one or more structures on the second side of the native valve. The one or more structures may comprise one or more valve leaflets of the native valve. Alternatively, or in combination, the one or more structures may comprise one or more chordae of the left ventricle.

The free end 22m of the deployed anchor 15m may optionally rotated around one or more structures on the second side of the native valve such that the one or more structures (e.g., chordae, leaflets, or annulus) are pulled radially inwards towards the longitudinal axis of the anchor 15m and/or towards the longitudinal axis of the delivery device 30m. The anchor 15m and/or free end 22m may be configured such that minimal torque is applied to the one or more structures. Alternatively, or in combination, the anchor 15m and/or free end 22m may be configured such that the one or more structures are not rotated, or are minimally rotated, during rotation of the anchor 15m.

In some embodiments, the valve prosthesis 10m, for example anchor 15m, may be counter-rotated in order to reposition the anchor 15m with respect to the one or more structures of the native valve before continuing the rotation in the first direction. For example, counter-rotation may be applied if the one or more structures are caught by the free end of the anchor 15m (or another part of the valve prosthesis 10m or delivery device 30m) during the initial rotation. In such instances, counter-rotation may enable to the clinician to disengage some or all of the one or more structures to reduce the stress or torque on the one or more structures (e.g., by adjusting the position of the valve prosthesis 10m) before resuming rotation. Rotation and counter-rotation may be applied as many times as desired by the clinician in order to properly position the anchor 15g around the one or more structures of the native valve.

The anchor 15m may then be released from the distal end of the delivery device 30m. The anchor 15m may be released from the distal end of the delivery device 30m on the second side of the native valve.

The frame structure 12m may be expanded within the native valve from an unexpanded configuration to an expanded configuration.

The frame structure 12m may be released from the distal end of the delivery device 30m. In some embodiments, at least a portion the frame structure 12m may be expanded within at least a portion of the deployed anchor to anchor 15m the frame structure 12m to the native valve.

In some embodiments, expanding the frame structure and releasing the frame structure may occur simultaneously.

Finally, the delivery device 30m may be retracted from the native valve.

Additional information about the frame structure may be found in U.S. Provisional Applications Nos. 62/720,853, 62/742,043, 62/748,162, 62/755,996, 62/784,280, 62/813,963, 62/815,791, 62/820,570, 62/828,835, 62/833,425, 62/833,430, 62/851,245, 62/872,016, 62/873,454, 62/879,979, 62/894,565, 62/925,505, 62/927,922, 62/933,122, 62/951,260, U.S. patent application Ser. Nos. 16/546,901, 16/594,946, and International Patent Applications No. PCT/US2019/047542, PCT/US2019/055049, and PCT/US2019/057082, incorporated herein by reference in their entireties for all purposes.

Additional information about the anchor may be found in U.S. Provisional Applications Nos. 62/720,853, 62/742,043, 62/748,162, 62/755,996, 62/784,280, 62/813,963, 62/815,791, 62/820,570, 62/828,835, 62/833,425, 62/833,430, 62/851,245, 62/872,016, 62/873,454, 62/879,979, 62/894,565, 62/925,505, 62/927,922, 62/933,122, 62/951,260, U.S. patent application Ser. Nos. 16/546,901, 16/594,946, and International Patent Applications No. PCT/US2019/047542, PCT/US2019/055049, and PCT/US2019/057082, incorporated herein by reference in their entireties for all purposes.

Additional information about the delivery device may be found in U.S. Provisional Applications Nos. 62/720,853, 62/742,043, 62/748,162, 62/755,996, 62/784,280, 62/813,963, 62/815,791, 62/820,570, 62/828,835, 62/833,425, 62/833,430, 62/851,245, 62/872,016, 62/873,454, 62/879,979, 62/894,565, 62/925,505, 62/927,922, 62/933,122, 62/951,260, U.S. patent application Ser. Nos. 16/546,901, 16/594,946, and International Patent Applications No. PCT/US2019/047542, PCT/US2019/055049, and PCT/US2019/057082, incorporated herein by reference in their entireties for all purposes.

The valve prosthesis may be substantially similar to any of the valve prostheses described in U.S. Provisional Applications Nos. 62/720,853, 62/742,043, 62/748,162, 62/755,996, 62/784,280, 62/813,963, 62/815,791, 62/820,570, 62/828,835, 62/833,425, 62/833,430, 62/851,245, 62/872,016, 62/873,454, 62/879,979, 62/894,565, 62/925,505, 62/927,922, 62/933,122, 62/951,260, U.S. patent application Ser. Nos. 16/546,901, 16/594,946, and International Patent Applications No. PCT/US2019/047542, PCT/US2019/055049, and PCT/US2019/057082, incorporated herein by reference in their entireties for all purposes.

Figure 52:
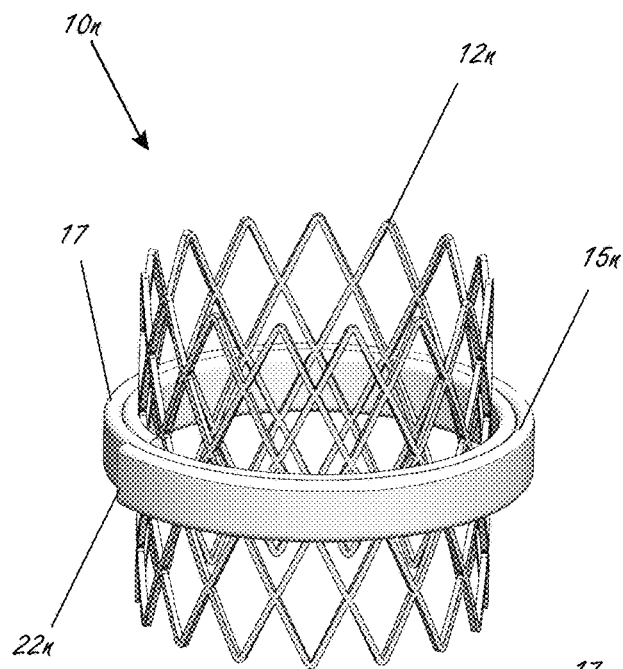
FIGS. 52-54 show several views of a valve prosthesis with an anchor comprising a spiral band, in accordance with embodiments.
Figure 53:
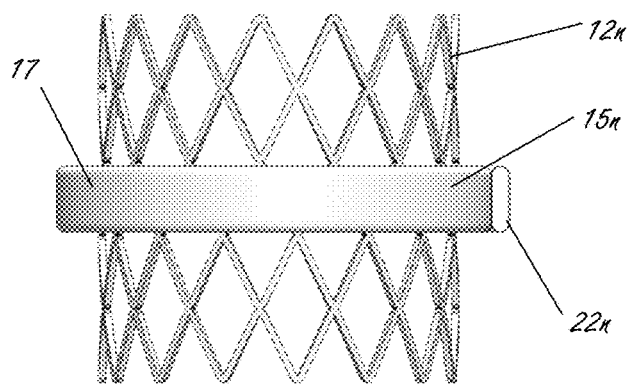
Figure 54:
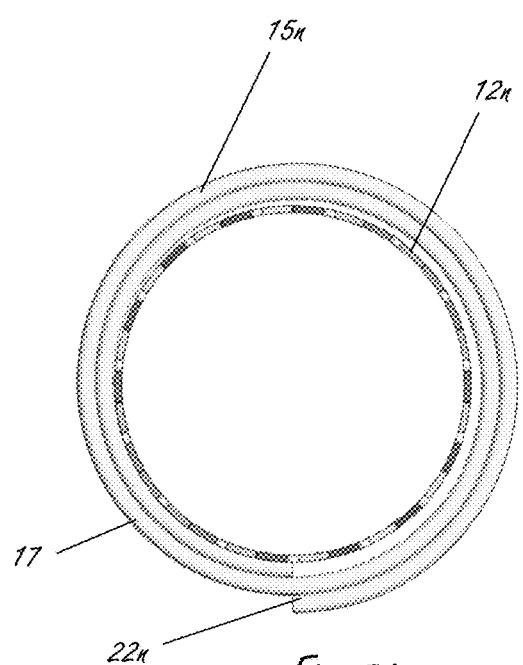

FIGS. 52-54 show several views of a valve prosthesis 10n with an anchor comprising a flat spiral shaped anchor. The valve prosthesis 10n may be substantially similar to any of the valve prostheses described herein except that the anchor may be configured to have a flat spiral shape. For example, the anchor may comprise a spiral band. The frame structure 12n may have an unexpanded configuration (for example, a compressed configuration as described herein) and an expanded configuration as described herein. The frame structure 12n may be substantially similar to any of the frame structures described herein or understood by one of ordinary skill in the art from the description herein. The anchor 15n may comprise a spiral band 17. The anchor 15n may be configured to anchor the frame structure 12n to the native valve when the frame structure 12n is in the expanded configuration adjacent the native valve. The frame structure 12n may be configured to be actuated from the unexpanded configuration to the expanded configuration adjacent a native valve in a patient. The anchor 15n may be configured to be fully advanced from a first side of a native valve in a patient (e.g. an atrial side) to a second side of the native valve (e.g. into a ventricle of the heart) and anchor the frame structure 12n to the native valve when the frame structure 12n is in the expanded configuration adjacent the native valve as described herein.

The flat spiral anchor 15n may comprise a free end 22n. The other end of the anchor 15n may be coupled to the top (proximal end) or bottom (distal end) of the frame structure 12n as described herein. Alternatively, or in combination, the other end of the anchor 15n may not be attached to the frame structure 12n as described herein. The free end 22n of the anchor 15n may facilitate capturing of the valve leaflets and/or chordae tendineae within the sweep of the free end during rotation as described herein. During rotation of the anchor 15n, the leaflets and/or chordae tendineae may be captured by the free end 22n and trapped between the valve frame structure 12n and an interior surface of the anchor 15n.

The free end 22n of the flat spiral anchor 15n may be sized and dimensioned for insertion through the native valve, for example through tissue at or near a commissure of the native valve or through the valve opening itself. In some embodiments, the free end 22n may comprise an atraumatic tip to avoid reduce risk of injury to the native valve tissue and leaflets. For example, the free end 22*n* may comprise a blunt end, a ball tip, a curved tip (e.g. J-tip or pigtail), or other atraumatic shapes. Alternatively, the free end 22*n* may be configured for piercing tissue.

Figure 59:
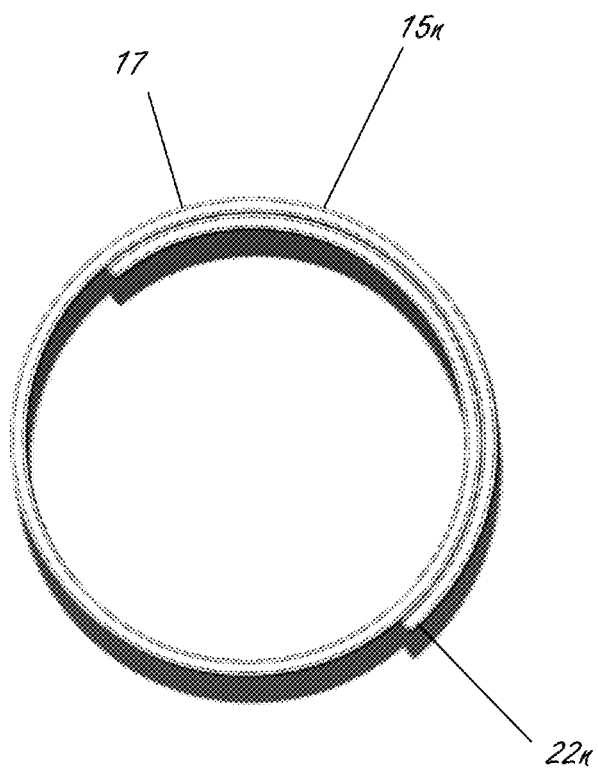

The free end 22*n* of the flat spiral anchor 15*n* may optionally rotated around one or more structures on the second side of the native valve such that the one or more structures (e.g., chordae, leaflets, or annulus) are pulled radially inwards towards the longitudinal axis of the anchor 15*n* and/or towards the longitudinal axis of the delivery device 30*n*. The anchor 15*n* and/or free end 22*n* may be configured such that minimal torque is applied to the one or more structures. Alternatively, or in combination, the anchor 15*n* and/or free end 22*n* may be configured such that the one or more structures are not rotated, or are minimally rotated, during rotation of the anchor 15*n*. For example, the anchor 15*n* may comprise one or more spaces between loops of the spiral band (for example, spaces 18 shown in FIG. 57) which facilitate movement of the captured tissue (e.g. chordae and/or leaflets) from the free end 22*n* to the center of the spiral structure with little or no torque and/or rotation of the structures during rotation of the anchor 15*n* as described herein. Alternatively or in combination, the anchor 15*n* may be configured such that, when fully deployed (for example, as shown in FIG. 59), none of the structures reside between the loops of the spiral. Instead, the one or more structures may sit radially inward of the loops in order to facilitate capture of the one or more structures between the anchor 15*n* and the expanded frame structure 12*n*. The one or more structures may retain or nearly retain their normal anatomical position when the anchor 15*n* is fully deployed.

The anchor 15*n* may comprise a delivery (e.g. an elongated) configuration and a deployed configuration. The anchor 15*n* may be configured to be actuated from the delivery configuration to the deployed configuration adjacent a native valve in a patient. In various embodiments, the anchor 15*n* may have a generally spiral shape in the deployed configuration. In various embodiments, the anchor 15*n* may be elongated—rather than spiral-shaped—in the delivery configuration. For example, the anchor 15*n* may be elongated into a straight shape within the delivery device. In various embodiments, a portion of the anchor 15*n* may have a spiral shape. In various embodiments, a substantial portion of the anchor 15*n* may have a spiral shape. In various embodiments, the spiral anchor 15*n* may be formed as a flat spiral (in the deployed configuration) whereby the loops generally are positioned within the same plane (the plane being perpendicular to a longitudinal axis).

Anchor 15*n* may be formed of a material having sufficient rigidity to hold a predetermined shape. The wire may, for example, be formed of a shape memory material (e.g. NiTi). It may be desirable for at least an end portion (e.g. free end 22*n*) to be relatively rigid such that it can exert a force to move chordae tendineae, while still retaining flexibility to be collapsed within a delivery device. In various embodiments, the end portion only needs sufficient rigidity to hold its shape and will deform under a load. For example, the end portion may be configured with a similar rigidity to a guidewire, or slightly stiffer.

The anchor 15*n* may comprise a planar spiral band 17. The anchor 15*n* may comprise a spiral band 17 having a free end 22*n*. The other end of the spiral band 17 may be coupled to the top (proximal end) or bottom (distal end) of the frame structure 12*n* as described herein. Alternatively, or in combination, the other end of the spiral band 17 may not be attached to the frame structure 12*n* as described herein. The free end 22*n* of the spiral band 17 may facilitate capturing of the valve leaflets and/or chordae tendineae within the sweep of the free end during rotation as described herein. During rotation of the spiral band 17, the leaflets and/or chordae tendineae may be captured by the free end 22*n* and trapped between the valve frame structure 12*n* and an interior surface of the spiral band 17.

The free end 22*n* of the spiral band 17 may be sized and dimensioned for insertion through the native valve, for example through tissue at or near a commissure of the native valve or through the valve opening itself. In some embodiments, the free end 22*n* may comprise an atraumatic tip to avoid reduce risk of injury to the native valve tissue and leaflets. For example, the free end 22*n* may comprise a blunt end, a ball tip, a curved tip (e.g. J-tip or pigtail), or other atraumatic shapes. Alternatively, the free end 22*n* may be configured for piercing tissue. In various embodiments, the free end 22*n* is separate from and extends outward from the main coils of the anchor 15*n*. In various embodiments, the main body coils of the anchor 15*n* circumscribe an area (in the case of a spiral coil) or a volume (in the case of a helical coil) having a diameter, and the free end 22*n* extends to a radius greater than the diameter of the anchor 15*n*. In various embodiments, the free end 22*n* extends to a radius substantially greater than the diameter of the anchor 15*n*. In various embodiments, the free end 22*n* is configured to circumscribe a larger diameter than the anchor 15*n*. In various embodiments, the free end 22*n* is configured to circumscribe all of the chordae tendineae of the native valve to be treated.

The free end 22*n* of the spiral band 17 may optionally rotated around one or more structures on the second side of the native valve such that the one or more structures (e.g., chordae, leaflets, or annulus) are pulled radially inwards towards the longitudinal axis of the anchor 15*n* and/or towards the longitudinal axis of the delivery device 30*n*. The spiral band 17 and/or free end 22*n* may be configured such that minimal torque is applied to the one or more structures. Alternatively, or in combination, the spiral band 17 and/or free end 22*n* may be configured such that the one or more structures are not rotated, or are minimally rotated, during rotation of the spiral band 17. For example, the spiral band 17 may comprise one or more spaces between loops of the spiral band (for example, spaces 18 shown in FIG. 57) which facilitate movement of the captured tissue (e.g. chordae and/or leaflets) from the free end 22*n* to the center of the spiral structure with little or no torque and/or rotation of the structures during rotation of the spiral band 17 as described herein. Alternatively or in combination, the spiral band 17 may be configured such that, when fully deployed (for example, as shown in FIG. 59), none of the structures reside between the loops of the spiral. Instead, the one or more structures may sit radially inward of the loops in order to facilitate capture of the one or more structures between the spiral band 17 and the expanded frame structure 12*n*. The one or more structures may retain or nearly retain their normal anatomical position when the spiral band 17 is fully deployed.

The spiral band 17 may comprise a delivery (e.g. an elongated) configuration and a deployed configuration. The spiral band 17 may be configured to be actuated from the delivery configuration to the deployed configuration adjacent a native valve in a patient. In various embodiments, the band 17 may have a generally spiral shape in the deployed configuration. In various embodiments, the band 17 may be elongated—rather than spiral-shaped—in the delivery configuration. For example, the band 17 may be elongated into a straight shape within the delivery device. In various embodiments, a portion of the band 17 may have a spiral shape. In various embodiments, a substantial portion of the band 17 may have a spiral shape. In various embodiments, the spiral band 17 may be formed as a flat spiral (in the deployed configuration) whereby the loops generally are positioned within the same plane (the plane being perpendicular to a longitudinal axis).

Spiral band 17 may be formed of a material having sufficient rigidity to hold a predetermined shape. The wire may, for example, be formed of a shape memory material (e.g. NiTi). It may be desirable for at least an end portion (e.g. free end 22*n*) to be relatively rigid such that it can exert a force to move chordae tendineae, while still retaining flexibility to be collapsed within a delivery device. In various embodiments, the end portion only needs sufficient rigidity to hold its shape and will deform under a load. For example, the end portion may be configured with a similar rigidity to a guidewire, or slightly stiffer.

Figure 55:
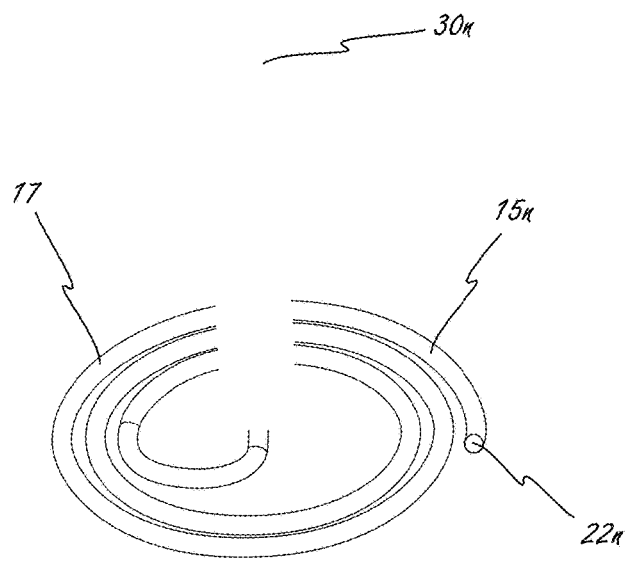
FIGS. 55-57 show several views of the anchor of FIGS. 52-54 loaded on a delivery device, in accordance with embodiments.
Figure 56:
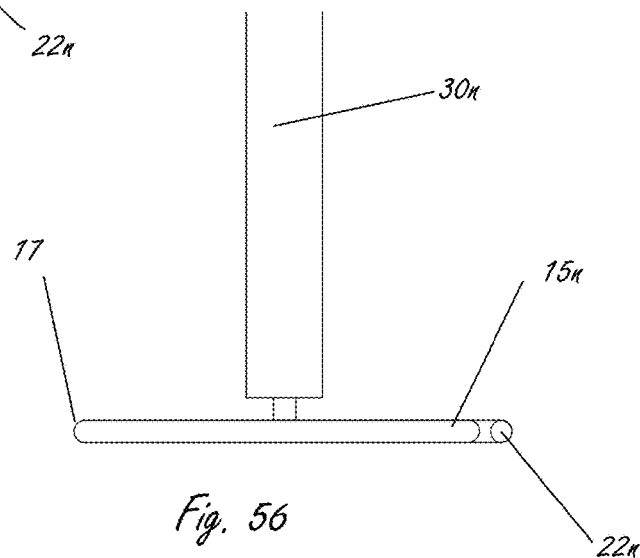
Figure 57:
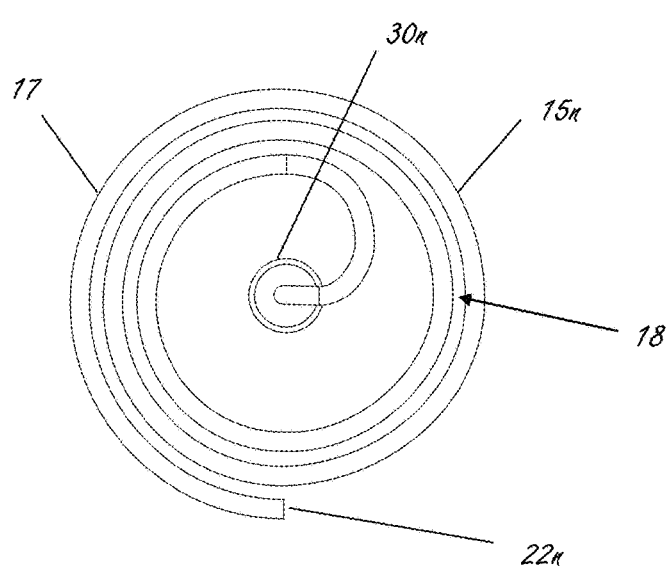

FIGS. 55-57 show several views of the flat spiral anchor 15*n* of FIGS. 52-54 loaded on a delivery device 30*n*. The delivery device 30*n* may be substantially similar to any of the delivery devices described herein. For example, the delivery device 30*n* may comprise an outer sheath in which the anchor 15*n* may be disposed, for example in an elongated or undeployed delivery configuration as described herein. Alternatively, or in combination, the delivery device 30*n* may comprise an inner shaft, for example disposed within the lumen of the outer sheath. The anchor 15*n* and/or frame structure 12*n* may be coupled to the inner shaft as described herein. The delivery device 30*n* may comprise a guidewire as described herein. The delivery device 30*n* may be configured to deliver the anchor 15*n* to the native valve as described herein. The manner of implanting valve device 10*n* may be substantially similar to any of the methods described herein.

The flat spiral anchor 15*n* (e.g., spiral band 17) may comprise one or more loops. For example, the anchor 15*n* may comprise a plurality of loops, which may increase the radial strength of the anchor by increasing friction and addition structural support. The one or more loops of the anchor 15*n* may be spiral radially outward from a central point or central axis of the spiral, for example along an axis which is coaxial with a longitudinal axis of a delivery device 30*n* such that the spiral anchor 15*n* lies approximately along a plane perpendicular to the longitudinal axis of the delivery device 30*n*.

The one or more loops (also referred to herein as coils or turns) of the flat spiral anchor 15*n* (e.g., spiral band 17) may comprise a shape that bends around back towards its origin (for example, an arc, ellipsoid, circle, or the like). In some embodiments, a loop may comprise a shape that bends back towards its origin but does not cross itself, making a rotation within a range of about 180 degrees to about 360 degrees. For example, a loop may comprise an arc having a central angle within a range of about 180 degrees to about 360 degrees. In at least some embodiments, the one or more loops may comprise an arc. In some embodiments, a loop may comprise a shape that bends back towards and crosses itself, making at least a 360 degree rotation. In at least some embodiments, the one or more loops may comprise a 360 degree rotation (for example, a circle). In some embodiments, the one or more loops may comprise a 360 degree to 720 degree rotation (for example, a loop crossing itself once and rotating further towards a second crossing and formation of a second 360 loop).

The one or more loops may comprise any number of loops desired, for example, one, two, three, four, five, six, seven, eight, nine, or ten loops. The one or more loops may comprise a rotation within a range of about 180 degrees to about 3600 degrees. The one or more loops may comprise a rotation within a range bounded by any of the following values: 180 degrees, 270 degrees, 360 degrees, 450 degrees, 540 degrees, 630 degrees, 720 degrees, 810 degrees, 900 degrees, 990 degrees, 1080 degrees, 1170 degrees, 1260 degrees, 1350 degrees, 1440 degrees, 1530 degrees, 1620 degrees, 1710 degrees, 1800 degrees, 1890 degrees, 1980 degrees, 2070 degrees, 2160 degrees, 2250 degrees, 2340 degrees, 2430 degrees, 2520 degrees, 2610 degrees, 2700 degrees, 2790 degrees, 2880 degrees, 2970 degrees, 3060 degrees, 3150 degrees, 3240 degrees, 3330 degrees, 3420 degrees, 3510 degrees, or 3600 degrees.

In some embodiments, for example when the free end 22 is disposed at an angle (upward, downward, or radially outward) relative to the rest of the anchor body, the main body of the anchor comprises the one or more loops and the rotation of the one or more loops may be determined without taking into account the angled free end 22.

Interaction of the frame structure 12*n* with the one or more loops of the anchor 15*n* may create opposing forces therebetween that provide mechanical leverage for anchoring the frame structure to the one or more anatomical structures. In some embodiments, the one or more loops may comprise at least 360 degrees of rotation (e.g., 540 degrees) when deployed such that the loops wrap around one another and provide additional mechanical leverage against the frame structure in order to facilitate anchoring of the frame structure as described herein. Additional loops or partial loops may provide additional mechanical strength and/or leverage.

In some embodiments, the one or more loops may comprise a rotation of about 540 degrees. A first loop may comprise a rotation of 360 degrees and a second loop may comprise a rotation of about 180 degrees. The second loop may wrap around the first loop for about 180 degrees in order to provide additional mechanical strength and/or leverage against the frame structure in order to facilitate anchor of the frame structure. In some instances, the one or more loops comprising a rotation of about 540 degrees may facilitate easier and safer capture of the chordae tendineae and/or valve leaflets than an anchor having additional loops by providing sufficient mechanical strength and/or leverage and/or radial stability while reducing or minimizing the amount of overlap between loops in which to potentially ensnare or entangle the native valve structures during rotation.

In some embodiments, the one or more loops of the anchor 15*n* may comprise one or more spaces 18 therebetween. The spaces 18 may facilitate movement of the captured tissue (e.g. chordae and/or leaflets) from the free end 22*n* to the center of the spiral structure during rotation of the anchor 15*n* as described herein.

The anchor 15*n* (e.g., spiral band 17) may comprise a spiral wire. The anchor 15*n* may comprise a plurality of spiral wires as described herein.

In some embodiments, the delivery device 30*n* may be configured to carry the anchor 15*n* in an undeployed configuration and deploy the anchor 15*n* into a deployed configuration as the desired location as described herein.

In some embodiments, the anchor 15*n* may be configured to wrap at least partially around a distal portion of the delivery device 30*n*, for example around the inner shaft, in the deployed configuration.

In some embodiments, the anchor 15*n* may comprise one or more locking mechanisms configured to maintain the anchor 15*n* in the deployed configuration. The one or more locking mechanisms may be any of the locking mechanisms described herein or understood by one of ordinary skill in the art from the description herein. In various embodiments, one or more loops may be nested with each other when the anchor is in the deployed configuration.

Figure 58:
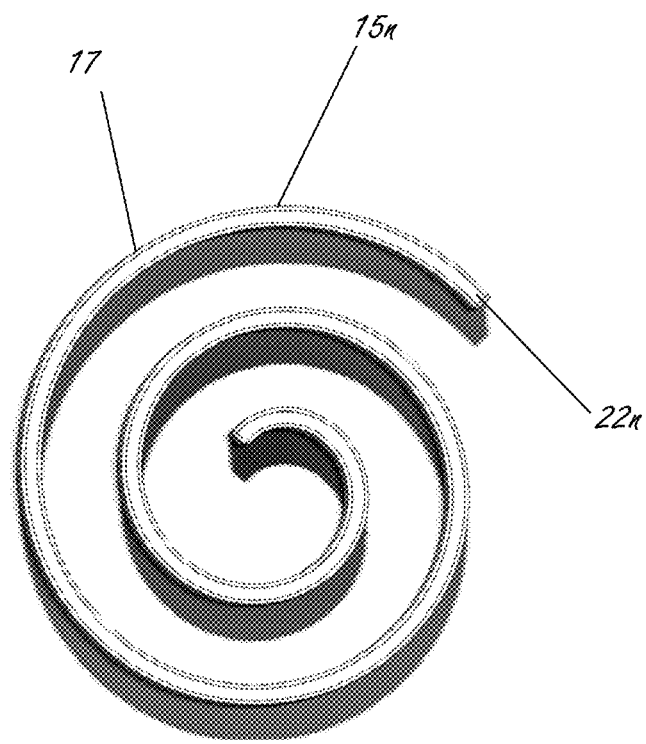
FIGS. 58-59 show deployment of the anchor of FIGS. 52-54 from an unexpanded, undeployed configuration (FIG. 58) to an expanded, deployed configuration (FIG. 59), in accordance with embodiments.

FIGS. 58-59 show deployment of the anchor of FIGS. 52-54 from an undeployed configuration (FIG. 58) to a deployed configuration (FIG. 59). The anchor 15*n* may comprise an undeployed configuration (shown in FIG. 58) and a deployed configuration (shown in FIG. 59). The anchor 15*n* may be configured to be actuated from the undeployed configuration to the deployed configuration adjacent the native valve. The anchor 15*n* may comprise a spiral band 17. The anchor 15*n* may comprise a flat spiral or planar spiral shape in the deployed configuration. The free end 22*n* of the anchor 15*n* may extend radially outward from the frame 12*n*, and in particular from the remainder of the anchor 15*n*. In some embodiments, expansion of the frame structure 12*n* inside the anchor 15*n* may cause the anchor 15*n* to expand from the undeployed configuration to the deployed configuration. Alternatively, or in combination, rotation of the anchor 15*n* around one or more structures as described herein may cause the anchor 15*n* to expand from the undeployed configuration to the deployed configuration.

In some embodiments, the anchor 15*n* may comprise a delivery (e.g., elongated) configuration when disposed within a delivery device as described herein. The delivery device may be configured to deploy the anchor 15*n* from the elongated configuration to a first intermediate deployed configuration (substantially similar to the undeployed configuration shown in FIG. 58) as described herein. The anchor 15*n* may then be actuated into the second fully deployed configuration (substantially similar to the deployed configuration shown in FIG. 59), for example by expanding the frame structure within the anchor 15*n* or by rotating the anchor 15*n* to capture the one or more structures as described herein.

The anchor 15*n* may comprise one or more loops of a spiral as described herein. The anchor 15*n* may comprise a more compact spiral, with more loops, in the undeployed configuration compared to the deployed configuration. As the anchor 15*n* expands the spiral loops may unwind.

In some embodiments, the outer perimeter of the anchor 15*n* (e.g., spiral band 17) may be substantially similar in the undeployed and deployed configurations. As the spiral loops unwind, the spiral may expand from the center, for example simultaneously with expansion of the frame structure in the center of spiral anchor 15*n*, such that the spiral loops are expanded against one another as shown in FIG. 59. As will be understood by one of ordinary skill in the art, the shape, size, and number of loops may determine the limits of expansion of the spiral anchor 15*n* and alteration of any or all of these parameters may be done to generate a final deployed configuration desired from an initial undeployed configuration.

Figure 60:
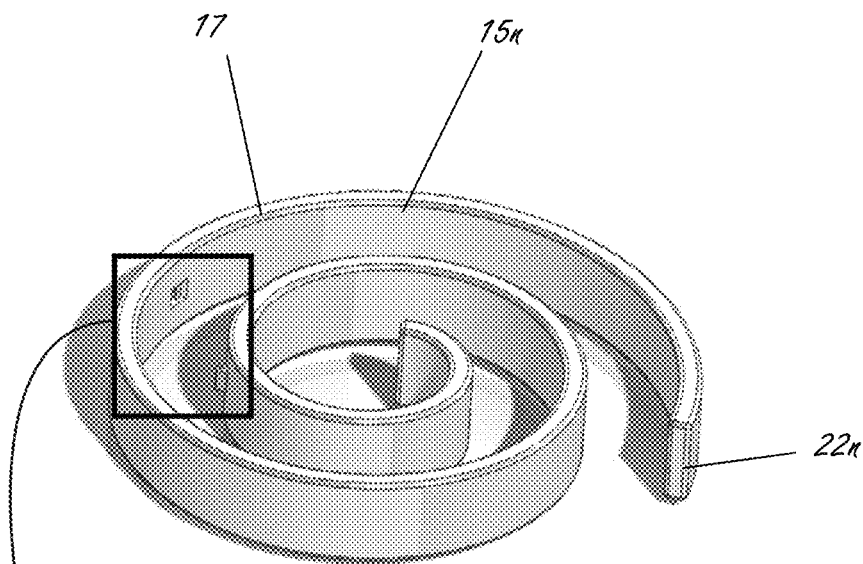
FIGS. 60-61 show an optional locking mechanism for a spiral band anchor, in accordance with embodiments.
Figure 61:
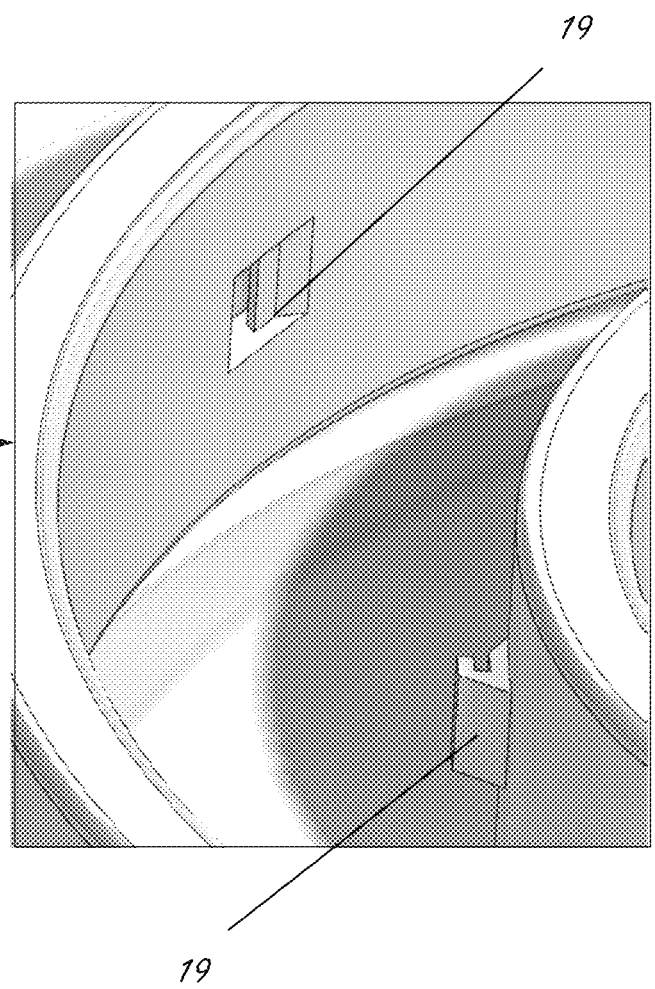

FIGS. 60-61 show an optional locking mechanism for a spiral band anchor. Anchor 15*n* may comprise a spiral band 17. The anchor 15*n* may comprise one or more optional locking features disposed along the spiral loops such that they interlock when expanded against one another. For example, the locking features may comprise one or more "key-in-hole" (e.g., key and key hole) interlocking features 19 as shown which lock the spiral anchor 15*n* in a deployed configuration when the spiral loops are expanded such that the two corresponding features meet and connect. In some instances, it may be beneficial to provide the spiral anchor 15*n* with a plurality of locking features, for example to ensure secure locking and/or to provide for a plurality of intermediate expanded/deployed configurations between the fully undeployed and the fully deployed configuration. It will be understood by one of ordinary skill in that any number or style of locking features may be used to lock the spiral anchor 15*n* into a deployed (and/or intermediately deployed) configuration.

Figure 62:
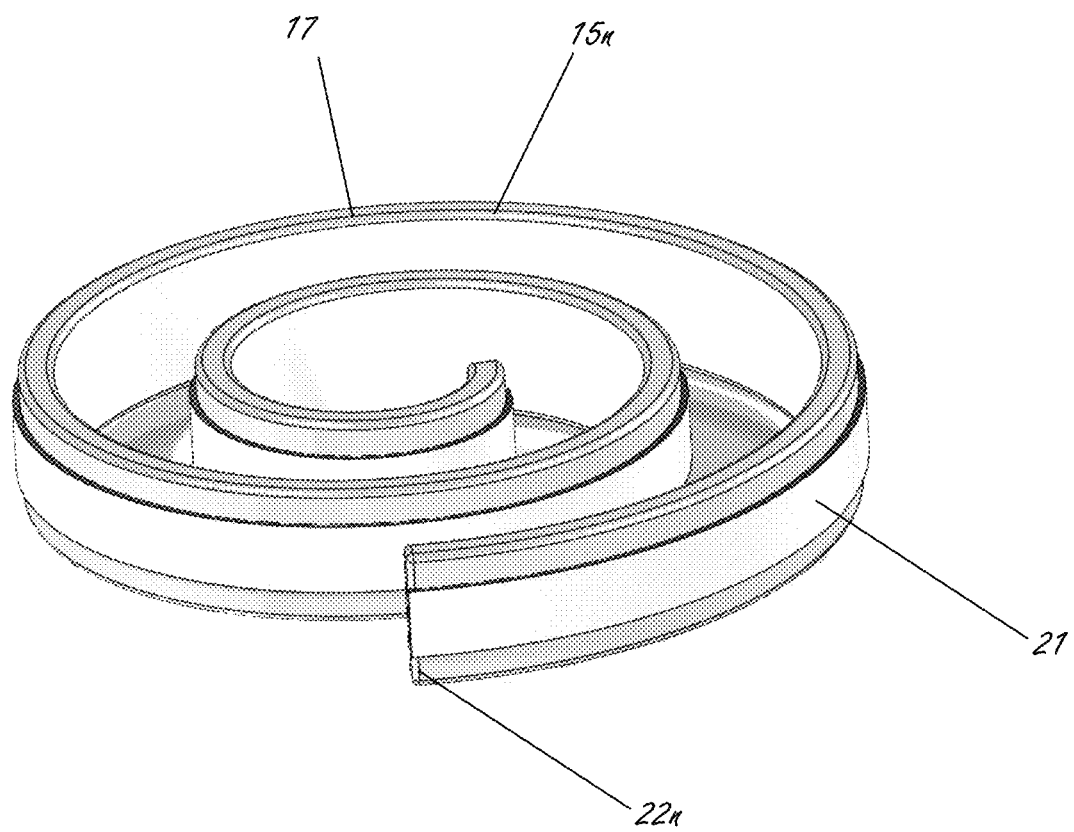
FIG. 62 shows another optional locking mechanism for a spiral band anchor, in accordance with embodiments.

FIG. 62 shows another optional locking mechanism for a spiral band anchor. Anchor 15*n* may comprise a spiral band 17. The anchor 15*n* may comprise an optional frictional band 21 disposed upon a length of the anchor 15*n* which may facilitate locking the anchor 15*n* in a deployed configuration as the spiral loops expand. By adding a frictional texture or band 21 to at least a portion of the anchor 15*n*, the loops may be encouraged to engage one another as they are expanded against each other.

The frictional band 21 may, for example comprise a strip of frictional material that may be bonded to the surface of the anchor 15*n* by any method understood by one of ordinary skill in the art from the description herein.

Alternatively, or in combination, at least a portion of the anchor 15*n* may be coated with a polymer and the outer surface of the polymer may be made rough using any technique understood by one of ordinary skill in the art from the description herein.

Alternatively, or in combination, the surface of the anchor 15*n* may be directly altered for increased friction to form the frictional band 21 using any technique understood by one of ordinary skill in the art from the description herein.

FIGS. 63-64 show an optional tip orientation for a spiral anchor. In some embodiments, the spiral anchor 15*n*, which may comprise a spiral band 17, may comprise a free end 22*n* which is angled or bent such that it points upwards towards the proximal direction of the delivery device 30*n*. FIGS. 65-66 show another optional tip orientation for a spiral anchor, which may comprise a spiral band 17. In some embodiments, the spiral anchor 15*n* may comprise a free end 22*n* which is angled or bent such that it points downwards towards the distal direction of the delivery device 30*n*. Angling the free end 22*n* distally or proximally, or otherwise disposing the free end 22*n* away from the rest of the anchor 15*n* (for example radially outward therefrom), may aid in deployment of the anchor 15*n* from the delivery device and/or capture of the one or more structures (e.g., chordae tendineae, leaflets, etc.).

Figure 67:
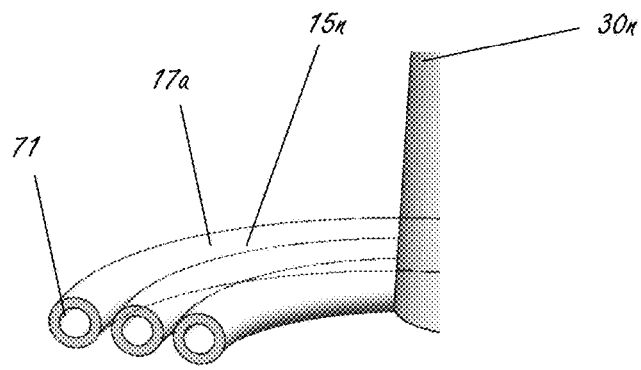
FIGS. 67-69 show various optional configurations for a spiral band anchor, in accordance with embodiments.
Figure 68:
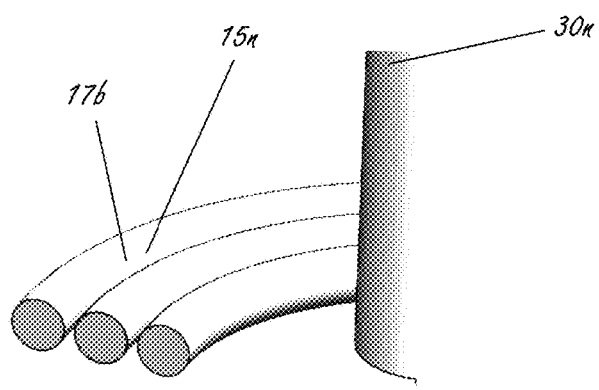
Figure 69:
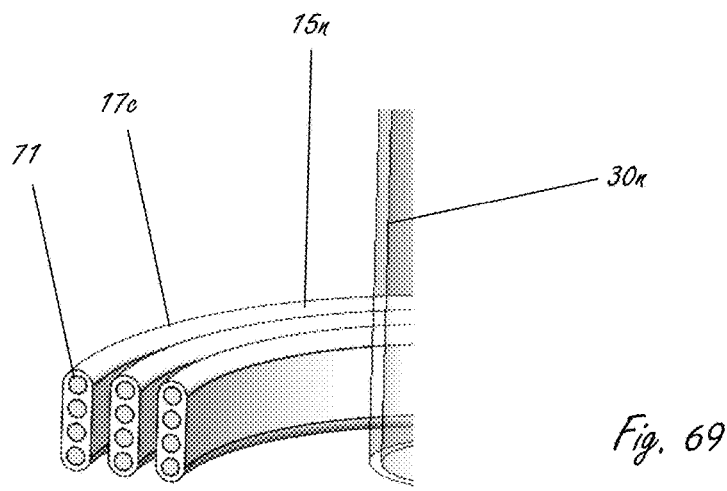

FIGS. 67-69 show various optional configurations for a spiral anchor. FIG. 67 shows an anchor 15*n* comprising a spiral band 17*a* having a hollow, tubular cross-section. The spiral anchor 15*n* may, for example, comprise a hypotube. The anchor 15*n* may be configured to pass another component (e.g. a wire, guidewire, etc.) therethrough. FIG. 68 shows a spiral band 17*b* which may comprise a solid, circular cross-section. The spiral band 17*b* may, for example, comprise a wire. FIG. 69 shows a spiral band 17*c* with a non-round, elongated cross-section comprising a plurality of channels disposed therein. Four channels are shown but it will be understood to one of ordinary skill in the art that any number of channels may be utilized as desired. The channels may for example be left as open lumens. Alternatively, or in combination, the channels may be filled, for example with one or more stiffening members. For example, at least one channel may be open and at least one channel may be filled.

The spiral anchor 15*n* may have a cross-section of any shape desired, for example a circular, tubular (e.g. hollow), square, elongated, triangular, or any other shaped cross-section. The spiral anchor 15n may comprise a solid anchor, or the spiral anchor may comprise one, two, three, four, five, or more lumens or channels disposed therein. The lumens or channels 71 may be open lumens and/or filled channels, for example with one or more stiffening members, guidewires, or the like. It will be understood by one of ordinary skill in the art that the spiral anchor may have any configuration, or combination of configurations, described herein or understood by one of ordinary skill in the art from the description herein.

For example, the one or more lumens or channels 71 may be configured to hold one or more stiffening members in order to provide structural support to the anchor 15n. Alternatively, or in combination, the anchor 15n may be delivered to the heart over a guidewire(s) translatably and removably disposed within one or more of the lumens of channels 71.

The spiral band 17 may have a cross-section of any shape desired, for example a circular, tubular (e.g. hollow), square, elongated, triangular, or any other shaped cross-section. The spiral band may comprise a solid band, or the spiral band may comprise one, two, three, four, five, or more lumens or channels disposed therein. The lumens or channels 71 may be open lumens and/or filled channels, for example with one or more stiffening members, guidewires, or the like. It will be understood by one of ordinary skill in the art that the spiral band may have any configuration, or combination of configurations, described herein or understood by one of ordinary skill in the art from the description herein.

Figure 70:
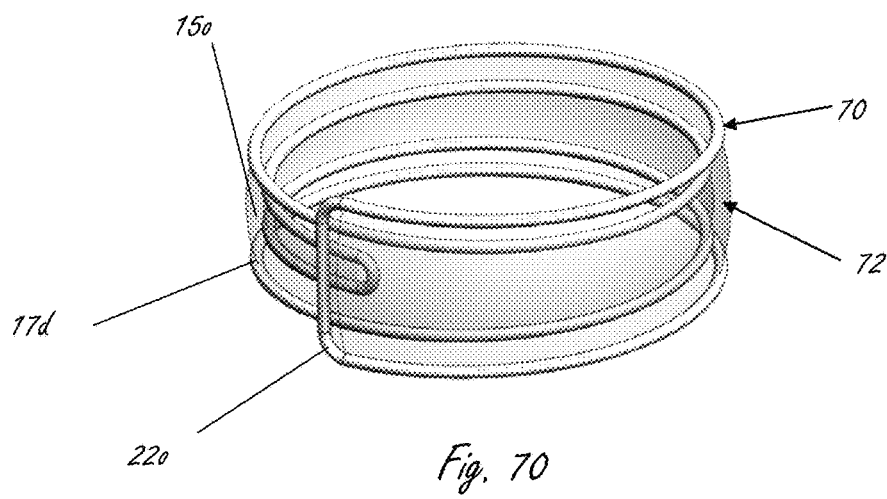
FIGS. 70-72 show several views of an anchor comprising a tapered spiral band, in accordance with embodiments.
Figure 71:
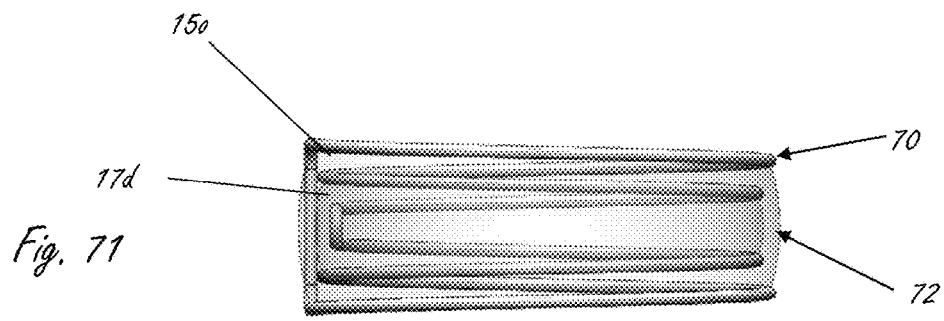
Figure 72:
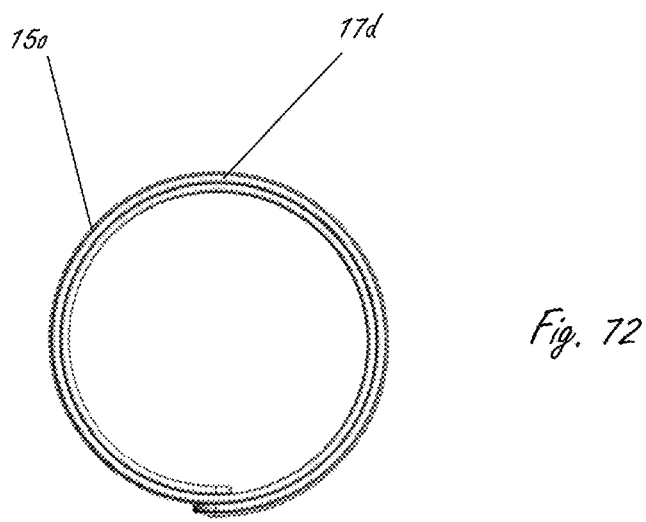

FIGS. 70-72 show several views of an anchor 15o comprising a spiral band 17. The spiral band 17 may be a tapered spiral band 17d. Tapered spiral band 17d may be deployed and configured to anchor a frame structure of a valve prosthesis adjacent a native valve as described herein. The anchor 15o may, for example, be configured to be fully advanced from a first side of a native valve in a patient (e.g. an atrial side) to a second side of the native valve (e.g. into a ventricle of the heart) and anchor a frame structure to the native valve when the frame structure is in an expanded configuration adjacent the native valve as described herein. The tapered spiral band 17d may comprise a delivery (e.g., elongated) configuration and a deployed configuration (and optional intermediate configurations) substantially similar to those shown in FIGS. 52-69. The tapered spiral band 17d may be configured to be actuated from the elongated configuration to the deployed configuration adjacent a native valve in a patient. The tapered spiral band 17d may be delivered to the native valve by a delivery device as described herein. The tapered spiral band 17d may be deployed adjacent the native valve substantially similarly to other anchor embodiments as described herein. In some embodiments, the anchor 15o may comprise one or more locking mechanisms configured to maintain the anchor 15o in the deployed configuration. The one or more locking mechanisms may be any of the locking mechanisms described herein or understood by one of ordinary skill in the art from the description herein.

The anchor 15o may comprise a tapered spiral band 17d having a free end 22o. The other end of the tapered spiral band 17d may be coupled to the top (proximal end) or bottom (distal end) of a frame structure as described herein. Alternatively, or in combination, the other end of the tapered spiral band 17d may not be attached to a frame structure as described herein. The free end 22o of the tapered spiral band 17d may facilitate capturing of the valve leaflets and/or chordal tendineae within the sweep of the free end 22o during rotation as described herein. During rotation of the tapered spiral band 17d, the leaflets and/or chordae tendineae may be captured by the free end 22o and trapped between the valve frame structure and an interior surface of the spiral band 17d.

The free end 22o of the spiral band 17d may be sized and dimensioned for insertion through the native valve, for example through tissue at or near a commissure of the native valve or through the valve opening itself. In some embodiments, the free end 22o may comprise an atraumatic tip to avoid reduce risk of injury to the native valve tissue and leaflets. For example, the free end may comprise a blunt end, a ball tip, a curved tip (e.g. J-tip or pigtail), or other atraumatic shapes. Alternatively, the free end 22o may be configured for piercing tissue. In various embodiments, the free end 22o is separate from and extends outward from the main coils of the anchor 15o. In various embodiments, the main body coils of the anchor 15o circumscribe an area (in the case of a spiral coil) or a volume (in the case of a helical coil) having a diameter, and the free end 22o extends to a radius greater than the diameter of the anchor 15o. In various embodiments, the free end 22o extends to a radius substantially greater than the diameter of the anchor 15o. In various embodiments, the free end 22o is configured to circumscribe a larger diameter than the anchor 15o. In various embodiments, the free end 22o is configured to circumscribe all of the chordae tendineae of the native valve to be treated.

The free end 22o of the tapered spiral band 17d may optionally be rotated around one or more structures on the second side of the native valve such that the one or more structures (e.g., chordae, leaflets, or annulus) are pulled radially inwards towards the longitudinal axis of the anchor 15o and/or towards the longitudinal axis of the delivery device 30. The spiral band 17d and/or free end 22o may be configured such that minimal torque is applied to the one or more structures. Alternatively, or in combination, the tapered spiral band 17d and/or free end 22o may be configured such that the one or more structures are not rotated, or are minimally rotated, during rotation of the spiral band 17d. For example, the spiral band 17d may comprise one or more spaces between loops of the spiral band (for example, spaces 18 shown in FIG. 57) which facilitate movement of the captured tissue (e.g. chordae and/or leaflets) from the free end 22o to the center of the spiral structure with little or no torque and/or rotation of the structures during rotation of the tapered spiral band 17d as described herein. Alternatively or in combination, the spiral band 17d may be configured such that, when fully deployed (for example, as shown in FIG. 72), none of the structures reside between the loops of the spiral. Instead, the one or more structures may sit radially inward of the loops in order to facilitate capture of the one or more structures between the spiral band 17d and the expanded frame structure as described herein. The one or more structures may retain or nearly retain their normal anatomical position when the spiral band 17d is fully deployed.

Spiral band 17d may be configured to taper in height axially. For example, spiral band 17d may be configured to taper in height from a first end of the spiral band 17d, which may be coupled to a delivery device and/or frame structure as described herein, to a free end 22o of the spiral band 17d. In some embodiments, the spiral band 17d may taper in height from a proximal end to a distal end. Alternatively, the spiral band 17d may taper in height from a distal end to a proximal end.

The spiral band 17d may be tapered such that subsequent turns of the tapered spiral band 17d nest into each other so as to reduce a radial footprint of the tapered spiral band.

The spiral band 17*d* may, for example, comprise a solid wire-like spiral band similar to that shown in FIG. 64 but with a taper as described herein. In some embodiments, the spiral band 17*d* may comprise a plurality of spiral support wires.

Alternatively, or in combination, at least a portion of the tapered spiral band may comprise a support structure 70 and a band material 72 disposed therein (or thereon as desired by one of ordinary skill in the art).

The support structure 70 may, for example, comprise a wire. The support structure 70 may be formed of a material having sufficient rigidity to hold a predetermined shape. The support structure 70 may, for example, be formed of a shape memory material (e.g. NiTi). It may be desirable for at least an end portion (e.g. free end 22*o*) to be relatively rigid such that it can exert a force to move chordal tendineae, while still retaining flexibility to be collapsed within a delivery device. In various embodiments, the end portion only needs sufficient rigidity to hold its shape and will deform under a load. For example, the end portion may be configured with a similar rigidity to a guidewire, or slightly stiffer.

The band material 72 may comprise a permeable, semi-permeable, or impermeable material. The band material 72 may be flexible, semi-flexible, or rigid. In some embodiments, the band material 72 may be relatively soft so as to reduce the risk of injury to the one or more structures during rotation of the tapered spiral band 17*d*. The band material 72 may, for example, comprise a webbing material, a fabric, a polymeric material, an elastomeric material, or the like. The band material 72 may span the structural support 70 so as to reduce leakage therethrough. Alternatively, or in combination, the band material 72 may be configured to improve alignment of the support structure 70 wire.

It will be understood by one of ordinary skill in the art from the description herein that any of the anchors 15 described herein may comprise a support structure and a material disposed therein or thereon as described with referenced to tapered spiral band 17*d*.

The tapered spiral band 17*d* may comprise one or more loops. For example, the spiral band 17*d* may comprise a plurality of loops, which may increase the radial strength of the anchor by increasing friction and addition structural support. The one or more loops of the spiral band 17*d* may be spiral radially outward from a central point or central axis of the spiral, for example along an axis which is coaxial with a longitudinal axis of a delivery device 30*n* such that the spiral band 17*d* lies approximately along a plane perpendicular to the longitudinal axis of a delivery device.

In some embodiments, the one or more loops of the spiral band 17*d* may comprise one or more spaces therebetween, which may be substantially similar to spaces 18 shown in FIG. 57. The spaces may facilitate movement of the captured tissue (e.g. chordae and/or leaflets) from the free end 22*o* to the center of the spiral structure during rotation of the anchor 15*o* as described herein.

In some embodiments, the support structure 70 may comprise one or more channels or lumens 71 disposed therein. The support structure 70 may comprise a hollow, tubular cross-section. The support structure 70 may, for example, comprise a hypotube. The lumen of the support structure 70 may be configured to pass another component (e.g. a wire, guidewire, etc.) therethrough.

Figure 73:
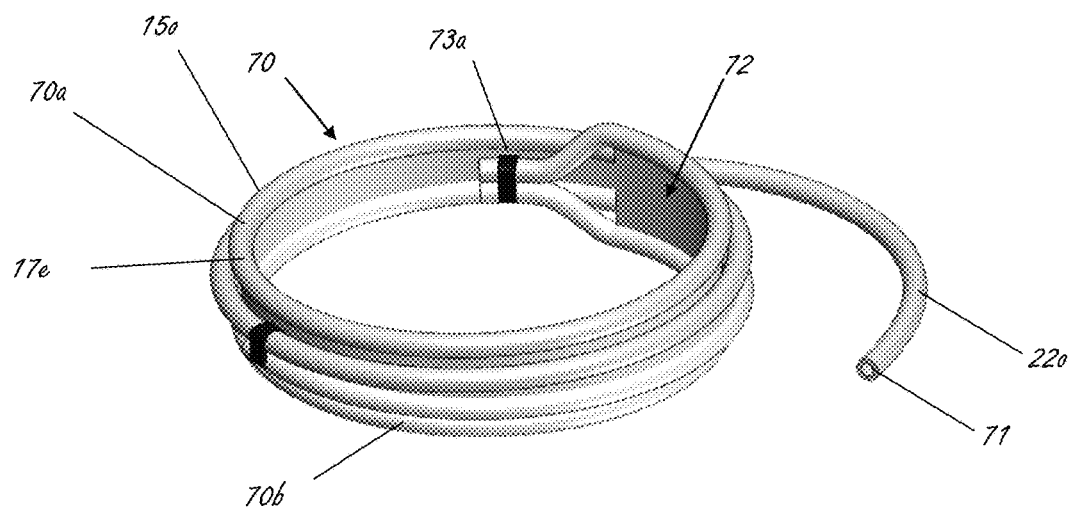
FIGS. 73-76 show several views of another anchor comprising a tapered spiral band, in accordance with embodiments.
Figure 74:
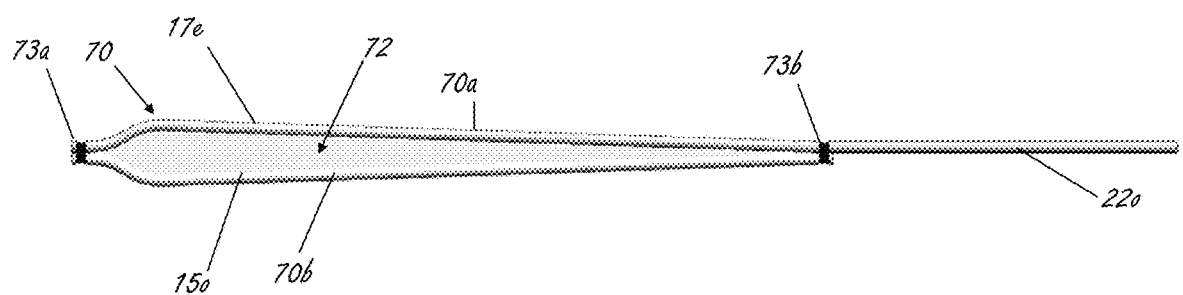
Figure 75:
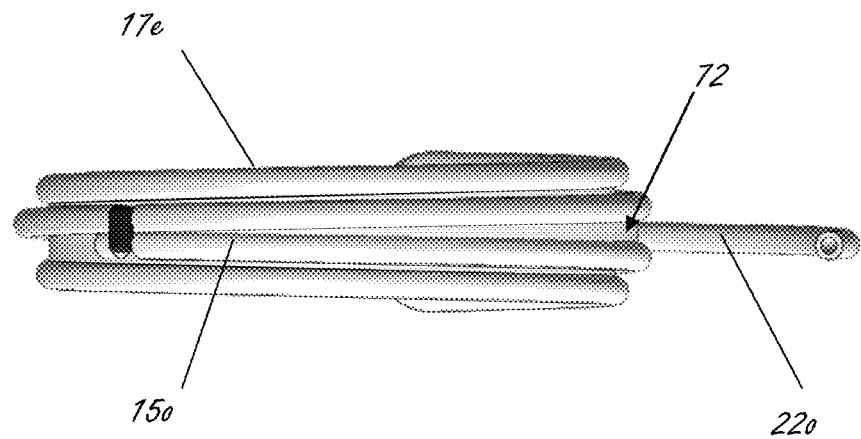
Figure 76:
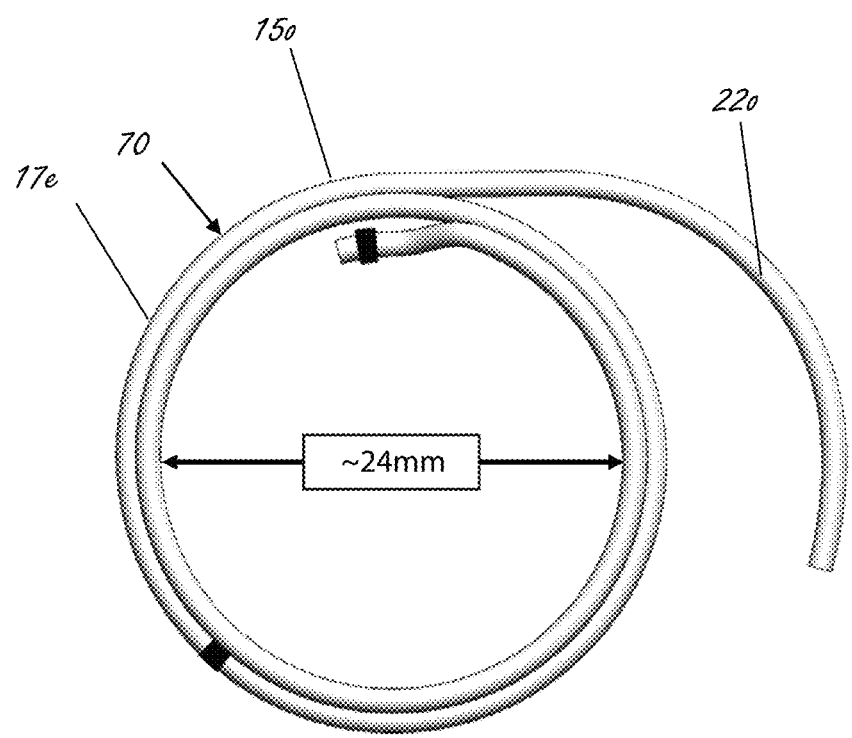

FIGS. 73-76 show several views of another anchor 15*o* comprising a tapered spiral band 17*e*. FIGS. 73, 75, and 76 show the anchor 15*o* in a deployed configuration. FIG. 74 shows the anchor 15*o* in an elongated delivery configuration. The spiral band 17*e* may be substantially similar to tapered spiral band 17*d* shown in FIGS. 70-72 except that the support structure 70 may comprise more than one wire. The support structure 70 may, for example, comprise an upper wire 70*a* and a lower wire 70*b*. The wires 70*a*, 70*b* may be coupled to one another at a proximal attachment point 73*a* and/or a distal attachment point 73*b*. The wires 70*a*, 70*b* may be round wires or have other cross-sectional shapes. In various embodiments, the support structure 70 may comprise a scaffold such as a laser-etched Nitinol scaffold or a mesh. The spiral band 17*e* may be tapered such that subsequent turns of the tapered spiral band 17*e* nest into each other so as to reduce a radial footprint of the tapered spiral band. Wires 70*a*, 70*b* may be configured to nest with one another when the in the deployed configuration.

The tapered spiral band 17*e* may comprise a delivery (e.g., elongated) configuration and a deployed configuration (and optional intermediate configurations) as described herein. The tapered spiral band 17*e* may be configured to be actuated from the elongated configuration to the deployed configuration adjacent a native valve in a patient. The tapered spiral band 17*e* may be delivered to the native valve by a delivery device in the elongated configuration as described herein. The tapered spiral band 17*e* may be coupled to the delivery device and/or a frame structure of a valve prosthesis as described herein, for example at a proximal portion (e.g. adjacent proximal attachment point 73*a* on an interior of the spiral) or distal portion (e.g. adjacent distal attachment point 73*b* on an exterior of the spiral) thereof. The tapered spiral band 17*e* may be deployed adjacent the native valve substantially similarly to other anchor embodiments as described herein.

In some embodiments, the upper wire 70*a* and lower wire 70*b* may be bundled together during deployment from an undeployed configuration to an intermediate deployed configuration. The intermediate configuration may be configured to reduce the size the size of the lumen and/or aperture in or through which, respectively, the spiral anchor 15*o* may travel (for example, a lumen or aperture of the delivery device) during deployment. The anchor 15*o* may be maintained in the intermediate configuration during rotation around the one or more structures as described herein. In at least some instances, coupling the wires 70*a*, 70*b* together into an intermediate configuration may facilitate alignment of the wires making up the support structure 70. After delivery from the delivery device and/or rotation around one or more structures, the anchor 15*o* may be fully deployed into the deployed configuration by releasing the bundle and allowing the wires 70*a*, 70*b* to "spring out" into the deployed configuration.

The support structure 70 may have a band material 72 disposed therein or thereon as described herein. The band material 72 may span the distance between wires 70*a*, 70*b* in order to couple the wires 70*a*, 70*b* to one another. The band material 72 may span the structural support 70 so as to reduce leakage therethrough as described herein. Alternatively, or in combination, the band material 72 may be configured to improve alignment of the support structure 70 wires 70*a*, 70*b* such that they maintain a desired relative position to one another.

The anchor 15*o* may comprise a free end 22*o*. The free end 22*o* may be substantially similar to any of free ends described herein. The other end of the tapered spiral band 17*e* may be coupled to the top (proximal end) or bottom (distal end) of a frame structure as described herein. Alternatively, or in combination, the other end of the tapered spiral band 17*e* may not be attached to a frame structure as described herein. The free end 22*o* of the tapered spiral band 17e may facilitate capturing of the valve leaflets and/or chordal tendineae within the sweep of the free end 22o during rotation as described herein. During rotation of the tapered spiral band 17e, the leaflets and/or chordae tendineae may be captured by the free end 22o and trapped between the valve frame structure and an interior surface of the spiral band 17e against the support structure 70 and/or band material 72.

The free end 22o of the spiral band 17e may be sized and dimensioned for insertion through the native valve, for example through tissue at or near a commissure of the native valve or through the valve opening itself. In some embodiments, the free end 22o may comprise an atraumatic tip to avoid reduce risk of injury to the native valve tissue and leaflets. For example, the free end may comprise a blunt end, a ball tip, a curved tip (e.g. J-tip or pigtail), or other atraumatic shapes. Alternatively, the free end 22o may be configured for piercing tissue. In various embodiments, the free end 22o is separate from and extends outward from the main coils of the anchor 15o. In various embodiments, the main body coils of the anchor 15o circumscribe an area (in the case of a spiral coil) or a volume (in the case of a helical coil) having a diameter, and the free end 22o extends to a radius greater than the diameter of the anchor 15o. In various embodiments, the free end 22o extends to a radius substantially greater than the diameter of the anchor 15o. In various embodiments, the free end 22o is configured to circumscribe a larger diameter than the anchor 15o. In various embodiments, the free end 22o is configured to circumscribe all of the chordae tendineae of the native valve to be treated. In various embodiments, the free end 22o may be shaped and configured to reduce the risk of counterrotation. For example, the tip 22o may have a curled end to cause the free end 22o to snag chordae if it is rotated in a direction opposite the anchoring rotation.

The free end 22o of the tapered spiral band 17e may optionally rotated around one or more structures on the second side of the native valve such that the one or more structures (e.g., chordae, leaflets, or annulus) are pulled radially inwards towards the longitudinal axis of the anchor 15o and/or towards the longitudinal axis of the delivery device 30. The spiral band 17e and/or free end 22o may be configured such that minimal torque is applied to the one or more structures. Alternatively, or in combination, the tapered spiral band 17e and/or free end 22o may be configured such that the one or more structures are not rotated, or are minimally rotated, during rotation of the spiral band 17e. For example, the spiral band 17e may comprise one or more spaces between loops of the spiral band (for example, spaces 18 shown in FIG. 57) which facilitate movement of the captured tissue (e.g. chordae and/or leaflets) from the free end 22o to the center of the spiral structure with little or no torque and/or rotation of the structures during rotation of the tapered spiral band 17e as described herein. Alternatively or in combination, the spiral band 17e may be configured such that, when fully deployed (for example, as shown in FIG. 76), none of the structures reside between the loops of the spiral. Instead, the one or more structures may sit radially inward of the loops in order to facilitate capture of the one or more structures between the spiral band 17e and the expanded frame structure as described herein. The one or more structures may retain or nearly retain their normal anatomical position when the spiral band 17e is fully deployed.

The free end 22o may be disposed radially outwards from the support structure 70. Disposing the free end 22o radially outward from the remainder of support structure 70 may, for example, aid in deployment of the anchor 15o from the delivery device and/or capture of the one or more structures as described herein.

The free end 22o may be angled proximally (e.g., towards a proximal portion of the anchor 15o and a distal end of the delivery device 30) or distally (e.g., away from a proximal portion of the anchor 15o and towards a proximal portion of the delivery device 30) from the support structure 70. Angling the free end 22o proximally or distally towards or away from the delivery device may, for example, aid in deployment of the anchor 15o from the delivery device and/or capture of the one or more structures as described herein.

In some embodiments, the support structure 70 may comprise one or more channels or lumens 71 disposed therein. For example, one or more of the wires 70a, 70b may comprise one or more channels or lumens 71. One or more of the wires 70a, 70b may comprise a hollow, tubular cross-section. The spiral band 17e may, for example, comprise a hypotube. The lumen of the spiral band 17e may be configured to pass another component (e.g. a wire, guidewire, etc.) therethrough. The channels or lumens 71 may for example be left as open lumens. Alternatively, or in combination, the channels or lumens 71 may be filled, for example with one or more stiffening members.

Figure 77:
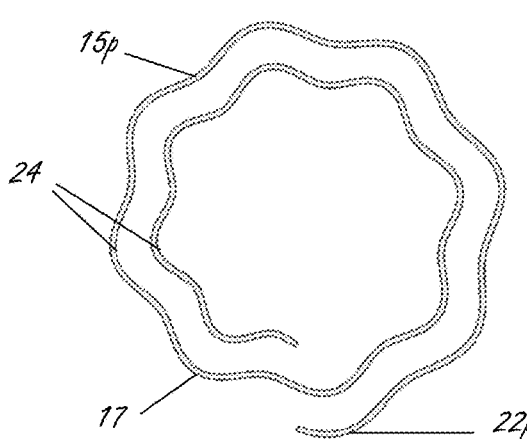
FIGS. 77-80 show several views of an optional locking mechanism for a spiral band anchor, in accordance with embodiments.
Figure 78:
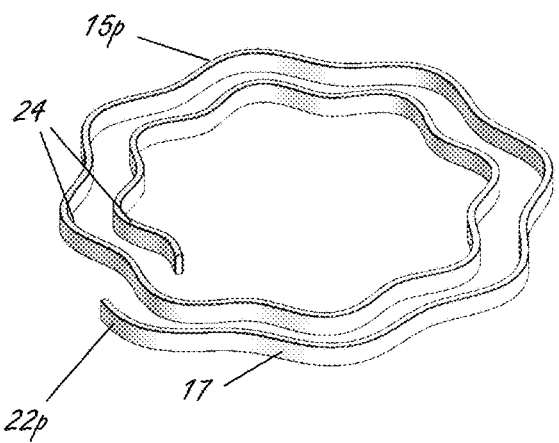
Figure 79:
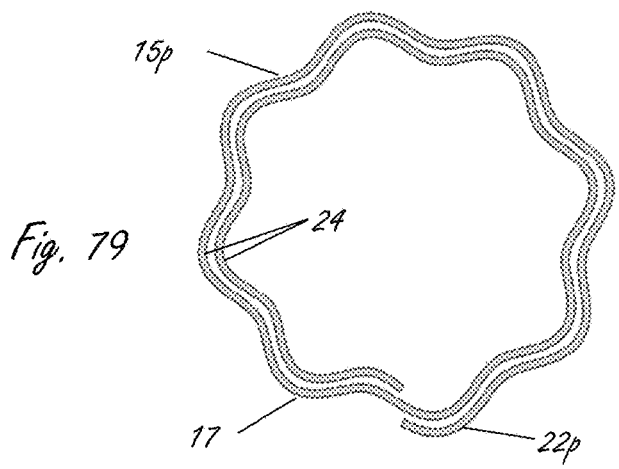
Figure 80:
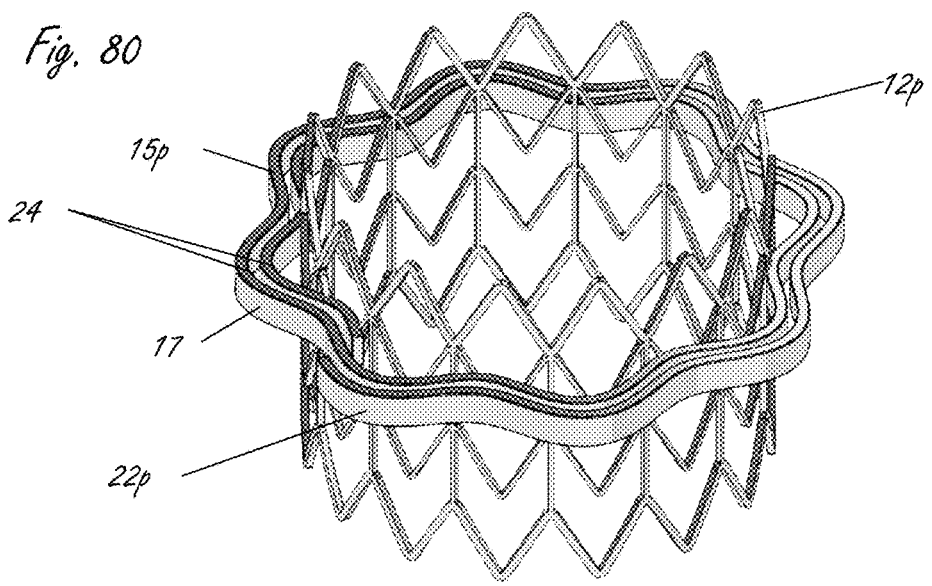

FIGS. 77-80 show several views of an optional locking mechanism for a flat spiral anchor. FIG. 77 shows a top view of a flat spiral anchor 15p comprising a spiral band 17 having a plurality of interlocking features 24 disposed thereon in an intermediate deployed or undeployed configuration (which may be substantially similar to the configurations shown in FIGS. 58-59 and described herein). FIG. 78 shows a perspective view of the spiral band anchor 15p in the undeployed configuration. FIG. 79 shows a top view of the spiral band anchor in a fully deployed configuration. FIG. 80 shows a perspective view of a valve prosthesis 10p comprising the spiral band anchor 15p in the deployed configuration disposed around a frame structure 12p in an expanded configuration.

The valve prosthesis 10p may be substantially similar to any of the valve prostheses described herein. The frame structure 12p may have an unexpanded configuration (for example, a compressed configuration as described herein) and an expanded configuration as described herein. The frame structure 12p may be substantially similar to any of the frame structures described herein or understood by one of ordinary skill in the art from the description herein. The anchor 15p may comprise a spiral band 17. The anchor 15p may be configured to anchor the frame structure 12p to the native valve when the frame structure 12p is in the expanded configuration adjacent the native valve. The frame structure 12p may be configured to be actuated from the unexpanded configuration to the expanded configuration adjacent a native valve in a patient. The spiral band anchor 15p may be deployed and configured to anchor the frame structure 12p of the valve prosthesis 10p adjacent a native valve as described herein. The anchor 15p may, for example, be configured to be fully advanced from a first side of a native valve in a patient (e.g. an atrial side) to a second side of the native valve (e.g. into a ventricle of the heart) and anchor the frame structure 12p to the native valve when the frame structure 12p is in an expanded configuration adjacent the native valve as described herein. The spiral band anchor 15p may be delivered to the native valve by a delivery device as described herein.

The anchor 15p may comprise a spiral band 17 having a free end 22p. The spiral band 17 may be substantially similar to any of the spiral bands described herein. The free end 22p may be substantially similar to the free end of other anchors described herein. The other end of the anchor 15p (e.g., spiral band 17) may be coupled to the top (proximal end), bottom (distal end), or an intermediate portion (e.g. middle) of the frame structure 12p as described herein. Alternatively, or in combination, the other end of the anchor 15p may not be attached to the frame structure 12p as described herein. The free end 22p of the spiral anchor 15p may facilitate capturing of the valve leaflets and/or chordae tendineae within the sweep of the free end during rotation as described herein. During rotation of the spiral anchor 15p, the leaflets and/or chordae tendineae may be captured by the free end 22p and trapped between the valve frame structure 12p and an interior surface of the spiral anchor 15p. The anchor 15p may comprise one or more spaces between loops of the anchor 15p which facilitate movement of the captured tissue (e.g. chordae and/or leaflets) from the free end 22p to the center of the spiral structure with little or no torque and/or rotation of the structures during rotation of the anchor 15p as described herein. At least a portion of the spiral anchor 15p may be formed of a material having sufficient rigidity to hold a predetermined shape as described herein.

In some embodiments, the anchor 15p may comprise a delivery (e.g., elongated) configuration when disposed within a delivery device as described herein. The delivery device may be configured to deploy the anchor 15p from the delivery configuration to an undeployed or first intermediate deployed configuration as described herein (as shown in FIGS. 77 and 78). The anchor 15p may then be actuated into the deployed or second fully deployed configuration (as shown in FIGS. 79 and 80), for example by expanding the frame structure 12p within the anchor 15p or by rotating the anchor 15p to capture the one or more structures as described herein. In some embodiments, the anchor 15p may be configured to be actuated into more than one intermediate deployed configuration, for example, by partial expansion of the frame structure 12p.

The anchor 15p may comprise a plurality of loops of a spiral as described herein. The anchor 15p may comprise a more compact spiral, with more loops, in the undeployed or first intermediate deployed configuration compared to the deployed or second fully deployed configuration. As the anchor 15p expands the spiral loops may unwind. In some embodiments, the outer perimeter of the anchor 15p may be substantially similar in the undeployed (or first intermediate deployed) and deployed (or second fully deployed) configurations. As the spiral loops unwind, the spiral may expand from the center, for example simultaneously with expansion of the frame structure in the center of anchor 15p, such that the spiral loops are expanded against one another as shown in FIG. 79. As will be understood by one of ordinary skill in the art, the shape, size, and number of loops may determine the limits of expansion of the anchor 15p and alteration of any or all of these parameters may be done to generate a final deployed configuration desired from an initial undeployed configuration.

The anchor 15p may have a generally spiral shape in the deployed configuration. The anchor 15p may be formed as a flat spiral (in the deployed configuration) whereby the loops generally are positioned within the same plane (the plane being perpendicular to a longitudinal axis). The plurality of loops of the anchor 15p may be spiral radially outward from a central point or central axis of the spiral, for example along an axis which is coaxial with a longitudinal axis of a delivery device such that the anchor 15p lies approximately along a plane perpendicular to the longitudinal axis of the delivery device as described herein. The plurality of loops may comprise at least 360 degrees of rotation when deployed such that the loops wrap around one another and provide additional mechanical leverage against the frame structure in order to facilitate anchoring of the frame structure as described herein. Additional loops or partial loops may provide additional mechanical strength and/or leverage.

The spiral band anchor 15p may be substantially similar to any of the anchors described herein with the addition of interlocking features 24 disposed along the loops of the anchor 15p (e.g., along the loops of spiral band 17) such that they interlock when expanded against one another. The interlocking features 24 may, for example, comprise correspondingly-shaped waves, bends, humps, or the like disposed on adjacent loops of the spiral band anchor 15p such that the interlocking features 24 on adjacent loops may be nested with each other when the anchor 15p is in the deployed configuration. The interlocking features can provide a locking mechanism in the general sense. In some embodiments, the interlocking features may act more like index features for the opening and/or closing of the spiral band (i.e., expansion and/or contraction of the diameter). In this manner, the interlocking features may index the opening and/or closing by discreet increments. In some embodiments, the interlocking features may positively control the opening and/or closing of the spiral band. One will appreciate from the description herein that the resistance provided by the interlocking features may be adjusted depending on the application. In some embodiments, the resistance may be relatively high to prevent or reduce the risk of the diameter of the spiral anchor or band changing diameter. One will appreciate that the interlocking features may be designed and configured in various other manner. Although shown as a somewhat repeating pattern in FIGS. 77-80, the interlocking features may have one or more shapes and sizes. The pattern may be repeating or non-repeating. The spiral anchor or band may include different sets of interlocking features. For example, it may be desirable to provide one or more sets of interlocking features to index self-assembly and/or anchoring of the spiral anchor or band to the chordae and another set(s) configured to prevent the spiral anchor or band from expanding beyond a certain predetermined diameter, such as to increase the opposing force against the expanding frame.

In some embodiments, the spiral anchor 15p may comprise a more than one pair of interlockingly-shaped features 24 disposed on adjacent loops of the anchor 15p (e.g., on adjacent loops of the spiral band 17) in order to ensure secure locking and/or to provide for a plurality of intermediate expanded/deployed configurations between the fully undeployed and the fully deployed configuration. For example, the spiral band anchor 15p may comprise a plurality of waves 24 in adjacent loops of the generally spiral-shaped anchor 15p which can provide intermittent locking of the anchor 15p as the anchor 15p is deployed in multiple configurations. As the anchor 15p is expanded, the waves 24 may move into and out of nesting with one another, locking when nested together and expanding when enough energy has been applied to disengage the nested waves from one another.

In some embodiments, the plurality of features 24 may be disposed along the generally spiral-shaped anchor 15p at pre-determined distances. In some embodiments, the plurality of features 24 may be disposed along the generally spiral-shaped anchor 15p at regular intervals. In some embodiments, the plurality of features 24 may be disposed along only a portion of the anchor 15p. IN some embodiments, the plurality of features 24 may be disposed along the entire anchor 15p.

In some embodiments, the plurality of interlocking features 24 may comprise two, four, six, eight, ten, twelve, fourteen, sixteen, eighteen, twenty, or more features 24 disposed on adjacent loops of the spiral band 17. For example, each adjacent loop may comprise one, two, three, four, five, six, seven, eight, nine, ten, or more features 24 per loop.

In some embodiments, the plurality of features 24 may comprise a plurality of waves disposed along the generally spiral-shaped anchor 15p such that the anchor resembles a flower-like shape (e.g., as shown in FIGS. 77-80).

It will be understood by one or ordinary skill in the art that any of the anchors described herein may comprise any of the locking mechanisms, or any combination of locking mechanisms, described herein or understood based on the teachings herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the present disclosure. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present disclosure.

Throughout this specification and the claims which follow, unless the context requires otherwise, the word "comprise", and variations such as "comprises" and "comprising" means various components can be co jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The foregoing descriptions of specific embodiments of the present disclosure have been presented for purposes of illustration and description. They are not intended to be exhaustive or to limit the invention to the precise forms disclosed, and obviously many modifications and variations are possible in light of the above teaching. The embodiments were chosen and described to best explain the principles of the invention and its practical application, to thereby enable others skilled in the art to best utilize the present disclosure and various embodiments with various modifications as are suited to the particular use contemplated. It is intended that the scope of the invention be defined by the Claims appended hereto and their equivalents.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for treating a diseased native valve in a patient, the system comprising:
   a frame structure having an unexpanded configuration and an expanded configuration; and
   an anchor comprising a free end and having a flat spiral shape, wherein the flat spiral shape comprises more than one loop positioned within a single plane that is perpendicular to a central longitudinal axis of the anchor;
   wherein the frame structure is configured to be actuated from the unexpanded configuration to the expanded configuration within the anchor and adjacent a native valve in a patient, and
   wherein the flat spiral is configured to circumscribe chordae of the native valve to anchor the frame structure to the native valve.

2. The system of claim 1, wherein the anchor is configured to be fully advanced from an atrial side of the native valve into a ventricle of the heart.

3. The system of claim 2, wherein at least a portion of the anchor is configured to reside within a subvalvular plane of the heart when it anchors the frame structure to the native valve.

4. The system of claim 3, wherein the anchor is configured to reside entirely within the subvalvular plane of the heart when it anchors the frame structure to the native valve.

5. The system of claim 1, wherein the anchor comprises a delivery configuration and a deployed configuration.

6. The system of claim 5, wherein the anchor comprises the flat spiral shape in the deployed configuration.

7. The system of claim 5, wherein the anchor comprises an elongated shape in the delivery configuration.

8. The system of claim 5, wherein the anchor is configured to be actuated from the delivery configuration to the deployed configuration adjacent to the native valve.

9. The system of claim 8, wherein the anchor comprises one or more locking mechanisms configured to maintain the anchor in the deployed configuration.

10. The system of claim 9, wherein the one or more locking mechanisms comprise a frictional band, a polymer coating, or one or more key and one or more key hole features.

11. The system of claim 9, wherein the one or more locking mechanisms comprise a first feature disposed on a first loop of the anchor and a correspondingly-shaped second feature disposed on a second loop of the anchor, the first and second features configured to nest with one another when the anchor is in the deployed configuration.

12. The system of claim 1, wherein the more than one loop extends through about 540 degrees of rotation.

13. The system of claim 1, wherein the more than one loop spirals radially outward from a central point.

14. The system of claim 1, wherein the anchor comprises a super-elastic material.

15. The system of claim 14, wherein the anchor comprises nitinol.

16. The system of claim 1, wherein the frame structure comprises an expandable stent.

17. The system of claim 1, wherein the free end comprises an atraumatic tip.

18. The system of claim 17, wherein the free end comprises a ball tip.

19. The system of claim 1, wherein the free end is configured for piercing tissue.

20. The system of claim 1, wherein the free end is bent distally.

21. The system of claim 1, wherein the anchor comprises a wire.

22. The system of claim 1, wherein the anchor comprises a band.

23. The system of claim 1, wherein the anchor comprises at least one channel or lumen disposed therein.

24. The system of claim 1, wherein the anchor comprises a tapered band.

25. The system of claim 24, wherein the tapered band comprises a support structure and a semi-permeable material or impermeable material disposed therein.

26. The system of claim 25, wherein the semi-permeable material or impermeable material comprises a webbing material, a fabric, a polymeric material, or an elastomeric material.

27. The system of claim 1, wherein the unexpanded configuration is sized and dimensioned for percutaneous insertion and the expanded configuration is sized and dimensioned for implantation in the native valve of the patient.

28. The system of claim 1, wherein the frame structure comprises a first and second opposite ends, the first end extending above a native valve and the second end extending below the native valve when the frame structure is anchored to the native valve.

29. The system of claim 1, further comprising a valve segment within the frame structure comprising a biocompatible one-way valve.

30. The system of claim 29, wherein at least a portion of the valve segment is positioned within at least a portion of the frame structure.

31. The system of claim 29, wherein the valve segment comprises at least one leaflet having an inner layer and an outer layer, and wherein the frame structure is attached to the outer layer at one or more ends of the frame structure.

32. The system of claim 29, wherein the valve segment comprises a plurality of leaflets.

* * * * *